$\qquad$

US010519438B2

(12) United States Patent
Wagner et al.

(10) Patent No.: US 10,519,438 B2
(45) Date of Patent: Dec. 31, 2019

(54) PROTEIN SCREENING METHODS

(71) Applicant: X-Body, Inc., Waltham, MA (US)

(72) Inventors: Richard W. Wagner, Cambridge, MA (US); Alexander Litovchick, Sudbury, MA (US); Yan Chen, Lexington, MA (US)

(73) Assignee: X-BODY, INC., Waltham, MA (US)

( * ) Notice: Subject to any disclaimer, the term of this patent is extended or adjusted under 35 U.S.C. 154(b) by 2 days.

(21) Appl. No.: 15/703,710

(22) Filed: Sep. 13, 2017

(65) Prior Publication Data

US 2018/0094256 A1 Apr. 5, 2018

Related U.S. Application Data

(60) Division of application No. 14/796,480, filed on Jul. 10, 2015, now Pat. No. 9,803,193, which is a division of application No. 13/009,500, filed on Jan. 19, 2011, now Pat. No. 9,134,304, which is a continuation of application No. PCT/US2009/051716, filed on Jul. 24, 2009.

(60) Provisional application No. 61/170,029, filed on Apr. 16, 2009, provisional application No. 61/090,111, filed on Aug. 19, 2008, provisional application No. 61/083,813, filed on Jul. 25, 2008.

(51) Int. Cl.
*C12N 15/10* (2006.01)
*G01N 33/53* (2006.01)
*G01N 33/543* (2006.01)
*G01N 33/68* (2006.01)
*C07K 19/00* (2006.01)

(52) U.S. Cl.
CPC ......... *C12N 15/1086* (2013.01); *C07K 19/00* (2013.01); *C12N 15/1062* (2013.01); *G01N 33/5308* (2013.01); *G01N 33/54366* (2013.01); *G01N 33/6845* (2013.01); *C07K 2317/10* (2013.01); *C07K 2317/40* (2013.01); *C07K 2317/56* (2013.01); *C12N 15/1075* (2013.01)

(58) Field of Classification Search
None
See application file for complete search history.

(56) References Cited

U.S. PATENT DOCUMENTS

| 5,643,768 A | 7/1997 | Kawasaki |
| 5,843,701 A | 12/1998 | Gold et al. |
| 5,922,545 A | 7/1999 | Mattheakis et al. |
| 6,028,066 A | 2/2000 | Unger |
| 6,143,503 A | 11/2000 | Baskerville et al. |
| 6,153,383 A | 11/2000 | Verdine et al. |
| 6,258,558 B1 | 7/2001 | Szostak et al. |
| 6,348,315 B1 | 2/2002 | Pluckthun et al. |
| 6,361,943 B1 | 3/2002 | Yanagawa et al. |
| 6,416,950 B1 | 7/2002 | Lohse et al. |
| 6,429,300 B1 | 8/2002 | Kurz et al. |
| 6,436,665 B1 | 8/2002 | Kuimelis |
| 6,489,116 B2 | 12/2002 | Wagner |
| 6,537,749 B2 | 3/2003 | Kuimelis et al. |
| 6,602,685 B1 | 8/2003 | Lohse |
| 6,620,587 B1 | 9/2003 | Taussig et al. |
| 6,623,926 B1 | 9/2003 | Lohse et al. |
| 6,660,473 B1 | 12/2003 | Lohse et al. |
| 6,794,132 B2 | 9/2004 | Buechler et al. |
| 6,846,655 B1 | 1/2005 | Wagner et al. |
| 6,951,725 B2 | 10/2005 | Kurz et al. |
| 7,074,557 B2 | 7/2006 | Osbourn et al. |
| 7,416,847 B1 | 8/2008 | Lindqvist et al. |
| 7,527,954 B2 | 5/2009 | Bertschinger et al. |
| 7,572,577 B2 | 8/2009 | He et al. |
| 7,842,476 B2 | 11/2010 | McGregor et al. |
| 2001/0046680 A1 | 11/2001 | Yu |
| 2003/0022236 A1 | 1/2003 | Szostak et al. |
| 2003/0027194 A1 | 2/2003 | Kurz et al. |
| 2004/0018536 A1 | 1/2004 | Yanagawa et al. |
| 2004/0043384 A1 | 3/2004 | Oleinikov |
| 2005/0010028 A1 | 1/2005 | Yanagawa et al. |
| 2005/0191626 A1 | 9/2005 | Taira et al. |
| 2006/0183885 A1 | 8/2006 | Miyamoto et al. |

FOREIGN PATENT DOCUMENTS

| AU | 776478 B2 | 1/2002 |
| EP | 1 211 514 A1 | 6/2002 |
| WO | 2000/009741 A1 | 2/2000 |
| WO | 2000/032823 A1 | 6/2000 |
| WO | 2000/042221 A2 | 7/2000 |
| WO | 2001/007657 A1 | 2/2001 |
| WO | 2004/053121 A1 | 6/2004 |
| WO | 2004/083428 A1 | 9/2004 |
| WO | 2006/038027 A2 | 4/2006 |
| WO | 2006/081623 A1 | 8/2006 |

OTHER PUBLICATIONS

Hammond et al., "In Vitro Selection and Characterization of Bcl-XL-binding Proteins from a Mix of Tissue-specific mRNA Display Libraries", The Journal of Biological Chemistry, 2001, pp. 20898-20906 (Year: 2001).*
Barrick et al. (2001) "Selection of RNA-binding peptides using mRNA-peptide fusions," Methods. 23:287-293.
Biyani et al. (2006) "Solid-phase translation and RNA-protein fusion: a novel approach for folding quality control and direct immobilization of proteins using anchored mRNA," Nucleic Acids Research. 34(20):e140.
Cammack et al: Eds. (2000) Oxford Dictionary of Biochemistry and Molecular Biology, Revised Edition. Oxford University Press. p. 384.
Doi et al. (1999) "STABLE: protein-DNA fusion system for screening of combinatorial protein libraries in vitro," FEBS Lett. 457(2):227-230.
Fukada et al. (2006) "In vitro evolution of single-chain antibodies using mRNA display," Nucleic Acids Research. 34(19): e127.

(Continued)

*Primary Examiner* — Lianko G Garyu
(74) *Attorney, Agent, or Firm* — Lathrop Gage LLP; James H. Velema, Esq.

(57) ABSTRACT

The invention provides methods and compositions useful for identifying polypeptides with desired characteristics in vitro.

8 Claims, 37 Drawing Sheets

Specification includes a Sequence Listing.

(56) References Cited

OTHER PUBLICATIONS

Krumpe et al. (2007) "Potential of phage-displayed peptide library technology to identify functional targeting peptides," Expert Opin. Drug Discov. 2(4):525-537.

McPherson et al. (2002) "Drug Receptor Identification from Multiple Tissues Using Cellular-Derived mRNA Display Libraries," Chemistry and Biology. 9(6):691-698.

Miyamoto-Sato et al. (2006) "Puromycin technology for in vitro evolution and proteome exploration," Viva Origino. 34:148-154.

Reiersen et al. (2005) "Covalent antibody display—an in vitro antibody-DNA library selection system," Nucleic Acids Research. 33(1):e10.

Roberts et al. (1997) "RNA-peptide fusions for the in vitro selection of peptides and proteins," Proc. Natl. Acad. Sci. USA. 94(23):12297-12302.

Sepp et al. (2002) "Microbead display by in vitro compartmentalisation: selection for binding using flow cytometry," FEBS Letters. 532(3):455-458.

Voet et al. (2002) Fundamentals of Biochemistry. pp. 867-868 and G-15.

Yonezawa et al. (2004) "DNA display of biologically active proteins for in vitro protein selection," J. Biochem. 135:285-288.

International Search Report with Written Opinion corresponding to International Patent Application No. PCT/US2009/051716, dated Mar. 15, 2012.

Supplementary European Search Report corresponding to European Patent Application No. 09801086, dated Sep. 1, 2011.

\* cited by examiner

Example of a single clone of the VH library

TAATACGACTCACTATA
GGGACAATTACTATTTACAATTACAAGT
CTGGGCTGAGGTGAAGAAGCCTGGGGCCTCAGTGAAGGTTCCTGCAAGGCTTCTG
GATACACCTTCAGTAATAATGCTATACATTGGGTGCGCCAGGCCCCGGACAAAGGCTTG
AATGGATGGGATGGATCAACGGTGGCAATGGAACACAGATAATTCACAGAAATTCCAGG
GCAGAGTCACCATTACTAGGGACACGTCCACCTACAGGAGCTGAGCAGCC
TGATATCTGAAGACACGGCTGTATATTACTGTGCGCATAAGACAGTATAGCAGTCGGCA
GCCCTTTGACCTCTGGGCCAGGGAACCCTGGTCACCGTCTCCTCA GCA TCC GCT A
GAC TAC AAG GAC GAC GAC AAG TCG TCC TTA T TAA AAA AAA AAA AAA
AAAAAA (SEQ ID NO: 66)

- ░ Transcription and Translation start sequence
- ▒ VH sequence
- ░ Cμ sequence
- ☐ flag tag sequence
- ■ GGGG complement for mRNA display
- ▥ additional complement seq for SA display XB_S7    T7TMVUTR2
5'-TAATACGACTCACTATAGGGACAATTACTATTTACAATTACA-3' (SEQ ID NO: 52)

XB_S5-1
5'TTTTTTTTTTTTTTTTTTTTAAATAGCGGATGCTAAGGACGACTTGTCGTCGTCCTTGTAGTCGGTTGGGGCGGATGCACTCCC-3' (SEQ ID NO: 54)

XB_S6-1
5'AAATAGCGGATGCTAAGGACGACTTGTCGTCGTCCTTGTAGTCGGTTGGGGCGGATGCACTCCC-3'
(SEQ ID NO: 67)

Fig. 15

Amplicon sequencing Titanium 454: ~400 nts run

454 layout

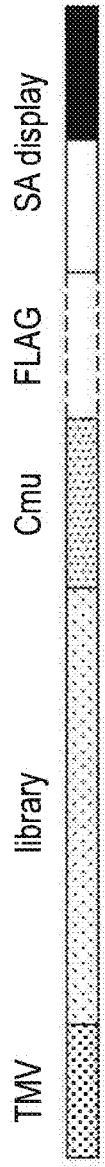

TMV    library    Cmu    FLAG    SA display

Addition of 454 primers + coding sequences by PCR

Forward: GCCTCCCTCGCGCCATCAG (N6) gene-specific primer (SEQ ID NO: 61)
454 adaptor "A": GCCTCCCTCGCGCCATCAG (SEQ ID NO: 61)
Sequencing primer "A": GCCTCCCTCGCGCCA (SEQ ID NO: 70)

Reverse: GCCTTGCCAGCCCGCTCAG (coding) gene-specific primer (SEQ ID NO: 62)
454 adaptor "B": GCCTTGCCAGCCCGCTCAG (SEQ ID NO: 62)
Sequencing primer "B": GCCTTGCCAGCCCGC (SEQ ID NO: 71)

Sequencing could be done from either side or both; we chose Primer B side- reverse primer, negative strand (see below). Underlined are calibration sequences (internal standards).

*Fig. 17*

Examples of pool tagging:

3' end Primers with const 4-nts codes (red)

>1 (SEQ ID NO: 82)
GCCTTGCCAGCCGGCTCAG AATT TGG GGC GGA TGC ACT CCC
>2 (SEQ ID NO: 83)
GCCTTGCCAGCCGGCTCAG GGAA TGG GGC GGA TGC ACT CCC
>3A (SEQ ID NO: 84)
GCCTTGCCAGCCGGCTCAG TTAA TGG GGC GGA TGC ACT CCC
>3B (SEQ ID NO: 85)
GCCTTGCCAGCCGGCTCAG GGCC TGG GGC GGA TGC ACT CCC
>3C (SEQ ID NO: 86)
GCCTTGCCAGCCGGCTCAG CCGG TGG GGC GGA TGC ACT CCC
>3D (SEQ ID NO: 87)
GCCTTGCCAGCCGGCTCAG TTCC TGG GGC GGA TGC ACT CCC
>3E (SEQ ID NO: 88)
GCCTTGCCAGCCGGCTCAG AAGG TGG GGC GGA TGC ACT CCC
>3F (SEQ ID NO: 89)
GCCTTGCCAGCCGGCTCAG CCTT TGG GGC GGA TGC ACT CCC

Primer B     Pool code

Example of individual molecule tagging (to filter PCR artifacts): 5' end primer (SEQ ID NO: 59)

5'-GCCTCCCTCGGCCATCAG (NNNNNN) GGGACAATTACTATTACAATTACAATG-3'

Primer A     Random N6     TMV

*Fig. 35*

Sources of the cells for the amplification of VH domains

Total: over 600 healthy individuals:

PBMC         601 donors
Splenocytes   13 donors
Bone marrow   10 donors

Diversity

VH library: $10^9$-$10^{10}$
VL library: $10^6$-$10^7$

Combinatorial diversity: $10^{15}$-$10^{17}$

- Fully captured the natural antibody repertoire
- The VH fusion library representing 100-1000 copies of each molecule

*Fig. 36*

PROTEIN SCREENING METHODS

RELATED APPLICATIONS

This application is a division of U.S. patent application Ser. No. 14/796,480, filed Jul. 10, 2015, which is a division of U.S. patent application Ser. No. 13/009,500, filed Jan. 19, 2011, now U.S. Pat. No. 9,134,304, which is a continuation of International Patent Application No. PCT/US2009/051716, filed Jul. 24, 2009, which claims priority to U.S. Provisional Application No. 61/083,813, filed Jul. 25, 2008, U.S. Provisional Application No. 61/090,111, filed Aug. 19, 2008, and U.S. Provisional Application No. 61/170,029, filed Apr. 16, 2009, the entire contents of which are hereby incorporated herein by reference.

BACKGROUND

It is well understood that, in the use of display and selection technologies, access to greater diversity allows for a more effective selection of molecules with the highest affinity, specificity, stability, and/or other desirable characteristics.

Past methods that have been developed include phage display, ribosome display, CIS display, and mRNA display. Recently, there has been increased interest in identifying molecules using in vivo screening (J Control Release. 2003 Aug. 28; 91(1-2):183-6). This approach has been made possible using phage display, but suffers from the limited diversity afforded by the phage display technologies. Ribosome or mRNA display would fail for this application due to the instability of the RNA species. Therefore, development of DNA-protein fusions would be highly desirable, due to the increased stability of the species.

Three types of DNA-protein fusions have been described. CIS display is one method where coupled in vitro transcription/translation is used to generate a dsDNA binding protein that covalently binds to the DNA as it is being transcribed and translated (PNAS, 101(9): 2806-2810). However, one of the primary limitations of this technology is that the synthesized protein can bind to any neighboring DNAs that are nearby during the transcription/translation process, resulting in mis-tagged fusions. The second method is that of Kurz and Lohse (Chembiochem. 2001 Sep. 3; 2(9):666-72). This method involves formation of covalent adducts with mRNA using a multifunctional species that can covalently bond with translated protein, create a ribosomal pause at the covalent adduct on RNA, and serve as a primer for reverse transcription. A limitation of this method is the inefficiency of the covalent linking step with RNA using psoralen. The third method is that of Yonezawa et al. (Nucleic Acids Res. 2003 Oct. 1; 31(19): e118.) In this method, DNA encoding streptavidin and a region of diverse peptides is biotinylated, placed in a synthetic microsphere with translation machinery and translated such that the streptavidin (tetrameric) will bind to the biotinylated DNA. The limitation of this method is that the resultant species is tetrameric, which can be troublesome for affinity selections due to multiple binding species on one particle (rebinding effect).

Herein is described a simple, efficient method for generating nucleic acid protein fusions is required which may employ noncovalent attachment between the nucleic acid and the protein, and which will allow the formation of DNA-protein fusions.

SUMMARY OF THE INVENTION

The present invention provides compositions and methods to select and evolve desired properties of proteins and nucleic acids. In various embodiments, the current invention includes small molecules linked to nucleic acid or modified nucleic acid. Other embodiments include methods for producing polypeptides, including peptides with modified amino acids, assays for enabling selection of individual members of the population having desired properties, and methods for generating new variations of polypeptides with improved properties.

In one aspect the invention provides a heterobifunctional complex comprising:
- (a) a first nucleic acid molecule comprising a polypeptide-encoding sequence;
- (b) a polypeptide encoded by the first nucleic acid molecule; and
- (c) a second nucleic acid molecule comprising a nucleic sequence
  complementary to a portion of the first nucleic acid molecule, wherein the first nucleic acid molecule is bound to the second nucleic molecule through complementary nucleic acid base pairing, and wherein the second nucleic acid molecule is non-covalently bound to the polypeptide.

In some embodiments, this heterobifunctional complex further comprises:
- (a) a high affinity ligand covalently bound to the second nucleic acid molecule; and
- (b) a ligand acceptor bound to a peptide acceptor, wherein the high affinity ligand is bound to the ligand acceptor and the peptide acceptor is covalently bound to the polypeptide. In some embodiments, this heterobifunctional complex further comprises a second high affinity ligand, wherein the second high affinity ligand is covalently bound to the peptide acceptor, and wherein the second high affinity ligand is bound to the ligand acceptor. In some embodiments, the peptide acceptor in this heterobifunctional complex is bound to the second high affinity ligand through a linker. In one preferred embodiment, the linker comprises polyethylene glyocol. In another preferred embodiment, the linker further comprises a polysialic acid linker. In some embodiments, the ligand acceptor in this heterobifunctional complex is covalently bound to the peptide acceptor.

In some embodiments, this heterobifunctional complex further comprises:
- (a) a ligand acceptor covalently bound to the second nucleic acid molecule; and,
- (b) a high affinity ligand bound to a peptide acceptor, wherein the ligand acceptor is bound to the high affinity ligand and the peptide acceptor is covalently bound to the C-terminus of the polypeptide.

In other embodiments, this heterobifunctional complex further comprises a third nucleic acid molecule, comprising a nucleic sequence complementary to a portion of the second nucleic acid molecule, wherein the third nucleic acid molecule is bound to the second nucleic molecule through complementary nucleic acid base pairing, wherein the third nucleic acid molecule is covalently bound to a peptide acceptor, and wherein the peptide acceptor is covalently bound to the polypeptide.

In some embodiments, the second nucleic acid molecule in the complexes described above is a branched nucleic acid molecule. In some embodiments, the second nucleic acid molecule in the complexes described above is capable of acting as a primer for reverse transcription of the first nucleic acid molecule.

In another aspect, this invention provides an X-display complex (e.g., a nucleic acid polypeptide complex) comprising:

(a) a nucleic acid molecule comprising a polypeptide-encoding sequence, covalently bound to a first high affinity ligand;
(b) a polypeptide encoded by the nucleic acid molecule;
(c) a ligand acceptor bound to a peptide acceptor, wherein the high affinity ligand is bound to the ligand acceptor and the peptide acceptor is covalently bound to the C-terminus of the polypeptide.

In some embodiments, the ligand acceptor in this X-display complex is covalently bound to the peptide acceptor. In some embodiments, this X-display complex further comprises a second high affinity ligand, wherein the second high affinity ligand is covalently bound to the peptide acceptor, and wherein the second high affinity ligand is bound to the ligand acceptor.

In another aspect, this invention provides an X-display complex comprising:
(a) a nucleic acid molecule comprising a polypeptide-encoding sequence, covalently bound to a first high affinity ligand;
(b) a first ligand acceptor covalently bound to a second high affinity ligand; and,
(c) a polypeptide encoded by the first nucleic acid molecule, wherein the polypeptide comprises a second ligand acceptor,
wherein the first high affinity ligand is bound to the first ligand acceptor, and the second high affinity ligand is bound to the second ligand acceptor.

In some embodiments, the first or second high affinity ligand bound to the complexes described above is biotin.

In some embodiments, the first or second high affinity ligand bound to the complexes described above is selected from the group comprising FK506, methotrexate, PPI-2458, biotin, hirudin, ZFVp(O)F, gluorescein-biotin, ABD (albumin binding domain), 18 bp DNA, RNAse A, cloroalkanes, Aryl (beta-amino ethyl) ketones, and Protein A.

In some embodiments, the first or second ligand acceptor in the complexes described above is selected from the group comprising FKBP12, dihydrofolate reductase, methionine aminopeptidase, dimeric streptavidin, streptavidin tetramer, thrombin, carboxypeptidase, Monovalent Ab, HSA (albumin), Zn finger, hRI (RNase inhibitor), mutated haloalkane dehalogenase, haloTag, and sortase.

In some embodiments, the first or second ligand acceptor in the complexes described above is streptavidin.

In some embodiments, the polypeptide described above is chosen from the group comprising an antibody, a VH domain, a VL domain, a Fab fragment, a single chain antibody, a nanobody, a unibody, an adnectin, an affibody, a DARPin, an anticalin, an avimer, a $^{10}$Fn3 domain, and a versabody.

In another aspect, this invention provides an X-display complex comprising:
(a) a nucleic acid molecule comprising a polypeptide-encoding sequence, covalently attached to a ligand; and
(b) a polypeptide encoded by the first nucleic acid molecule, wherein the polypeptide comprises a ligand acceptor,
wherein the ligand is bound to the ligand acceptor.

In some embodiments, the ligand bound to the X-display complex is FK506 and the ligand acceptor in the nucleic acid-polypeptide complexes is the FK506-binding domain of FKBP.

In some embodiments, the first nucleic acid molecule bound to the complexes described above is selected from the group consisting of ssRNA, ssDNA, ssDNA/RNA hybrid dsDNA, and dsDNA/RNA hybrid.

In some embodiments, the polypeptide-encoding sequence of the first nucleic acid molecule bound to the complexes described above does not contain an in-frame stop codon.

In some embodiments, the polypeptide described above is a binding protein. In one preferred embodiment, the binding protein is the VH or VL domain of an antibody.

In some embodiments, the nucleic acid-polypeptide complexes described above does not contain a ribosome.

In another aspect, this invention also provides a library comprising a plurality of the X-display complexes described above, wherein at least a portion of the complexes contain different polypeptide-encoding sequences.

In another aspect, this invention also provides a method of a library of nucleic acid-polypeptide complexes comprising the steps of:
providing a library of mRNA sequences comprising a sequence element complementary to a first nucleic acid linker
providing a first nucleic acid linker operably linked to a first high affinity ligand such that the first nucleic acid linker binds to the mRNA through complementary nucleic acid base pairing
providing second high affinity ligand operably linked to a peptide acceptor
providing a ligand acceptor with at least two binding sites or providing at least such that the ligand acceptor binds to the first high affinity ligand and the second high affinity ligand
allowing translation of the mRNA to occur such that the peptide acceptor binds to the translated protein thereby forming a nucleic acid-polypeptide complex linking the mRNA to the protein.

In some embodiments, the method further comprises
allowing reverse transcription of the mRNA using the first nucleic acid linker in the X-display complex as a primer such that a DNA/RNA hybrid is formed.

In one preferred embodiment, the method further comprises
degrading the mRNA and synthesizing a complementary DNA strand thereby forming a DNA/DNA hybrid in the nucleic acid-polypeptide complex.

In some embodiments, the mRNA in the library further comprises a TMV enhancer.

In some embodiments, the mRNA in the library further comprises a Cµ sequence.

In some embodiments, the mRNA in the library further comprises a FLAG tag.

In some embodiments, the mRNA in the library further comprises an SA display sequence.

In some embodiments, the mRNA in the library further comprises an A20 tail.

In another aspect, this invention also provides a library of nucleic acid-polypeptide complexes produced by the methods described in this invention.

In another aspect, this invention also provides a method of selecting an isolated nucleic acid molecule encoding a polypeptide capable of binding to an antigen of interest, comprising the steps of:
(a) providing the library of X-display complexes described in this invention;
(b) contacting the library with an antigen of interest;
(c) selecting from the library at least one X-display complex that binds to the antigen of interest; and,
(d) isolating the polypeptide encoding sequence of the selected X-display complex.

In another aspect, this invention also provides a method of producing a polypeptide capable of binding to an antigen of interest, comprising introducing a polypeptide encoding sequence identified by the method described in this invention into an expression environment such that the encoded polypeptide is produced.

In another aspect, this invention also provides an isolated nucleic acid molecule encoding a polypeptide capable of binding to an antigen of interest, selected by the method described in this invention.

In another aspect, this invention also provides a X-display complex comprising:

(a) a first nucleic acid molecule comprising a polypeptide-encoding sequence;

(b) a polypeptide encoded by the first nucleic acid molecule;

(c) a second nucleic acid molecule comprising a nucleic sequence complementary to a portion of the first nucleic acid molecule;

(d) a first high affinity ligand covalently bound to the second nucleic acid molecule;

(e) a first ligand acceptor; and (f) a second high affinity ligand covalently bound through via one or more linking molecules to a peptide acceptor, wherein the first nucleic acid molecule is bound to the second nucleic molecule through complementary nucleic acid base pairing, wherein the first high affinity ligand is noncovalently bound to the ligand acceptor at a first binding site, wherein the second ligand is noncovalently bound to the ligand acceptor at a second binding site, and wherein the one or more linking molecules are polyethylene glycol molecules.

In some embodiments, the first high affinity ligand in this complex is biotin and the ligand acceptor is selected from the group comprising streptavidin, dimeric streptavidin, and tetrameric streptavidin.

In some embodiments, the second high affinity ligand in this complex is biotin and the ligand acceptor is selected from the group comprising streptavidin, dimeric streptavidin, and tetrameric streptavidin.

In some embodiments, the first or second high affinity ligand in this complex is selected from the group comprising FK506, methotrexate, PPI-2458, biotin, hirudin, ZFVp(O)F, fluorescein-biotin, ABD (albumin binding domain), 18 bp DNA, RNAse A, cloroalkanes, aryl (beta-amino ethyl) ketones, and protein A.

In some embodiments, this complex further comprises a second ligand acceptor.

In some embodiments, the second ligand acceptor in the complex described above is selected from the group comprising FKBP12, dihydrofolate reductase, methionine aminopeptidase, dimeric streptavidin, streptavidin tetramer, thrombin, carboxypeptidase, monovalent Ab, HSA (albumin), Zn finger, hRI (RNase inhibitor), mutated haloalkane dehalogenase, haloTag, and sortase.

In some embodiments, the peptide acceptor in this complex is puromycin.

In some embodiments, the first or second nucleic acid molecule in this complex further comprises psoralen.

In some embodiments, the polypeptide is chosen from the group comprising an antibody, a VH domain, a VL domain, a Fab fragment, a single chain antibody, a nanobody, a unibody, an adnectin, an affibody, a DARPin, an anticalin, an avimer, a $^{10}$Fn3 domain, and a versabody.

In another aspect, this invention provides a heterobifunctional complex comprising:

(a) a first high affinity ligand covalently bound to a nucleic acid molecule;

(b) a second high affinity ligand covalently bound to a peptide acceptor; and (c) a ligand acceptor comprising two or more ligand binding sites;

wherein the first and second are bound to the ligand acceptor at distinct ligand binding sites.

In some embodiments, the first and the second high affinity ligand in this complex are identical.

In some embodiments, the first and the second high affinity ligand in this complex are biotin.

In some embodiments, the nucleic acid molecule in this complex comprises a psoralen moiety.

In some embodiments, the peptide acceptor in this complex is puromycin.

In some embodiments, the ligand acceptor in this complex is a multimeric protein.

In some embodiments, the ligand acceptor in this complex is streptavidin.

BRIEF DESCRIPTION OF THE DRAWINGS

FIG. 15 (SEQ ID NOS: 66, 52, 54, and 67) illustrates a sample single clone for a VH library. The illustration shows transcription and translation start sequences, VH sequence, Cu sequence, FLAG tag sequence, a DNA segment complementary to a linker (e.g., an NA linker)

FIG. 16A first depicts an X-display complex comprising an mRNA molecule (containing appropriate linkers, tags, complementary regions, and a poly-A tail) which is attached to a Linker/RT primer (an NA linker) via complementary strand pairing and a psoralen link. The NA linker is further covalently bound to a Biotin (B) molecule which is associated with a streptavidin molecule. The streptavidin is associated with a second biotin molecule, which itself is covalently bound to puromycin which has been attached to a translated protein. FIG. 16A (SEQ ID NOS: 68 and 69) depicts the reverse transcription (Step 1) and RNA degradation (Step 2). FIG. 16B depicts second strand synthesis to create a DNA/RNA hybrid (Step 4). The final depiction of FIG. 16B is the final dsDNA X-display complex (i.e., X-display complex).—

FIG. 17 (SEQ ID NOS: 61, 62, 70, and 71) depicts a potential library member and how, in some embodiments, primers may be employed with 454 sequencing.

FIG. 35 (SEQ ID NOS: 82-89, 59) illustrates the pool tagging which may be used in the library design to allow for pooling of multiple selection rounds into one sequencing run.

FIG. 36 illustrates exemplary donor cells for the preparation of a VH library.

DETAILED DESCRIPTION OF THE INVENTION

Figure 1:
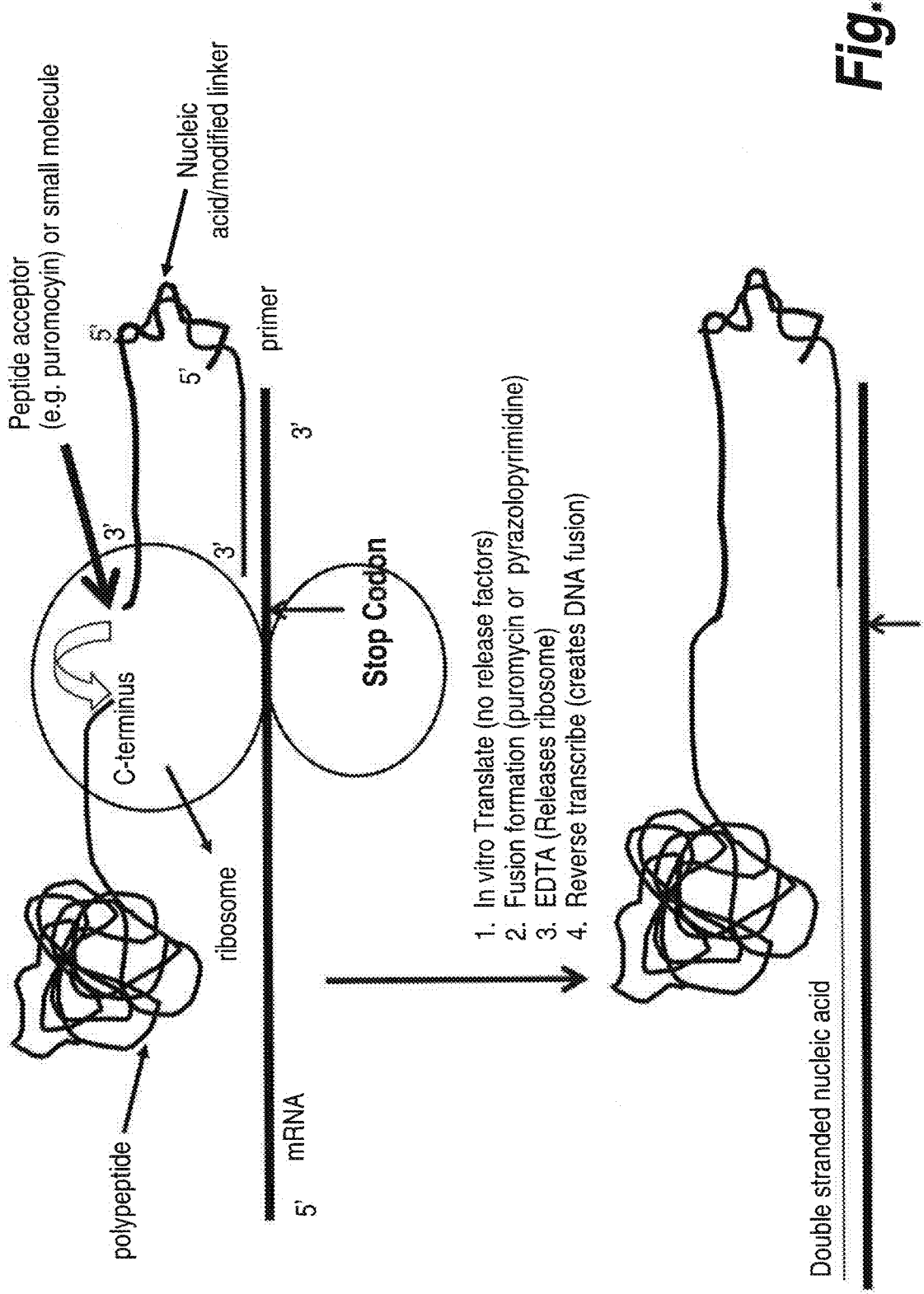
FIG. 1 illustrates one embodiment of the methodology described herein.

The present invention provides compositions and methods to select and evolve desired properties of proteins and nucleic acids. The method may be referred to herein as "X-Display" or, in some embodiments were streptavidin is employed, "SA Display." In various embodiments, the current invention includes small molecules linked to nucleic acid or modified nucleic acid. Other embodiments include methods for producing polypeptides, including peptides with modified amino acids, assays for enabling selection of individual members of the population having desired properties, and methods for generating new variations of polypeptides with improved properties.

By "selecting" is meant substantially partitioning a molecule from other molecules in a population. As used herein, a "selecting" step provides at least a 2-fold, in some embodiments 3-fold, 5-fold, 10-fold, 20-fold, preferably 30-fold, more preferably, a 100-fold, and, most preferably, a 1000-fold enrichment of a desired molecule relative to undesired molecules in a population following the selection step. A selection step may be repeated any number of times, and different types of selection steps may be combined in a given approach.

By a "protein" is meant any two or more naturally occurring or modified amino acids joined by one or more peptide bonds. "Protein" and "peptide" are used interchangeably herein.

By "RNA" is meant a sequence of two or more covalently bonded, naturally occurring or modified ribonucleotides. One example of a modified RNA included within this term is phosphorothioate RNA.

By "DNA" is meant a sequence of two or more covalently bonded, naturally occurring or modified deoxyribonucleotides.

By a "nucleic acid" is meant any two or more covalently bonded nucleotides or nucleotide analogs or derivatives. As used herein, this term includes, without limitation, DNA, RNA, and PNA. The term "nucleic acid" may include a modified nucleic acid, and, accordingly, nucleic acid and modified nucleic acid may be used interchangeably.

The term "nucleotide analog" or "nucleotide derivative" or "modified nucleic acid" as used herein refers to modified or non-naturally occurring nucleotides such as 5-propynyl pyrimidines (i.e., 5-propynyl-dTTP and 5-propynyl-dTCP), 7-deaza purines (i.e., 7-deaza-dATP and 7-deaza-dGTP). Nucleotide analogs include base analogs and comprise modified forms of deoxyribonucleotides as well as ribonucleotides.

By a "peptide acceptor" is meant any molecule capable of being added to the C-terminus of a growing protein chain by the catalytic activity of the ribosomal peptidyl transferase function. Typically, such molecules contain (i) a nucleotide or nucleotide-like moiety (for example, adenosine or an adenosine analog (di-methylation at the N-6 amino position is acceptable)), (ii) an amino acid or amino acid-like moiety (for example, any of the 20 D- or L-amino acids or any amino acid analog thereof (for example, O-methyl tyrosine or any of the analogs described by Ellman et al., Meth. Enzymol. 202:301, 1991), and (iii) a linkage between the two (for example, an ester, amide, or ketone linkage at the 3' position or, less preferably, the 2' position); preferably, this linkage does not significantly perturb the pucker of the ring from the natural ribonucleotide conformation. Peptide acceptors may also possess a nucleophile, which may be, without limitation, an amino group, a hydroxyl group, or a sulfhydryl group. In addition, peptide acceptors may be composed of nucleotide mimetics, amino acid mimetics, or mimetics of the combined nucleotide-amino acid structure.

As used herein, the terms "X-display complex," "nucleic acid-polypeptide complex," and "nucleic acid-protein fusions" are interchangeable and are meant to refer to a complex formed from the interaction, either directly or indirectly, of a nucleic acid and a protein (or peptide or fragment thereof) encoded by the nucleic acid. In some instances the X-display complexes may be referred to "display complexes" or "display fusions" and the skilled artisan will understand by the context of such use that it should not be confused with other types of display systems which may be referenced herein. In some embodiments the nucleic acid is RNA, e.g., mRNA. In other preferred embodiments the nucleic acid is DNA or cDNA. Accordingly, in some embodiments where the goal is to display a complex containing DNA, the X-display complex may be called a "DNA-protein fusion" or "DNA-display fusion." It is important to note that the use of the term "fusion" does not imply or suggest that the nucleic acid is covalently attached to the peptide or protein. In some embodiments the RNA or DNA may be modified or altered. In preferred embodiments the interaction between the nucleic acid and the protein is noncovalent (e.g., the interaction may be mediated by biotin/streptavidin interactions, linker molecules, and the like as described herein). In preferred embodiments the nucleic acid is mRNA or modified mRNA.

By an "altered function" is meant any qualitative or quantitative change in the function of a molecule.

By "binding partner," as used herein, is meant any molecule which has a specific, covalent or non-covalent affinity for a portion of a desired DNA-protein fusion. Examples of binding partners include, without limitation, members of antigen/antibody pairs, protein/inhibitor pairs, receptor/ligand pairs (for example cell surface receptor/ligand pairs, such as hormone receptor/peptide hormone pairs), enzyme/substrate pairs (for example, kinase/substrate pairs), lectin/carbohydrate pairs, oligomeric or heterooligomeric protein aggregates, DNA binding protein/DNA binding site pairs, RNA/protein pairs, and nucleic acid duplexes, heteroduplexes, or ligated strands, as well as any molecule which is capable of forming one or more covalent or non-covalent bonds (for example, disulfide bonds) with any portion of a X-Display complex.

By a "solid support" is meant, without limitation, any column (or column material), bead, test tube, microtiter dish, solid particle (for example, agarose or sepharose), microchip (for example, silicon, silicon-glass, or gold chip), or membrane (for example, the membrane of a liposome or vesicle) to which an affinity complex may be bound, either directly or indirectly (for example, through other binding partner intermediates such as other antibodies or Protein A), or in which an affinity complex may be embedded (for example, through a receptor or channel).

Nucleic Acid or Modified Nucleic Acid Linkers to Mediate the X-Display Complex

In one aspect of the invention a nucleic acid (e.g., a native mRNA or modified mRNA) may be attached to its encoded protein at the end of translation by the use of a nucleic acid or modified nucleic acid linker ("NA linker") which is hybridized at the 3' end of the nucleic acid. In such an embodiment the NA linker has inverted polarity in the linker so that it effectively has two 3' ends, of which the non-hybridized end has attached to it a puromycin or related analogue or a small molecule capable of binding covalently or noncovalently with high affinity to the polypeptide protein. Accordingly, in some embodiments, the X-display complex is formed by the interaction of the protein and the nucleic acid with the NA linker.

In some embodiments the NA linker is a Psoralen linker. In some preferred embodiments the linker is XB-PBI. In some embodiments XB-DDB may be used. In some preferred embodiments the linker (e.g., a PBI linker or DDB linker) is attached to a high affinity ligand (e.g., biotin), i.e., the linker includes the high affinity ligand.

In some embodiments a nucleic acid (e.g., a native mRNA or modified mRNA) may be cross linked to an NA linker which is further attached to a peptide acceptor or a high affinity ligand. Such cross-linking may be accomplished by any methods known in the art. For example, U.S. Pat. No. 6,416,950, which is incorporated herein by reference in its entirety) describes methods making such crosslinks (see, e.g., FIGS. 9-13 of U.S. Pat. No. 6,416,950).

In a further embodiment, the invention includes a dual function NA linker with inverted 5'-3' polarity in the linker, such that it is capable of hybridizing to the nucleic acid, e.g. an mRNA or modified mRNA template, wherein the hybridization occurs on one 3' end of the mRNA outside of the coding region, and wherein the nucleic acid/modified linker carries on its other 3' end a peptide acceptor such as puromycin or functional analogues thereof (for example, but not limited to, pyrazolopyrimidine) or a small molecule capable of binding covalently or with high affinity to the polypeptide protein.

In several embodiments, a nucleic acid, preferably an mRNA or modified mRNA, is hybridized to the NA linker at the 3' end, which is itself bound covalently or with high affinity to the polypeptide (or modified polypeptide) through a covalent bond or by a high affinity noncovalent bond.

In further embodiments, the NA linker is capable of serving as a primer to reverse transcribe the mRNA.

Figure 2:
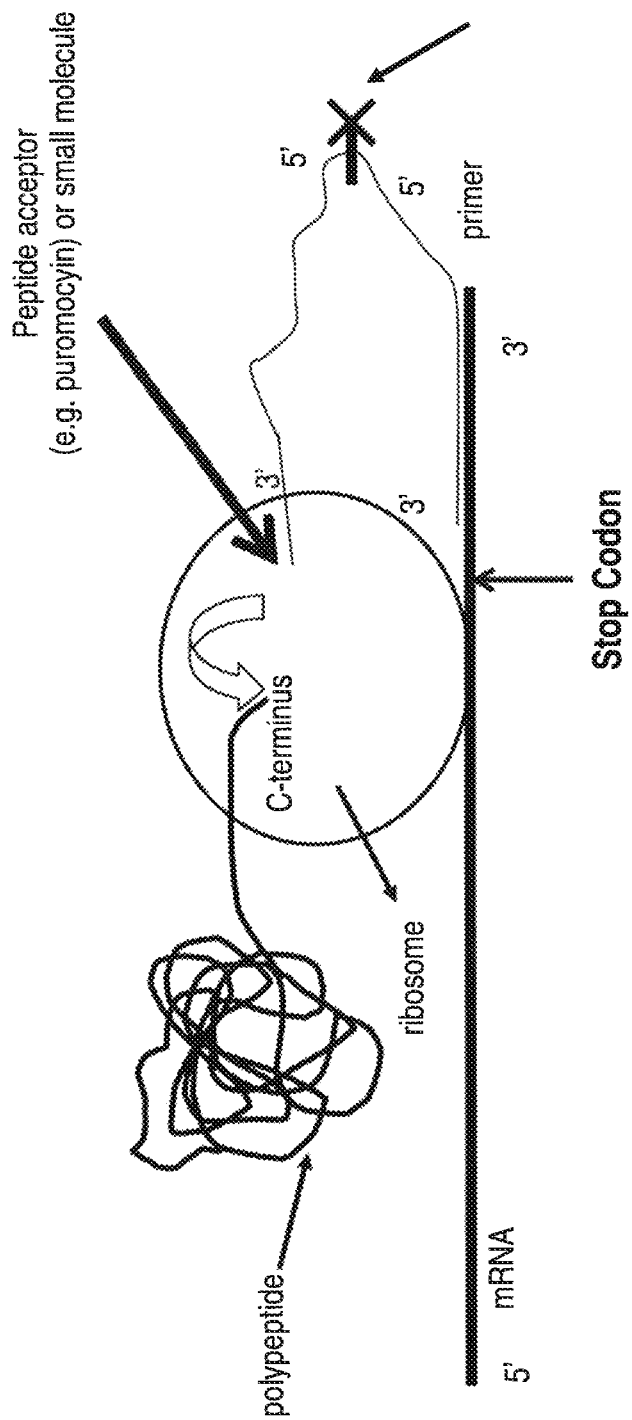
FIG. 2 illustrates the same using an advanced primer that is an inverted polarity primer with two 3' ends that can conveniently prime a cDNA and carry a puromycin or derivative or small molecule on the opposite end
Figure 3:
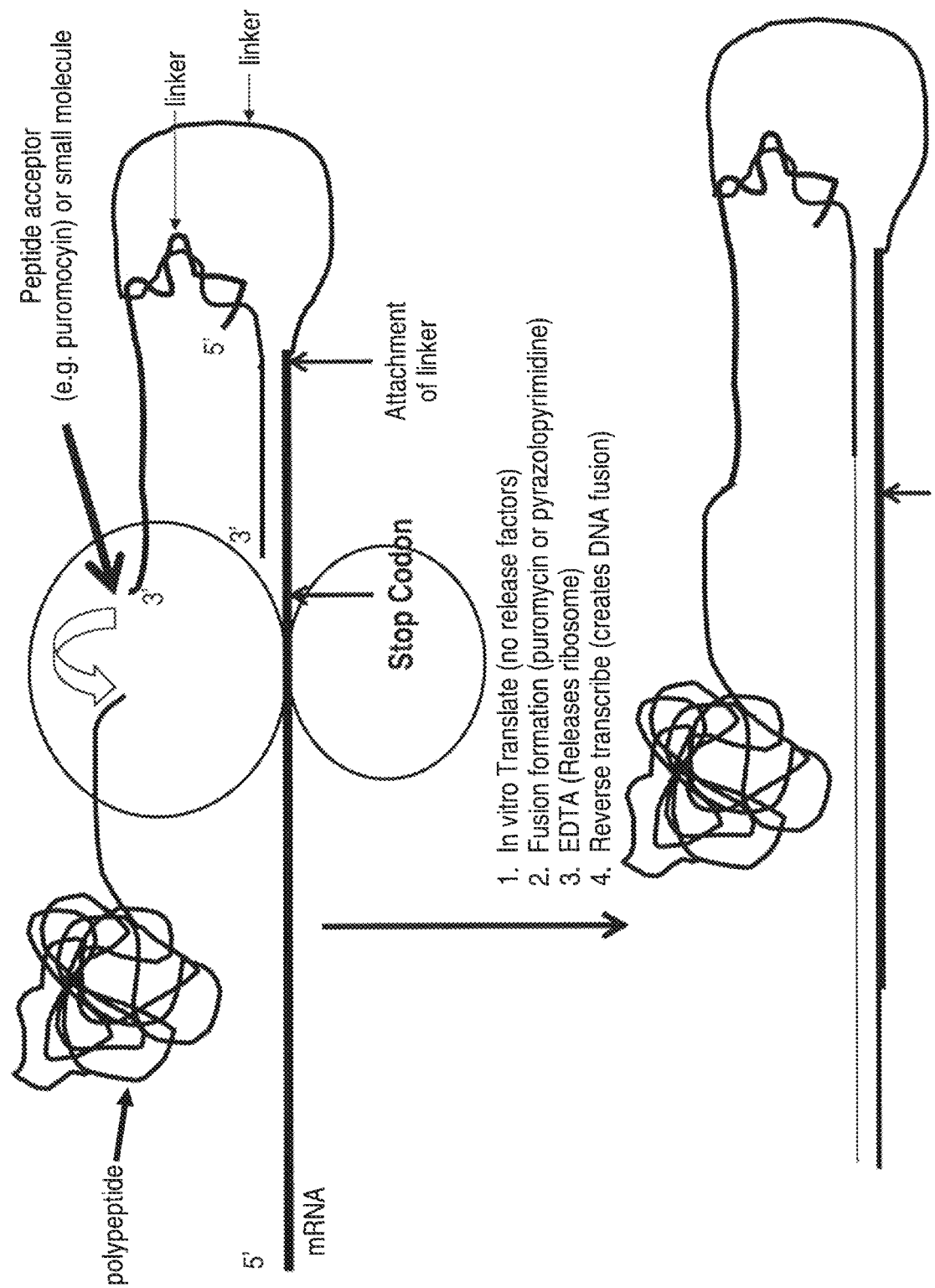
FIG. 3 illustrates the same using an advanced primer that is a stem loop variety and can double back and conveniently prime a cDNA.

An additional embodiment comprises an encoding nucleic acid operably linked to a NA linker that carries a reverse polarity nucleic acid portion at its "5' end" (in quotes, as it effectively has a 3' polarity to direct polymerization), such that it can serve as a primer for polymerization on the encoding nucleic acid template, in addition to its ability to bind, via a stem loop structure, to an NA linker that carries a puromycin or related analogue or small molecule on its 3' end (see FIGS. 2 and 3).

Figure 5:
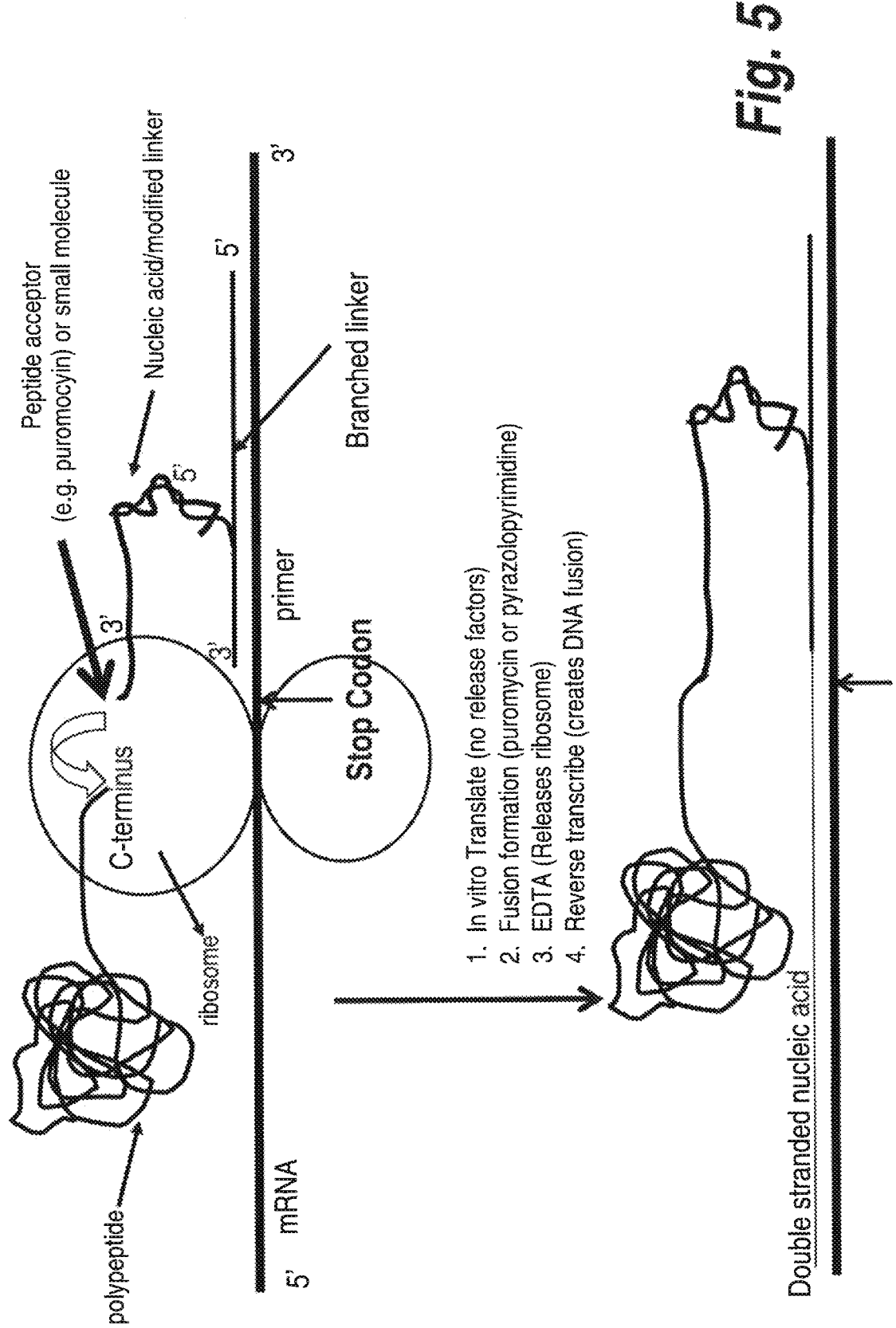
FIG. 5 illustrates one embodiment of the methodology of in vitro display using a branched oligonucleotide linker and a complementary oligonucleotide comprising a covalently attached peptide acceptor

In some embodiments, the encoding nucleic acid is operably linked to a branched NA linker, wherein a portion of the NA liner is complementary to the 3' end of the encoding nucleic acid (see FIG. 5). Any art recognized means of generating a branched NA linker are contemplated. The branch point can occur at any location within the NA linker. Such branched NA linkers can also serve as primers for reverse transcription of the encoding nucleic acid, e.g., an mRNA, to which they are bound.

Figure 6:
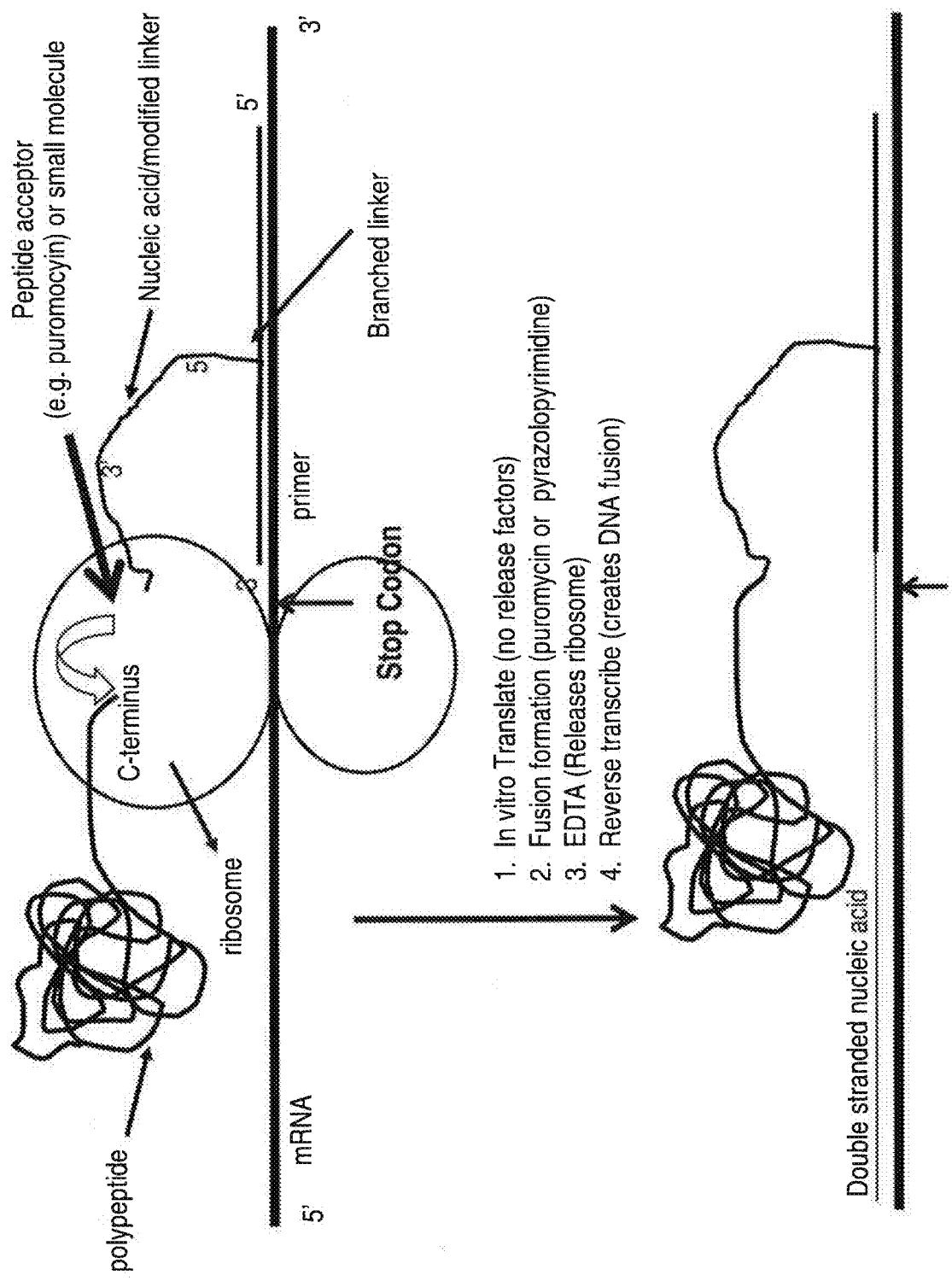
FIG. 6 illustrates one embodiment of the methodology of in vitro display using a branched oligonucleotide linker, covalently attached to a peptide acceptor
Figure 7:
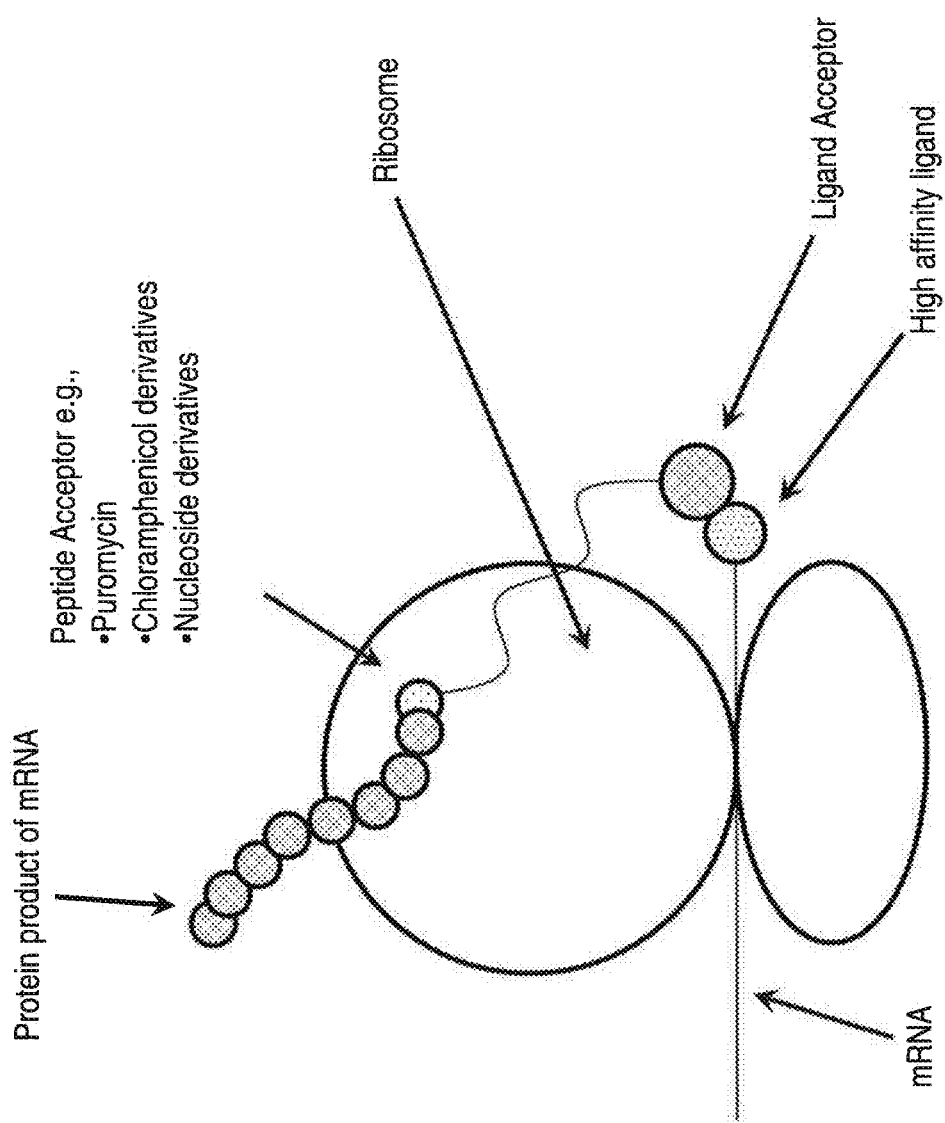
FIG. 7 illustrates one embodiment of the methodology of in vitro display using high affinity ligands and ligand acceptors.

In some embodiments, the encoding nucleic acid is operably linked to a branched NA linker, wherein the linker is covalently attached to a peptide acceptor (see FIG. 6).

In some embodiments, the NA linker comprises locked nucleic acids (LNA) e.g., bicyclic nucleic acids where a ribonucleoside is linked between the 2'-oxygen and the 4'-carbon atoms with a methylene unit. In a particular embodiment, the region of the NA linker that is complementary to the encoding nucleic acid comprises LNA, at least in part, to increase nucleic acid duplex stability (see Kaur et al. (2006). *Biochemistry* 45 (23): 7347-55.

Ligand/Acceptor Linkage

In another aspect, the X-display complex (e.g., the encoding nucleic acid and the encoded polypeptide) is formed through the high affinity or covalent binding of a high affinity ligand to its cognate binding partner (ligand acceptor). In such embodiments, a nucleic acid may be linked covalently or noncovalently to a high affinity ligand, which in-turn binds to a ligand acceptor noncovalently or covalently. In preferred embodiments the interaction is noncovalent. In some embodiments the ligand acceptor is further associated with a second high affinity ligand, which in turn is linked to a peptide acceptor.

Non-limiting examples of high affinity ligand/ligand acceptor pairs include, but are not limited to, FK506/FKBP12, methotrexate/dihydrofolate reductase, and PPI-2458/methionine aminopeptidase 2. Additional non-limiting examples of ligand/ligand acceptor pairs are shown in Table 1. In some embodiments, the ligand/ligand acceptor pair is biotin/streptavidin. Any form of streptavidin is considered for use in the methods of the invention including, but not limited to, monomeric strepavidin, dimeric strepavidin, tetrameric strepavidin, and chemically or genetically modified variants thereof. In some embodiments, the ligand acceptor is tetrameric strepavidin. In a particular embodiment, the tetrameric strepavidin is chemically cross-linked to increase stability.

TABLE 1

| Non-limiting examples of high affinity ligand/ligand acceptor pairs | | | | | |
| --- | --- | --- | --- | --- | --- |
| High Affinity Ligand | Ligand size | Ligand Acceptor | Acceptor Size | $K_d$ or $K_i$ | Reference |
| Biotin | Small molecule | Streptavidin tetramer | 53 kDa | 1-20 fM | |
| Hirudin | 65 aa peptide | Thrombin | 36 kDa | 20 fM | |
| ZFV$^p$(O)F | tripeptide | carboxypeptidase | | 10-27 fM | Biochemistry 1991, 30: 8165-70 |
| Fluorescein-biotin | | Monovalent Ab | | 48 fM | PNAS 2000, 97: 10701-5 |
| ABD (albumin binding domain) | 46 aa | HSA (albumin) | | 50-500 fM | Prot. Eng. Des. Select. 2008, 21: 515-27 |
| 18 bp DNA | | Zn finger | 6 Zn finger domains | 2 fM | PNAS 1998, 95: 2812-17 |
| RNAse A | 13 kDa | hRI (RNase inhibitor) | 50 kDa | 290 aM-1 fM | JMB 2007, 368: 434-449 |
| Cloroalkanes | | Mutated haloalkane dehalogenase, HaloTag | Promega | irreversible | ACS Chem. Bio 2008, 3: 373-82 |
| Inhibitors Aryl (beta-amino ethyl) ketones | Small molecules | Sortase | | irreversible | JBC 2007, 282: 23129 Identification of sortase gene U.S. Pat. No. 7,101,692 |
| Protein A | Antibody Fc domain | | | 1 fM | |

In some embodiments, the high affinity ligand is covalently linked to the nucleic acid (ligand/nucleic acid molecule). Any art recognized method of linking the high affinity ligand to the nucleic acid is contemplated. In one embodiment, the high affinity ligand is covalently linked to 3' end of an mRNA molecule.

Figure 8:
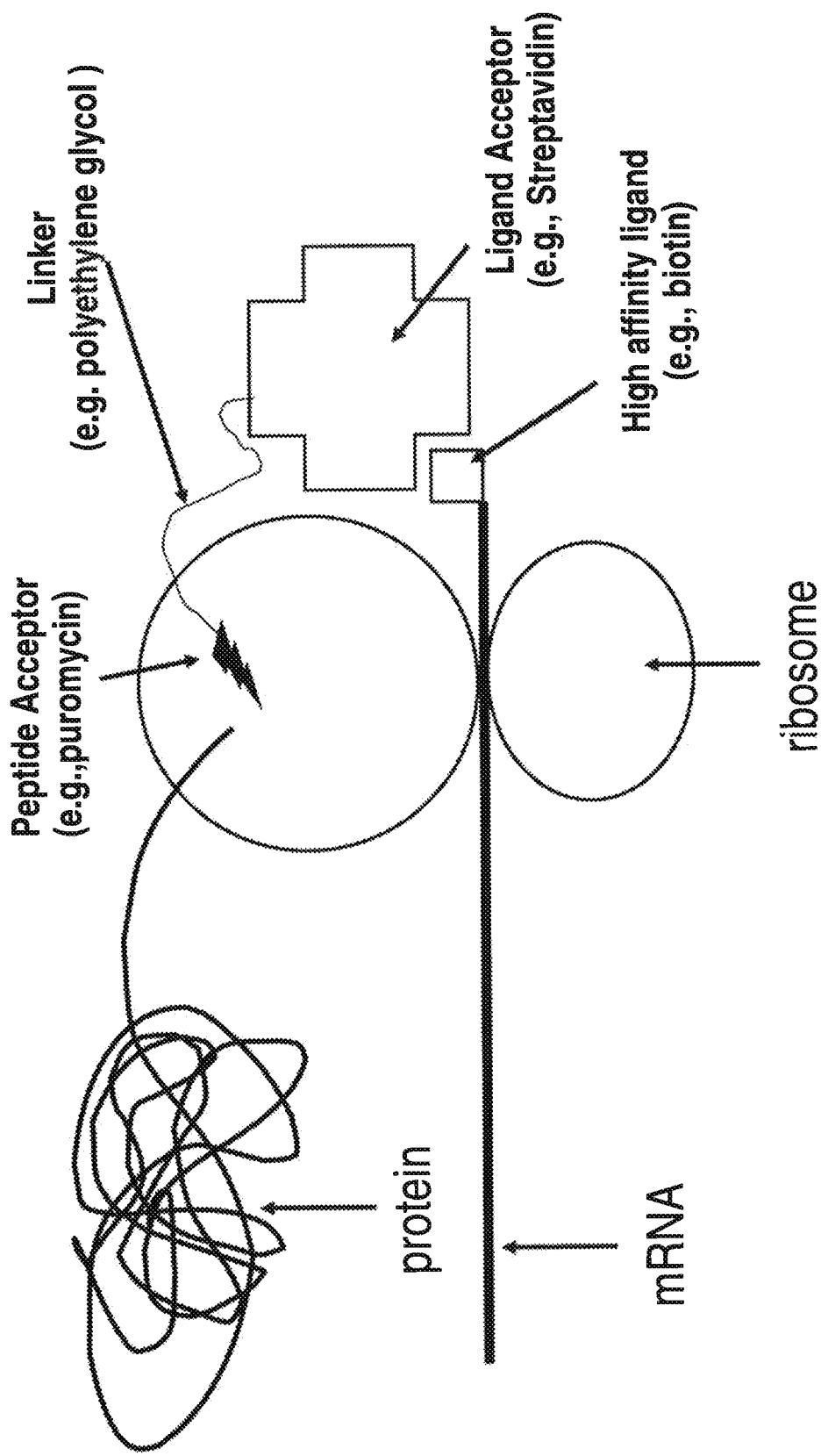
FIG. 8 illustrates one embodiment of the methodology of in vitro display using high affinity ligands and ligand acceptors, wherein the ligand acceptor is covalently linked to a peptide acceptor.

In some embodiments, the high affinity ligand acceptor molecule is covalently linked to a peptide acceptor, which in turn, can become covalently linked to a translated protein by the peptidyl transferase activity of a ribosome (see FIG. 8). The linkage of the high affinity ligand acceptor to the peptide acceptor can be direct or via a linker molecule. Any art recognized linker molecules are contemplated for use in the methods of the invention. In one embodiment, the high affinity ligand acceptor is linked to the peptide acceptor using a polyethylene glycol linker molecule.

Figure 9:
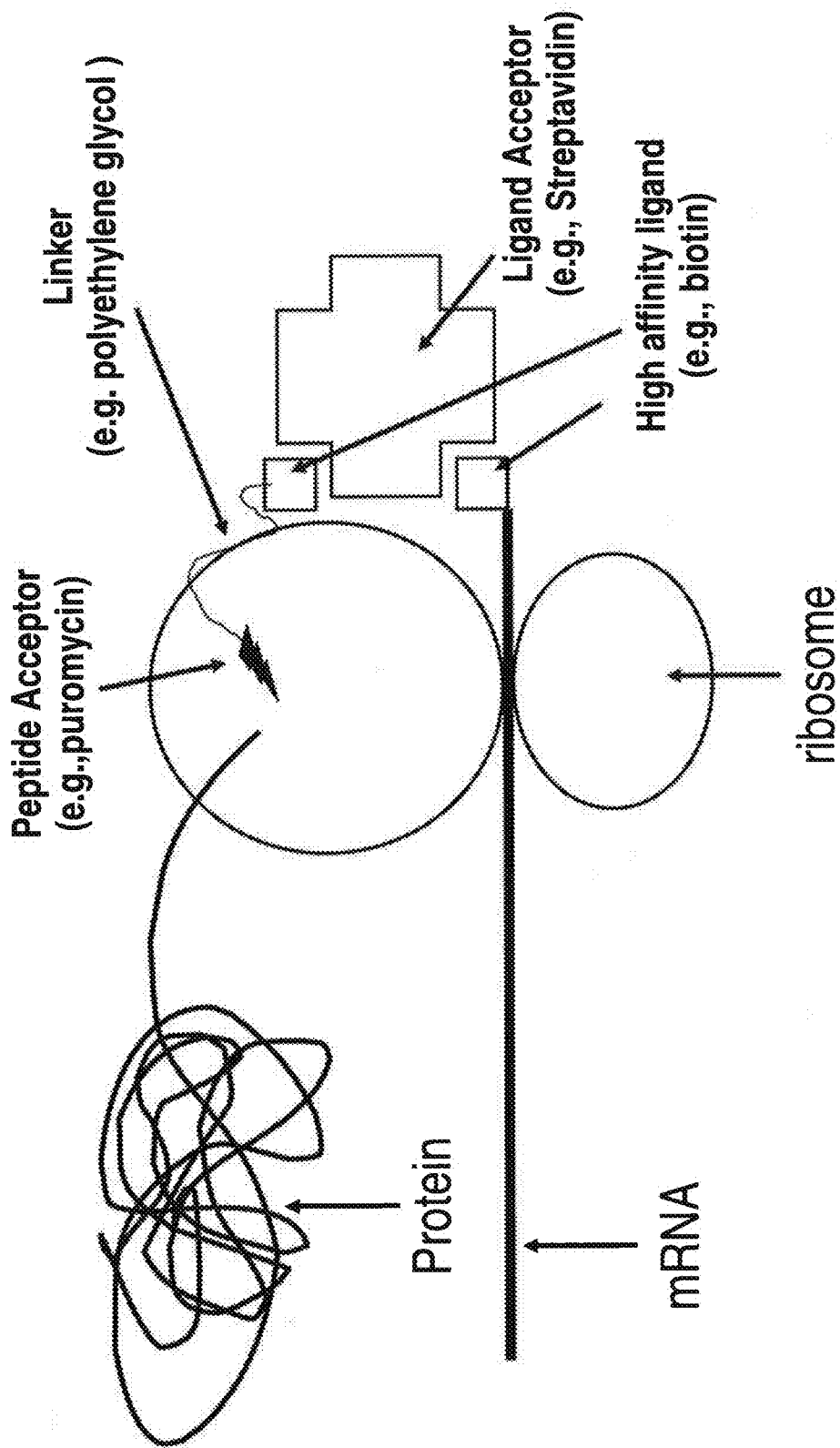
FIG. 9 illustrates one embodiment of the methodology of in vitro display using high affinity ligands and ligand acceptors, wherein the ligand acceptor is non-covalently linked to a peptide acceptor.

In some embodiments, the high affinity ligand is covalently linked to a peptide acceptor, which in turn, can become covalently linked to a translated protein by the peptidyl transferase activity of a ribosome (see FIG. 9). In some preferred embodiments, such ligand/peptide acceptor molecules can be non-covalently linked to a ligand/nucleic acid molecule through a multimeric ligand acceptor, e.g., tetrameric strepavidin. The covalent linkage of the high affinity ligand to the peptide acceptor can be direct or via a linker molecule. Any art recognized linkers are contemplated for use in the methods of the invention. In a particular embodiment, the high affinity ligand is linked to the peptide acceptor using a polyethylene glycol linker molecule.

Figure 4:
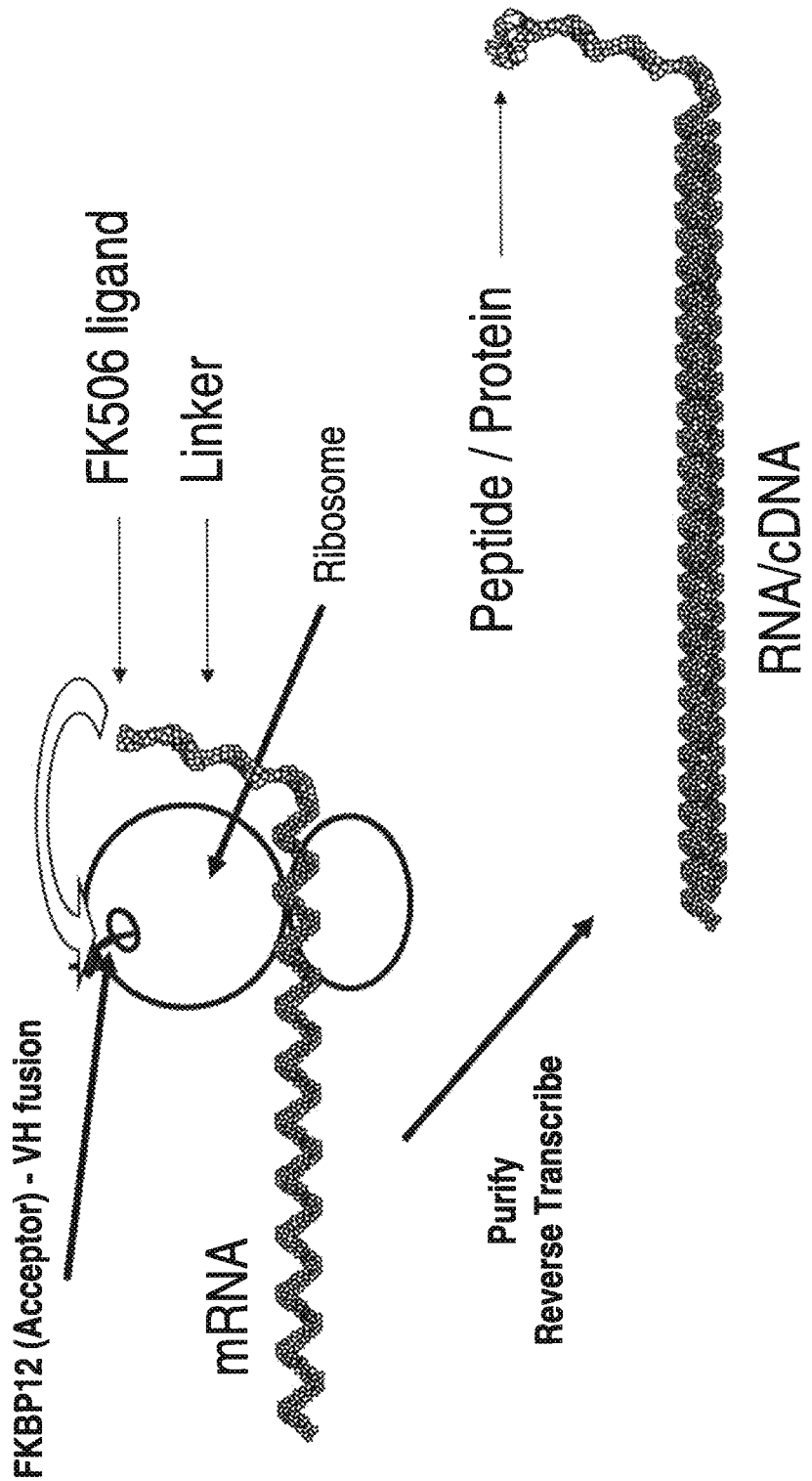
FIG. 4 illustrates one embodiment of the methodology being employed to improve or evolve the structure/function of an antibody heavy chain variable region wherein the polypeptide is fused to an FK12BP protein that can non covalently bind to the nucleic acid linked FK506 small molecule thereby linking an improved (evolved) phenotype (polypeptide) with its encoding genotype (nucleic acid).
Figure 10:
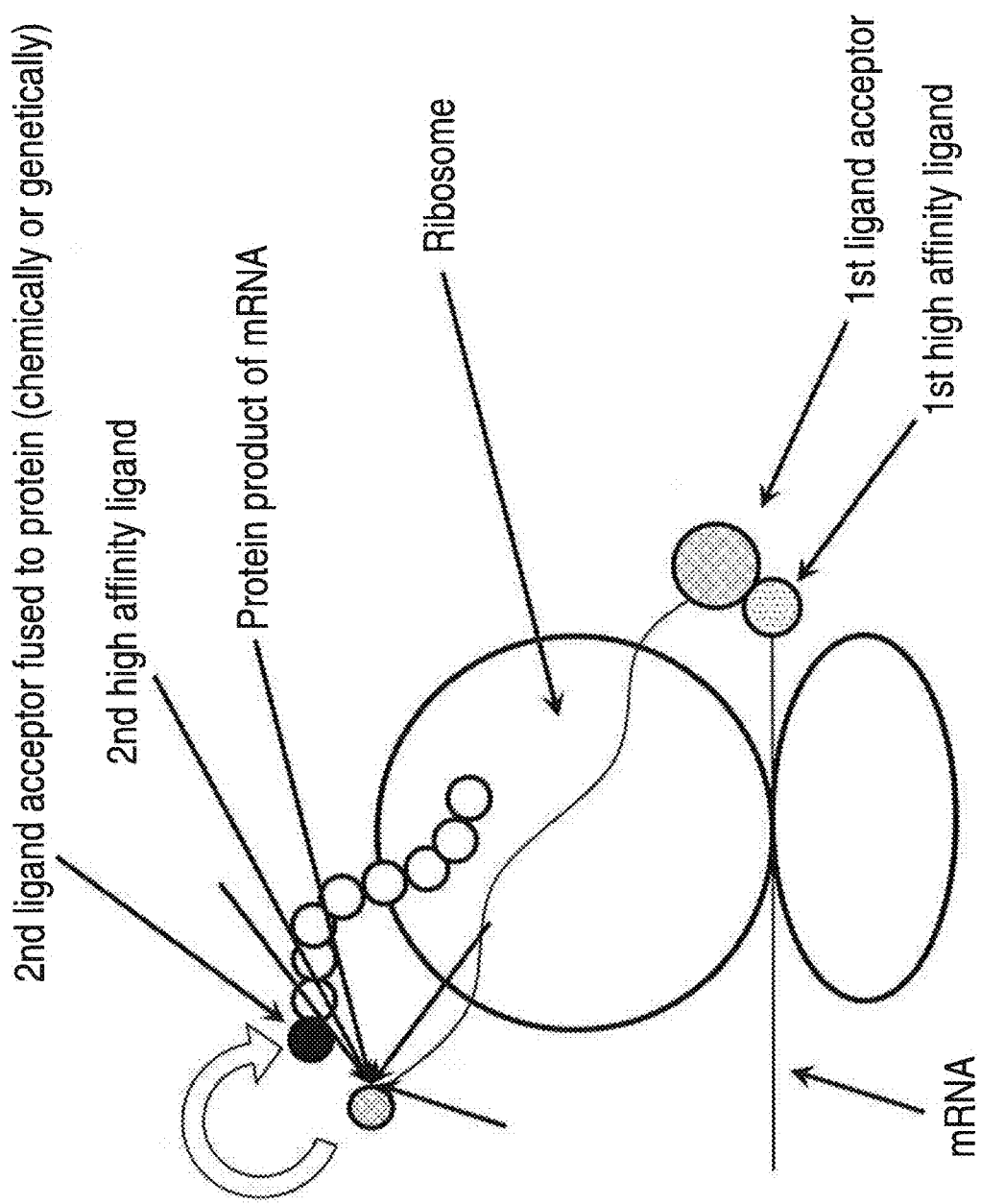
FIG. 10 illustrates one embodiment of the methodology of in vitro display using high affinity ligands and ligand acceptors, wherein a first ligand acceptor molecule is covalently linked to a second (non-cognate) high affinity ligand, wherein the first ligand acceptor molecule can bind to a cognate first high affinity ligand covalently linked to a nucleic acid, and wherein the second high affinity ligand can bind to a cognate second ligand acceptor fused to the polypeptide encoded by the nucleic acid.
Figure 11:
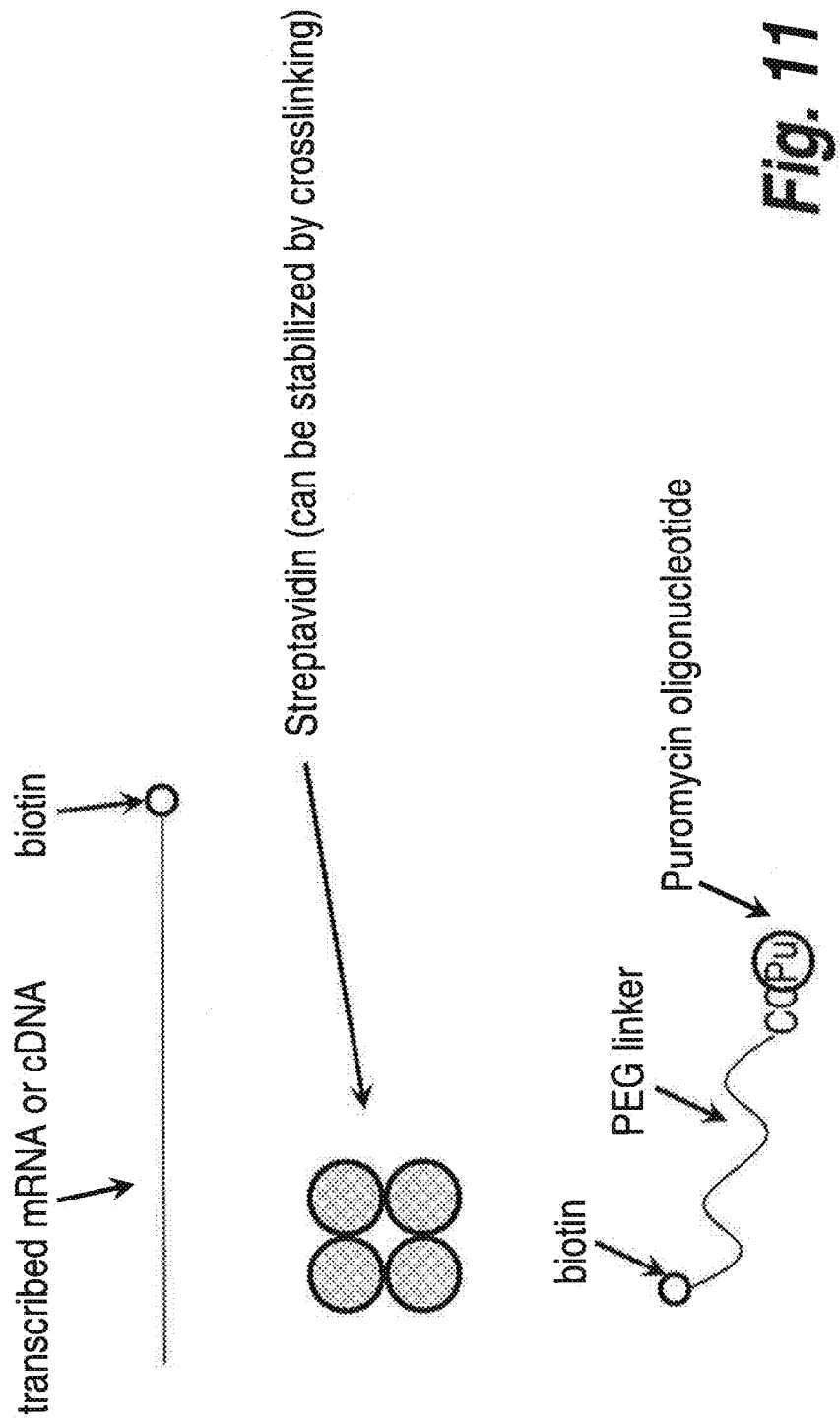
FIG. 11 illustrates a non-limiting example of the individual components used in one embodiment of the methodology of in vitro display using high affinity ligands and ligand acceptors.
Figure 12:
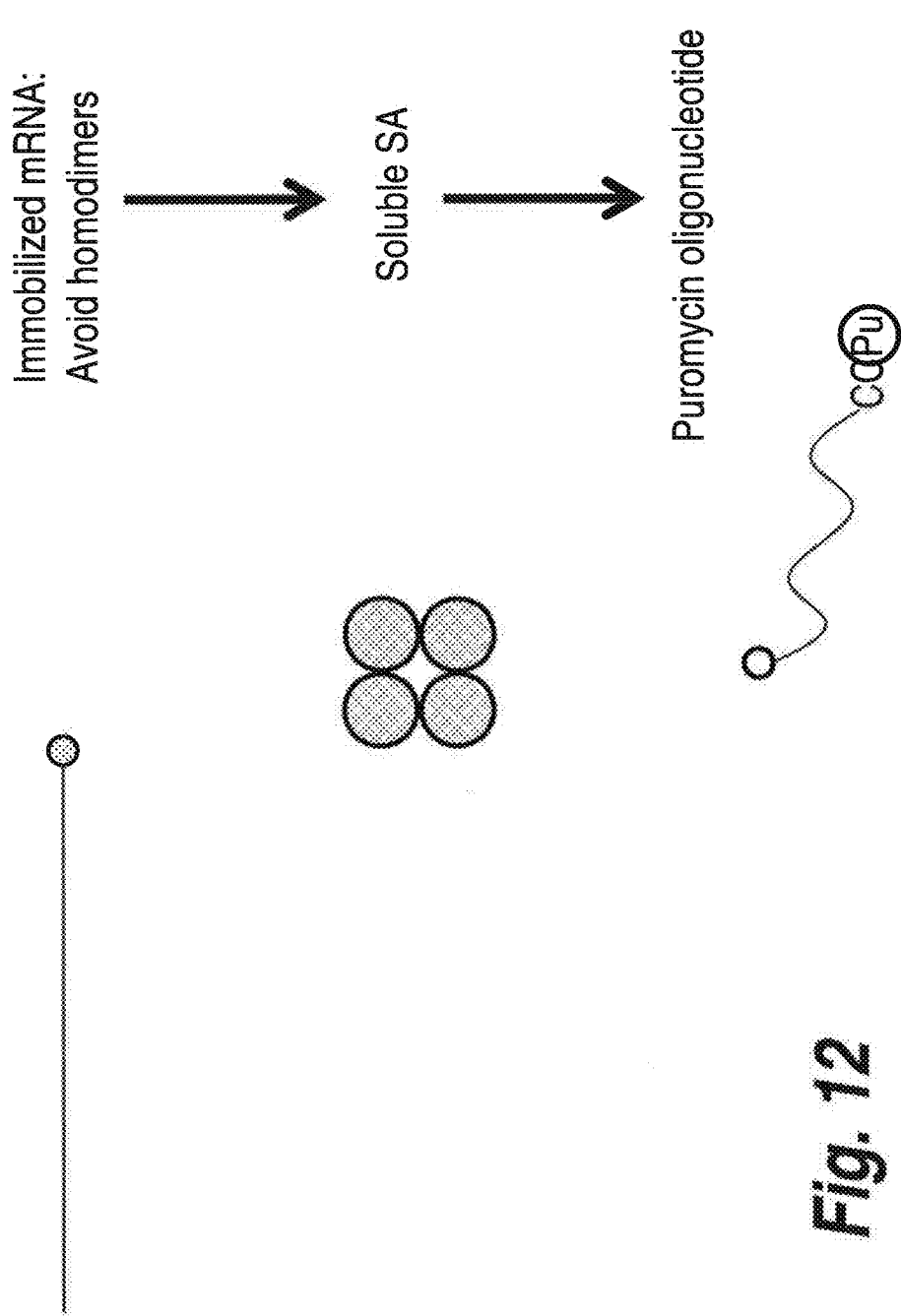
FIG. 12 illustrates a non-limiting assembly order of nucleic/protein complexes for one embodiment of the methodology of in vitro display using high affinity ligands and ligand acceptors.

In some embodiments, the ligand acceptor molecule is fused to the polypeptide encoded by the nucleic acid (see FIGS. 4 and 10). Such fusion can be performed chemically, using chemical crosslinkers or genetically. The ligand acceptor molecule can be fused to the encoded polypeptide at any region. In a particular embodiment, the ligand acceptor molecule is genetically fused to the N terminal region of the encoded polypeptide.

In some embodiments, a first ligand acceptor molecule is covalently linked to a second (non-cognate) high affinity ligand. In such embodiments the first ligand acceptor molecule may bind to a cognate first high affinity ligand which is covalently linked to a nucleic acid. The second high affinity ligand may bind to a cognate second ligand acceptor which is fused to the polypeptide encoded by the nucleic acid.

In a preferred embodiment, a ligand acceptor molecule, preferably a multivalent ligand acceptor (e.g., multivalent streptavidin), binds noncovalently to a first high affinity ligand (e.g., biotin), which is covalently linked to a nucleic acid that is complementary to an mRNA molecule. The multivalent ligand acceptor also binds noncovalently to a second high affinity ligand (e.g., biotin), which is covalently linked to peptide acceptor (e.g., puromycin). The second high affinity ligand may be connected to the peptide acceptor directly or via a linker (as described below, e.g., polyethylene glycol). In preferred embodiments the nucleic acid attached to the first high affinity ligand is complementary to the 3' end of the mRNA. The nucleic acid (e.g., a nucleic acid in an NA linker) should be at least long enough to stably bind to the protein encoding nucleic acid (e.g., mRNA) of the X-display complex. In some embodiments the nucleic acid attached to the first high affinity ligand is between 15 and 100 nucleotides in length, between 15 and 80 nucleotides in length, between 15 and 50 nucleotides in length, between 5 and 40 nucleotides in length, between 15 and 30 nucleotides in length, between 15 and 20 nucleotides in length, between 10 and 20 nucleotides in length, or between 15 and 18 nucleotides in length. In some embodiments the nucleic acid attached to the first high affinity ligand is 15 nucleotides in length, 18, nucleotides in length, 20 nucleotides in length, 30 nucleotides in length, 50 nucleotides in length, 70 nucleotides in length, 80 nucleotides in length, or 87 nucleotides in length.

Several embodiments of the present invention include a method of stably linking an mRNA or modified mRNA, a NA linker operably linked to a puromycin or analogue or a small molecule, and a polypeptide encoded by the mRNA together to form a linked mRNA-polypeptide complex.

In a preferred embodiment, the NA linker is used as a primer to polymerize a second strand of nucleic acid on the mRNA-polypeptide complex to form a nucleic acid duplex linked to the polypeptide. In a preferred embodiment, the polymerization is reverse transcription to form a DNA (or modified DNA) hybrid.

Several embodiments of the present invention include methods of comprising a plurality of distinct X-display complexes, providing a ligand with a desired binding characteristic, contacting the complexes with the ligand, removing unbound complexes, and recovering complexes bound to the ligand.

Several methods of the current invention involve the evolution of nucleic acid molecules and/or proteins. In one embodiment, this invention comprises amplifying the nucleic acid component of the recovered complexes and introducing variation to the sequence of the nucleic acids. In other embodiments, the method further comprises translating polypeptides from the amplified and varied nucleic acids, linking them together using the nucleic acid/modified linkers, and contacting them with the ligand to select another new population of bound complexes. Several embodiments of the present invention use selected protein-mRNA complexes in a process of in vitro evolution, especially the iterative process in which the selected mRNA is reproduced with variation, translated and again connected to cognate protein for selection.

Linker Moieties

In some embodiments, the present invention employs one or more linker moieties (separate from the NA linker described above). In some embodiments linker moieties may be employed to connect a nucleic acid to a peptide acceptor. In other embodiments linker moieties may be used to connect a high affinity ligand (e.g., biotin) or a ligand acceptor (e.g., streptavidin) to a peptide acceptor. In another embodiment, linker moieties may be used to connect a nucleic acid to a high affinity ligand. As used herein, the term "linker moieties" may include one or more linker moieties or subunits.

In some preferred embodiments the linker moieties are poly(alkylene oxide) moieties, which are a genus of compounds having a polyether backbone. Poly(alkylene oxide) species of use in the present invention may include, for example, straight- and branched-chain species. For example, poly(ethylene glycol) is a poly(alkylene oxide) consisting of repeating ethylene oxide subunits, which may or may not include additional reactive, activatable or inert moieties at either terminus. Derivatives of straight-chain poly(alkylene oxide) species that are heterobifunctional are also known in the art. In some embodiments the linker moiety may be composed of 5 to 50 subunits of poly(alkylene oxide), 10 to 30 subunits of poly(alkylene oxide), 10 to 20 units of poly(alkylene oxide), 15 to 20 units of poly(alkylene oxide), or, in some embodiments, 18 subunits of poly(alkylene oxide). One of skill in the art will appreciate that any number of linker moieties may be used as long as it is still possible for the X-display complex to form.

A poly(ethylene glycol) linker is a moiety having a poly(ethylene glycol) ("PEG") backbone or methoxy-PEG ("mPEG") backbone, including PEG and mPEG derivatives. A wide variety of PEG and mPEG derivatives are known in the art and are commercially available. For example, Nektar, Inc. Huntsville, Ala., provides PEG and mPEG compounds useful as linkers or modifying groups optionally having nucleophilic reactive groups, carboxyl reactive groups, eletrophilically activated groups (e.g. active esters, nitrophenyl carbonates, isocyanates, etc.), sulfhydryl selective groups (e.g. maleimide), and heterofunctional (having two reactive groups at both ends of the PEG or mPEG), biotin groups, vinyl reactive groups, silane groups, phospholipid groups, and the like.

In other embodiments the linker moieties may be nucleic acids or any other linker recognized in the art. For example, Polysialic acids (PSAs) and PSA derivatives may be employed (see U.S. Pat. No. 5,846,951, U.S. Pat. Pub. No. US20080262209 and PCT App. WO2005/016973 and WO-A-01879221, which are all incorporated herein by reference in their entirety.)

Although a preferred peptide acceptor is puromycin, other compounds that act in a manner similar to puromycin may be used. Other possible choices for protein acceptors include pyrazolopyrimidine or any related derivatives and tRNA-like structures, and other compounds known in the art. Such compounds include, without limitation, any compound which possesses an amino acid linked to an adenine or an adenine-like compound, such as the amino acid nucleotides, phenylalanyl-adenosine (A-Phe), tyrosyl adenosine (A-Tyr), and alanyl adenosine (A-Ala), as well as amide-linked structures, such as phenylalanyl 3' deoxy 3' amino adenosine, alanyl 3' deoxy 3' amino adenosine, and tyrosyl 3' deoxy 3' amino adenosine; in any of these compounds, any of the naturally-occurring L-amino acids or their analogs may be utilized. In addition, a combined tRNA-like 3' structure-puromycin conjugate may also be used in the invention.

Translation Systems

Several embodiments of the invention utilize preferred methods wherein the mRNA is translated in an in vitro translation system that lacks release factors. Thereby, the ribosome stalls at the stop codon, allowing time for the puromycin or analogue or a small molecule to bind covalently or with high affinity to the polypeptide protein.

In some embodiments of the invention the mRNA is translated in an in vitro translation system in which the function of at least one release factors is inhibited by release factor inhibitors. Suitable inhibitors include, but are not limited to, anti-release factor antibodies, As the method is preferably carried out using in vitro translation systems, it is known in the art that modified amino acids can be incorporated into the translation machinery to create polypeptides with chemical modifications.

A variety of in vitro translation systems may be used such as a reticulocyte lysate system, wheat germ extract system, or other suitable in vitro transcription system. In one preferred embodiment the PURESystem (cosmobio.co.jp/export_e/products/proteins/products_PGM_20060907_06.asp) is employed. The cell-free continuous-flow (CFCF) translation system of Spirin et al. (1988) Science 242: 1162 may be used to increase total yield of library members, or for convenience of use, if desired. A static in vitro protein synthesis system can be used. In this system, protein synthesis generally ceases after 1 h and thus limits the time interval for creation of the library. The advantage of CFCF technology is that high level and long-term synthesis of protein should result in a much larger and more diverse library of protein-RNA complexes. The CFCF technology has been described by Spirin and co-workers as a method for the high-level synthesis of protein over an extended period of time, 24 h or longer. In addition, CFCF technology results in fractionation of the newly-synthesized protein from the translational apparatus, and thus makes it feasible to quickly sequester the protein-nucleic acid complexes. Other applications of CFCF technology include an efficient method for synthesizing peptides. For example, following the identification of a peptide-fusion which binds to a target with high-affinity, the free peptide can be synthesized directly using CFCF technology and used in a binding assay.

Other cell-free techniques for linking a polynucleotide to a polypeptide (i.e., a phenotype) can also be used, e.g., Profusion™ (see, e.g., U.S. Pat. Nos. 6,348,315; 6,261,804; 6,258,558; and 6,214,553 which are incorporated herein by reference).

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate for a particular expression or in vitro translation system. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

In some embodiments expression vectors such as plasmids or viral vectors are not employed, e.g., when the DNA to be expressed exists only in a PCR amplified DNA strand.

In further embodiments, the methods the invention may employ methods and/or compositions described in U.S. Pat. Nos. 7,078,197, 6,429,300, 5,922,545, 7,195,880, 6,416, 950, 6,602,685, 6,623,926, 6,951,725, or in U.S. patent application Ser. Nos. 11/543,316, 10/208,357, which are all incorporated herein by reference in their entirety.

In one preferred embodiment mRNA, containing an intact stop codon and region of 3' untranslated RNA sufficient for binding an oligonucleotide primer, is translated in an in vitro translation system lacking release factors (e.g., PURESystem, cosmobio.co.jp/export_e/products/proteins/products_PGM_20060907_06.asp). Release factors trigger the hydrolysis of the ester bond in peptidyl-tRNA and the release of the newly synthesized protein from the ribosome. In the absence of the release factors, the ribosome will stall on the mRNA. Next a DNA oligonucleotide is added to the mix. This oligonucleotide is complementary to the 3' end of the mRNA and functionalized with a linker which is capable of delivering a peptide acceptor species into the ribosome to form a covalent adduct with the bound translated protein. In some embodiments it is an NA linker which is added. The site of attachment of the linker can be anywhere along the oligonucleotide with the exception of the 3' end. The linker needs to be of sufficient length to reach into the ribosome. The species that forms the adduct is preferably puromycin or pyrazolopyrimidine or any related derivatives.

Following the covalent addition of the linker to the nascent protein, EDTA is added to release the ribosomes, the mRNA-oligonucleotide-protein species is subsequently isolated, and subjected to reverse transcription to create the DNA-protein fusion. Finally, the second strand of DNA is added using any DNA polymerase. In such an embodiment, although the mRNA-oligonucleotide (e.g., NA linker) species may be covalently attached, the NA linker is not required to be covalently attached to any intermediary species in the X-display complex (e.g., if biotin/streptavidin is used to bridge the mRNA to the protein).

The resulting DNA-protein fusion can be used for in vivo or in vitro screening or for diagnostic applications.

Uses

The methods and compositions of the present invention have commercial applications in any area where protein technology is used to solve therapeutic, diagnostic, or industrial problems. This X-display technology is useful for improving or altering existing proteins as well as for isolating new proteins with desired functions. These proteins may be naturally-occurring sequences, may be altered forms of naturally-occurring sequences, or may be partly or fully synthetic sequences.

The methods of the invention can be used to develop or improve polypeptides such as immunobinders, for example, antibodies, binding fragments or analogs thereof, single chain antibodies, catalytic antibodies, VL and/or VH regions, Fab fragments, Fv fragments, Fab' fragments, Dabs, and the like. In some embodiments, the polypeptides to be improved may be any polypeptide having an immunoglobulin or immunoglobulin-like domain, for example Interferons, Protein A, Ankyrins, A-domains, T-cell receptors, Fibronectin III, gamma-Crystallin, antigen binding domains of MHC class molecules (e.g., the alpha and beta antigen binding domains of CD8), Ubiquitin, members of the immunoglobulin superfamily, and many others, as reviewed in Binz, A. et al. (2005) Nature Biotechnology 23:1257 and Barclay (2003) Semin Immunol. 15(4):215-223, which are incorporated herein by reference. In some embodiments, like immunoglobulin libraries derived from the human immune repertoire, a single library uses many different V-region sequences as scaffolds, but they all share the basic immunoglobulin fold. In some embodiments, the immunoglobulin or immunoglobulin-like fold is a barrel shaped protein structure comprising two β-sheets comprising several (e.g., seven in the case of a light chain C-domain of an IgG) anti-parallel β-strands held together by a disulfide bond. Accordingly, the improvement or selection of any immunoglobulin or immunoglobulin-like protein, including portions or fragments thereof, is contemplated.

In another application, the X-display technology described herein is useful for the isolation of proteins with specific binding (for example, ligand binding) properties which may or may not have and immunoglobulin or immunoglobulin-like domain. Proteins exhibiting highly specific binding interactions may be used as non-antibody recognition reagents, allowing X-Display technology to circumvent traditional monoclonal antibody technology. Antibody-type reagents isolated by this method may be used in any area where traditional antibodies are utilized, including diagnostic and therapeutic applications.

In preferred embodiments, the methods will target the improvement of immunobinders, for example, regions of the variable region and/or CDRs of an antibody molecule, i.e., the structure responsible for antigen binding activity which is made up of variable regions of two chains, one from the heavy chain (VH) and one from the light chain (VL). Once the desired antigen-binding characteristics are identified, the variable region(s) can be engineered into an appropriate antibody class such as IgG, IgM, IgA, IgD, or IgE. It is understood that the methods may be employed to improve and/or select human immunobinders and/or immunobinders from other species, e.g., any mammalian or non-mammalian immunobinders, camelid antibodies, shark antibodies, etc.

The present invention may be used to improve human or humanized antibodies (or fragments thereof) for the treatment of any of a number of diseases. In this application, antibody libraries are developed and are screened in vitro, eliminating the need for techniques such as cell-fusion or phage display. In one important application, the invention is useful for improving single chain antibody libraries (Ward et al., Nature 341:544 (1989); and Goulot et al., J. Mol. Biol. 213:617 (1990)). For this application, the variable region may be constructed either from a human source (to minimize possible adverse immune reactions of the recipient) or may contain a totally randomized cassette (to maximize the complexity of the library). To screen for improved antibody molecules, a pool of candidate molecules are tested for binding to a target molecule. Higher levels of stringency are then applied to the binding step as the selection progresses from one round to the next. To increase stringency, conditions such as number of wash steps, concentration of excess competitor, buffer conditions, length of binding reaction time, and choice of immobilization matrix may be altered. Single chain antibodies may be used either directly for therapy or indirectly for the design of standard antibodies. Such antibodies have a number of potential applications, including the isolation of anti-autoimmune antibodies, immune suppression, and in the development of vaccines for viral diseases such as AIDS.

As detailed below, a wide variety of antibody fragment and antibody mimetic technologies have now been developed and are widely known in the art. While a number of these technologies, such as domain antibodies, Nanobodies, and UniBodies make use of fragments of, or other modifications to, traditional antibody structures, there are also alternative technologies, such as Adnectins, Affibodies, DARPins, Anticalins, Avimers, and Versabodies that employ binding structures that, while they mimic traditional antibody binding, are generated from and function via distinct mechanisms. Some of these alternative structures are reviewed in Gill and Damle (2006) 17: 653-658, which incorporated herein by reference. All of the antibody derivatives and builders mentioned above may be improved and/or selected by the methods of the present invention. In some embodiments, methods known in the art to generate Nanobodies, UniBodies, Adnectins, Affibodies, DARPins, Anticalins, Avimers, and Versabodies may be used to discover an initial binding protein which may then serve as the basis for the generation of a library which may be produced and selected from according to the methods of the present invention. Alternatively, builders already known in the art may be used directly to create new libraries for use with the methods described herein.

In some embodiments the methods described herein will target the improvement of Domain Antibodies (dAbs). Domain Antibodies are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, domain antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; U.S. Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

In other embodiments the methods described herein will target the improvement of nanobodies. Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. Nanobodies have a high homology with the VH domains of human antibodies and can be further humanized without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see, e.g., WO 04/041867, which is herein incorporated by reference in its entirety) and are easy to manufacture. Other advantages of Nanobodies include recognizing uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts, e.g., E. coli (see, e.g., U.S. Pat. No. 6,765,087, which is herein incorporated by reference in its entirety), molds (for example Aspergillus or Trichoderma) and yeast (for example Saccharomyces, Kluyveromyces, Hansenula or Pichia) (see, e.g., U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution. Accordingly, the methods of the present invention my be used to improve the affinity of nanobodies for their target molecules.

Methods known in the art may be used to generate nanobodies (or other binders/immunobinders described herein). Such builders may then serve as the basis for the generation of a library which may be produced and selected from according to the methods of the present invention. For example, the Nanoclone method (see, e.g., WO 06/079372, which is herein incorporated by reference in its entirety) is a proprietary method for generating Nanobodies against a desired target, based on automated high-throughout selection of B-cells and could be used in the context of the instant invention. The successful selection of nanobodies from the Nanoclone method may provide an initial set of nanobodies which may be further improved by the methods described herein.

In other embodiments the methods described herein will target the improvement of UniBodies. Unibodies are another antibody fragment technology, however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy. UniBodies are cleared from the body at a similar rate to whole IgG4 antibodies and are able to bind with a similar affinity for their antigens as whole antibodies. Further details of UniBodies may be obtained by reference to patent application WO2007/059782, which is herein incorporated by reference in its entirety.

In other embodiments the methods described herein will target the improvement of fibronectin or adnectin molecules. Adnectin molecules are engineered binding proteins derived from one or more domains of the fibronectin protein (see Ward M., and Marcey, D., callutheran.edu/Academic_Programs/Departments/BioDev/omm/fibro/fibro.htm). Typically, fibronectin is made of three different protein modules, type I, type II, and type III modules. For a review of the structure of function of the fibronectin, see Pankov and Yamada (2002) J Cell Sci.; 115(Pt 20):3861-3, Hohenester and Engel (2002) 21:115-128, and Lucena et al. (2007) Invest Clin. 48:249-262, which are incorporated herein by reference.

Depending on the originating tissue, fibronectin may contain multiple type III domains which may be denoted, e.g., $^1$Fn3, $^2$Fn3, $^3$Fn3, etc. The $^{10}$Fn3 domain contains an integrin binding motif and further contains three loops which connect the beta strands. These loops may be thought of as corresponding to the antigen binding loops of the IgG heavy chain, and they may be altered by the methods discussed herein below to select fibronectin and adnectin molecules that specifically bind a target of interest. Adnectin molecules to be improved may also be derived from polymers of $^{10}$Fn3 related molecules rather than a simple monomeric $^{10}$Fn3 structure.

Although the native $^{10}$Fn3 domain typically binds to integrin, $^{10}$Fn3 proteins adapted to become adnectin molecules are altered so to bind antigens of interest. Accordingly, methods available to the skilled artisan may be used to create $^{10}$Fn3 variant and mutant sequences (thereby forming a library) which is compatible with the methods of the present invention. For example the alterations in the $^{10}$Fn3 may be made by any method known in the art including, but not limited to, error prone PCR, site-directed mutagenesis, DNA shuffling, or other types of recombinational mutagenesis which have been referenced herein. In one example, variants of the DNA encoding the $^{10}$Fn3 sequence may be directly synthesized in vitro. Alternatively, a natural $^{10}$Fn3 sequence may be isolated or cloned from the genome using standard methods (as performed, e.g., in U.S.

Pat. Application No. 20070082365, incorporated herein by reference), and then mutated using mutagenesis methods known in the art.

In one embodiment, a target protein, may be immobilized on a solid support, such as a column resin or a well in a microtiter plate. The target is then contacted with a library of potential binding proteins or X-display complexes as described herein. The library may comprise $^{10}$Fn3 clones or adnectin molecules derived from the wild type $^{10}$Fn3 by mutagenesis/randomization of the $^{10}$Fn3 sequence or by mutagenesis/randomization of the $^{10}$Fn3 loop regions (not the beta strands). The selection/mutagenesis process may be repeated until builders with sufficient affinity to the target are obtained. Adnectin molecules for use in the present invention may be engineered using the PROfusion™ technology employed by Adnexus, a Briston-Myers Squibb company. The PROfusion technology was created based on the techniques referenced above (e.g., Roberts & Szostak (1997) 94:12297-12302). Methods of generating libraries of altered $^{10}$Fn3 domains and selecting appropriate builders which may be used with the present invention are described fully in the following U.S. patent and patent application documents and are incorporated herein by reference: U.S. Pat. Nos. 7,115,396; 6,818,418; 6,537,749; 6,660,473; 7,195,880; 6,416,950; 6,214,553; 6,623,926; 6,312,927; 6,602,685; 6,518,018; 6,207,446; 6,258,558; 6,436,665; 6,281,344; 7,270,950; 6,951,725; 6,846,655; 7,078,197; 6,429,300; 7,125,669; 6,537,749; 6,660,473; and U.S. Pat. Application Nos. 20070082365; 20050255548; 20050038229; 20030143616; 20020182597; 20020177158; 20040086980; 20040253612; 20030022236; 20030013160; 20030027194; 20030013110; 20040259155; 20020182687; 20060270604; 20060246059; 20030100004; 20030143616; and 20020182597. Also see the methods of the following references which are incorporated herein by reference in their entirety: Lipovšek et al. (2007) Journal of Molecular Biology 368: 1024-1041; Sergeeva et al. (2006) Adv Drug Deliv Rev. 58:1622-1654; Petty et al. (2007) Trends Biotechnol. 25: 7-15; Rothe et al. (2006) Expert Opin Biol Ther. 6:177-187; and Hoogenboom (2005) Nat Biotechnol. 23:1105-1116.

Additional molecules which can be improved using the methods of the present invention include, without limitation, human fibronectin modules $^{1}$Fn3-$^{9}$Fn3 and $^{11}$Fn3-$^{17}$Fn3 as well as related Fn3 modules from non-human animals and prokaryotes. In addition, Fn3 modules from other proteins with sequence homology to $^{10}$Fn3, such as tenascins and undulins, may also be used. Other exemplary proteins having immunoglobulin-like folds (but with sequences that are unrelated to the $V_H$ domain) include N-cadherin, ICAM-2, titin, GCSF receptor, cytokine receptor, glycosidase inhibitor, E-cadherin, and antibiotic chromoprotein. Further domains with related structures may be derived from myelin membrane adhesion molecule P0, CD8, CD4, CD2, class I MHC, T-cell antigen receptor, CD1, C2 and I-set domains of VCAM-1, I-set immunoglobulin fold of myosin-binding protein C, I-set immunoglobulin fold of myosin-binding protein H, I-set immunoglobulin-fold of telokin, telikin, NCAM, twitchin, neuroglian, growth hormone receptor, erythropoietin receptor, prolactin receptor, GC-SF receptor, interferon-gamma receptor, beta-galactosidase/glucuronidase, beta-glucuronidase, and transglutaminase. Alternatively, any other protein that includes one or more immunoglobulin-like folds may be utilized to create a adnectin-like binding moiety which may be improved by the methods described herein. Such proteins may be identified, for example, using the program SCOP (Murzin et al., J. Mol. Biol. 247:536 (1995); Lo Conte et al., Nucleic Acids Res. 25:257 (2000).

In other embodiments the methods of the present invention may be employed to improve affibody molecules. Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55). Similar libraries which may be produced by methods known in the art may be selected using the X-display technology described herein. The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

In other embodiments the methods of the present invention may be employed to improve DARPins. DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, ultra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in U.S. Patent Application Publication No. 2004/0132028 and International Patent Application Publication No. WO 02/20565, both of which are hereby incorporated by reference in their entirety.

In other embodiments the methods of the present invention may be employed to improve anticalins. Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Such Anticalin libraries may be employed in accordance with the X-display technology of the present invention. Studies have successfully demonstrated that Anticalins can be developed that are specific for virtually any human target protein can be isolated and binding affinities in the nanomolar or higher range can be obtained.

Anticalins can also be formatted as dual targeting proteins, so-called Duocalin. A Duocalin binds two separate therapeutic targets in one easily produced monomeric protein using standard manufacturing processes while retaining target specificity and affinity regardless of the structural orientation of its two binding domains. Anticalins selected by the methods of the present invention may be assembled into Duocalin molecules.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins. Additional information regarding Anticalins can be found in U.S. Pat. No. 7,250,297 and International Patent Application Publication No. WO 99/16873, both of which are hereby incorporated by reference in their entirety.

In other embodiments the methods of the present invention may be employed to improve Avimers. Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets, and these may be further improved by the methods described herein.

Additional information regarding Avimers can be found in U.S. Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

In other embodiments the methods of the present invention may be employed to improve Versabodies. Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies may be manufactured in *E. coli* at high yields, and because of their hydrophilicity and small size, Versabodies are highly soluble and can be formulated to high concentrations. Versabodies are exceptionally heat stable (they can be boiled) and offer extended shelf-life. All of the qualities of the builders described herein (e.g., heat stability, salt stability, shelf life, immunogenicity, target affinity, etc.) may be improved by the display and selection methods described herein (X-display methods).

Additional information regarding Versabodies can be found in U.S. Patent Application Publication No. 2007/0191272 which is hereby incorporated by reference in its entirety.

In other embodiments the methods of the present invention may be employed to improve SMIP™ molecules. SMIPs™ (Small Modular ImmunoPharmaceuticals-Trubion Pharmaceuticals) engineered to maintain and optimize target binding, effector functions, in vivo half life, and expression levels. SMIPS consist of three distinct modular domains. First they contain a binding domain which may consist of any protein which confers specificity (e.g., cell surface receptors, single chain antibodies, soluble proteins, etc). Secondly, they contain a hinge domain which serves as a flexible linker between the binding domain and the effector domain, and also helps control multimerization of the SMIP drug. Finally, SMIPS contain an effector domain which may be derived from a variety of molecules including Fc domains or other specially designed proteins. The modularity of the design, which allows the simple construction of SMIPs with a variety of different binding, hinge, and effector domains, provides for rapid and customizable drug design. The binding domains of the SMIP™ molecules may also serve as the basis for a library suitable for display and selection according to the methods described herein (e.g., X-display methods).

More information on SMIPs, including examples of how to design them, may be found in Zhao et al. (2007) Blood 110:2569-77 and the following U.S. Pat. App. Nos. 20050238646; 20050202534; 20050202028; 20050202023; 20050202012; 20050186216; 20050180970; and 20050175614.

The detailed description of antibody fragment and antibody mimetic technologies provided above is not intended to be a comprehensive list of all technologies that could be used in the context of the instant specification. For example, and also not by way of limitation, a variety of additional technologies including alternative polypeptide-based technologies, such as fusions of complimentary determining regions as outlined in Qui et al., Nature Biotechnology, 25(8) 921-929 (2007), which is hereby incorporated by reference in its entirety, could be used in the context of the instant invention.

The X-Display complexes (e.g., nucleic acid-protein fusions or DNA-protein fusions) described herein may be used for any application previously described or envisioned for RNA-protein fusions. Commercial uses include the isolation of polypeptides with desired properties through in vitro evolution techniques (see, for example, Szostak et al., U.S. Ser. No. 09/007,005 and U.S. Ser. No. 09/247,190; Szostak et al., WO98/31700; Roberts & Szostak, Proc. Natl. Acad. Sci. USA (1997) vol. 94, p. 12297-12302)), screening of cDNA libraries that are derived from cellular mRNA (see, for example, Lipovsek et al., U.S. Ser. No. 60/096,818, filed Aug. 17, 1998), and the cloning of new genes on the basis of protein-protein interactions (Szostak et al., U.S. Ser. No. 09/007,005 and U.S. Ser. No. 09/247,190; Szostak et al., WO98/31700), as well as the use of these fusions in protein display experiments (Kuimelis et al. U.S. Ser. No. 60/080, 686 and U.S. Ser. No. 09/282,734). The X-Display complexes (e.g., DNA-protein fusions) of the invention may be used for any application previously described or envisioned for previously described display technologies such as those disclosed in U.S. Pat. Nos. 6,416,950; 6,429,300; 6,194,550; 6,207,446; and 6,214,553, which are all incorporated herein by reference in their entirety. These X-Display complexes (e.g., DNA-protein fusions) may be used for any appropriate therapeutic, diagnostic, or research purpose, particularly in the pharmaceutical and agricultural areas.

Isolation of New Catalysts

The present invention may also be used to select new catalytic proteins. In vitro selection and evolution has been used previously for the isolation of novel catalytic RNAs and DNAs, and, in the present invention, is used for the isolation of novel protein enzymes (a non-limiting example, merely provided for illustration, are enzymes suitable for carrying out the metabolism of input polymers into smaller and more immediately useful byproducts, such as for converting polysaccharides into more useful biofuels). In one particular example of this approach, a catalyst may be isolated indirectly by selecting for binding to a chemical analog of the catalyst's transition state. In another particular example, direct isolation may be carried out by selecting for covalent bond formation with a substrate (for example, using a substrate linked to an affinity tag) or by cleavage (for example, by selecting for the ability to break a specific bond and thereby liberate catalytic members of a library from a solid support).

This approach to the isolation of new catalysts has at least two important advantages over catalytic antibody technology (reviewed in Schultz et al., J. Chem. Engng. News 68:26 (1990)). First, in catalytic antibody technology, the initial pool is generally limited to the immunoglobulin fold; in contrast, the starting library of X-display complexes (DNA-protein fusions) may be either completely random or may consist, without limitation, of variants of known enzymatic structures or protein scaffolds. In addition, the isolation of catalytic antibodies generally relies on an initial selection for binding to transition state reaction analogs followed by laborious screening for active antibodies; again, in contrast, direct selection for catalysis is possible using an X-Display library approach, as previously demonstrated using RNA libraries. In an alternative approach to isolating protein enzymes, the transition-state-analog and direct selection approaches may be combined.

Enzymes obtained by this method are highly valuable. For example, there currently exists a pressing need for novel and effective industrial catalysts that allow improved chemical processes to be developed. A major advantage of the invention is that selections may be carried out in arbitrary conditions and are not limited, for example, to in vivo conditions. The invention therefore facilitates the isolation of novel enzymes or improved variants of existing enzymes that can carry out highly specific transformations (and thereby minimize the formation of undesired byproducts) while functioning in predetermined environments, for example, environments of elevated temperature, pressure, or solvent concentration.

An In Vitro Interaction Trap

The X-display technology is also useful for screening cDNA libraries and cloning new genes on the basis of protein-protein interactions. By this method, a cDNA library is generated from a desired source (for example, by the method of Ausubel et al., Current Protocols in Molecular Biology, John Wiley & Sons and Greene Publishing Company, 1994; in particular see Chapter 5). Each of the candidate cDNAs may be formulated into an X-display complex (e.g., a DNA-protein fusion) using the techniques described herein, and the ability of these complexes (or improved versions of the fusions) to interact with particular molecules is then tested.

The fact that the interaction step takes place in vitro allows careful control of the reaction stringency, using nonspecific competitor, temperature, and ionic conditions. Alteration of normal small molecules with non-hydrolyzable analogs (e.g., ATP vs. ATPgS) provides for selections that discriminate between different conformers of the same molecule. This approach is useful for both the cloning and functional identification of many proteins since the nucleic acid sequence of the selected binding partner is associated and may therefore be readily isolated. In addition, the technique is useful for identifying functions and interactions of any human genes.

The method can also be used to develop or improve polypeptide ligands for improved half life, affinity, or solubility. The X-Display complexes (e.g., DNA-protein fusions) described herein may be used in any selection method for desired proteins, including molecular evolution and recognition approaches. Exemplary selection methods are described, for example, in Szostak et al., U.S. Ser. No. 09/007,005 and U.S. Ser. No. 09/247,190; Szostak et al., WO98/31700; Roberts & Szostak, Proc. Natl. Acad. Sci. USA (1997) vol. 94, p. 12297-12302; Lipovsek et al., U.S. Ser. No. 60/096,818 and U.S. Ser. No. 09/374,962; and Kuimelis et al. U.S. Ser. No. 60/080,686 and U.S. Ser. No. 09/282,734, all hereby incorporated by reference.

Library Generation, Screening and Affinity Maturation

In some embodiments peptide or gene libraries may be screened to identify peptides having desired qualities (e.g., binding to a particular antigen) or which have been improved or modified according to the methods of the invention. In related embodiments, a particular peptide produced or selected by the methods described herein may be further altered by affinity maturation or mutagenesis, thereby producing a library of related peptides or nucleic acids. As such, one aspect of the invention may involve screening large libraries in order to identify potential peptides (or nucleic acids encoding said peptides) which have desirable qualities, such as the ability to bind an antigen, a higher binding affinity, etc. Any methods for library generation and target selection known in the art or described herein may be used in accordance with the present invention.

Methods of library generation known in the art, in accordance with the methods described herein (e.g., for adding the appropriate tags, complementary sequences, etc.) may be employed to create libraries suitable for use with the methods described herein. Some methods for library generation are described in U.S. Ser. Nos. 09/007,005 and 09/247,190; Szostak et al., WO989/31700; Roberts & Szostak (1997) 94:12297-12302; U.S. Ser. No. 60/110,549, U.S. Ser. No. 09/459,190, and WO 00/32823, which are incorporated herein by reference.

In one embodiment the library will comprise VH domains, preferably human VH domains. Any cells may be used as a source for a library. In some preferred embodiments the source of cells for the library may be Peripheral Blood Mononuclear Cells (PBMCs), splenocytes, or bone marrow cells (e.g., see FIG. 36 which describes the VH library diversity which may be obtained in a library from certain types of donor cells).

Figure 22:
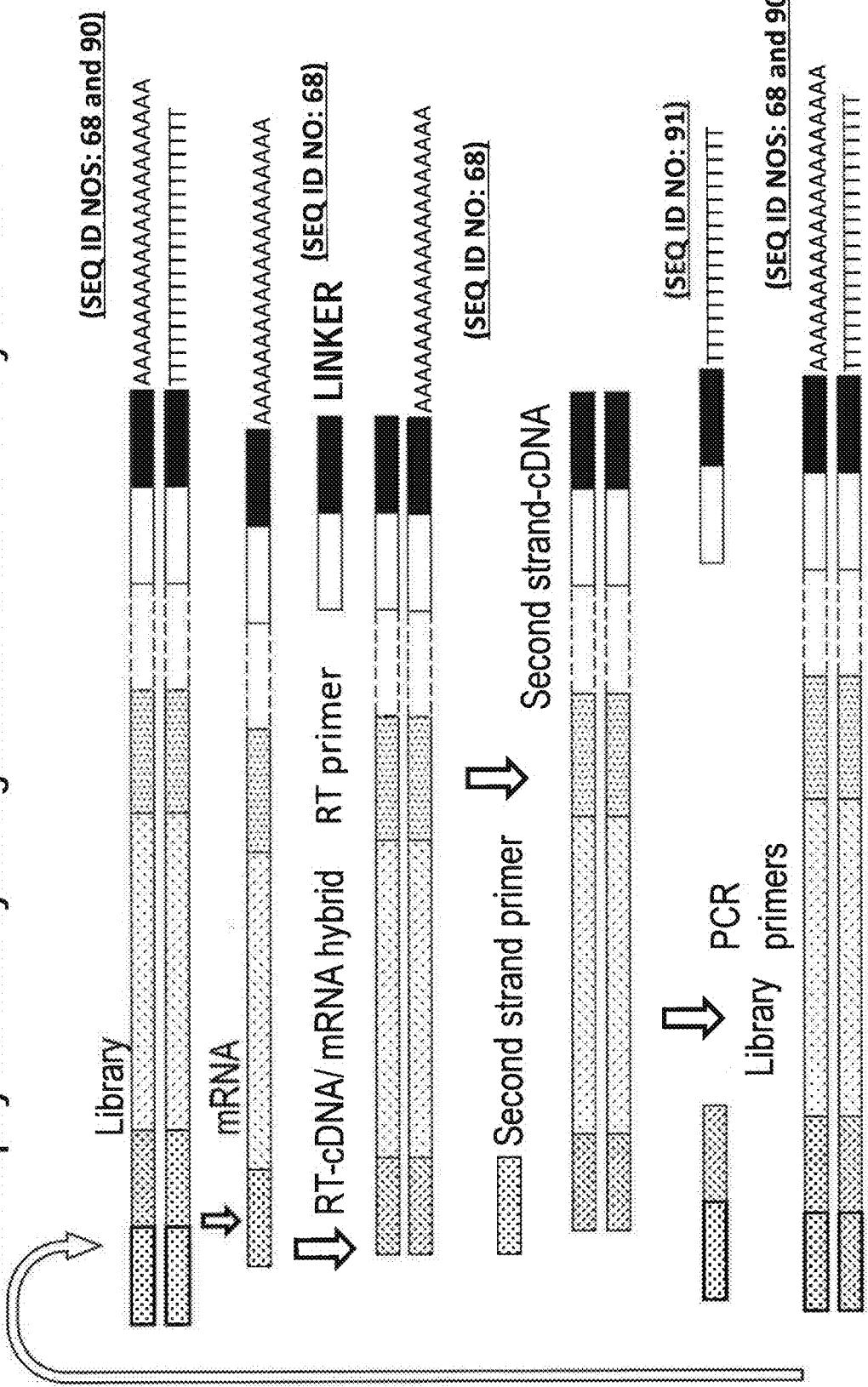
FIG. 22 (SEQ ID NOS: 68, 90 and 91) illustrates the progress of one embodiment of the invention from library through selection, illustrating that the method may be iterative such that nucleic acids/proteins selected in one round may be used to generate a library for subsequent rounds of X-display complex formation and selection.
Figure 23:
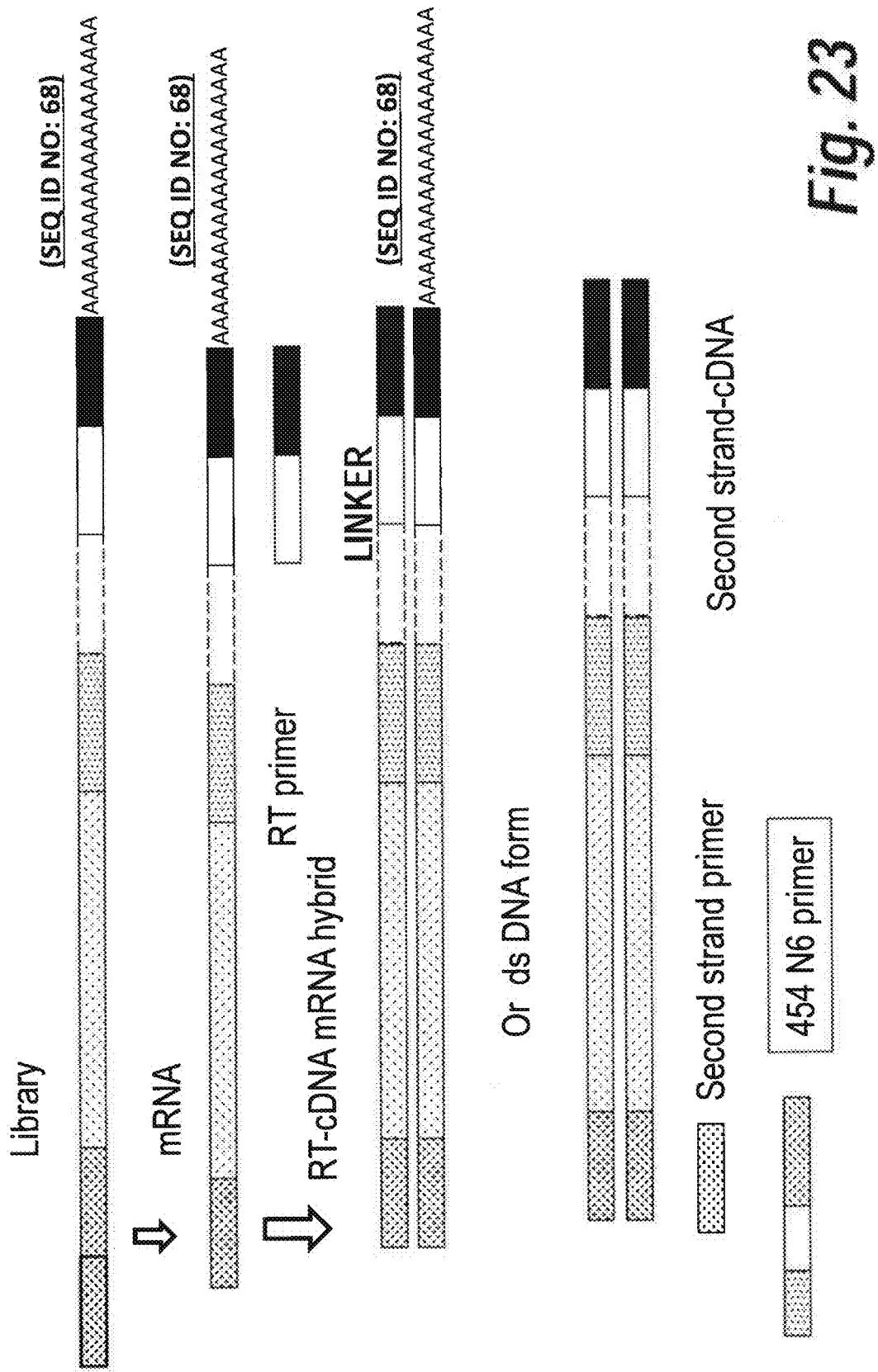
FIG. 23 (SEQ ID NO: 68) illustrates one embodiment of the invention whereby several rounds of selection are employed without regenerating a library or amplifying the selection products.
Figure 24:
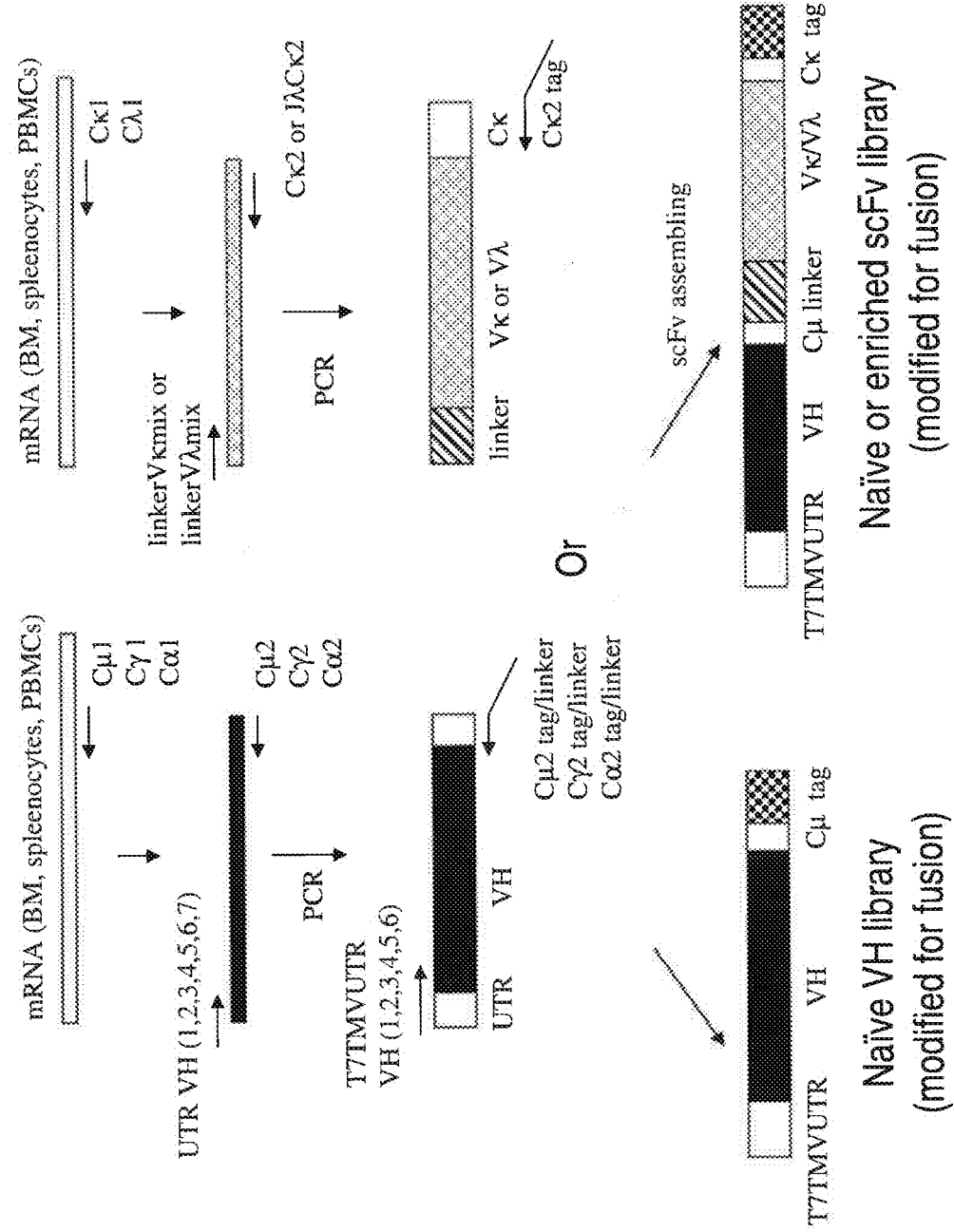
FIG. 24 illustrates one method of VH and VL library design from mRNA.
Figure 25:
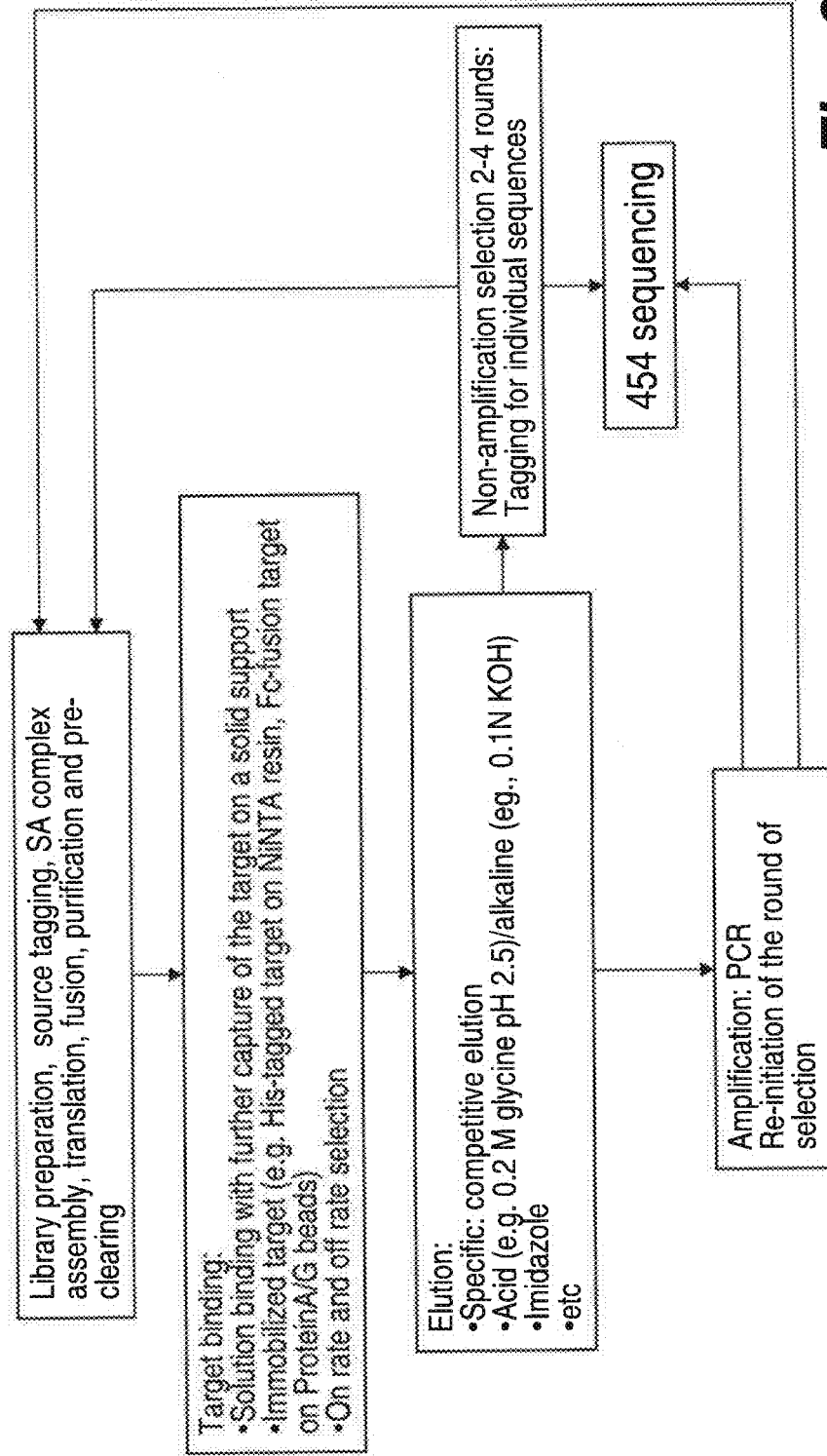
FIG. 25 illustrates one exemplary embodiment of selection method wherein the target molecule used in affinity selection is immobilized on a solid support.
Figure 26:
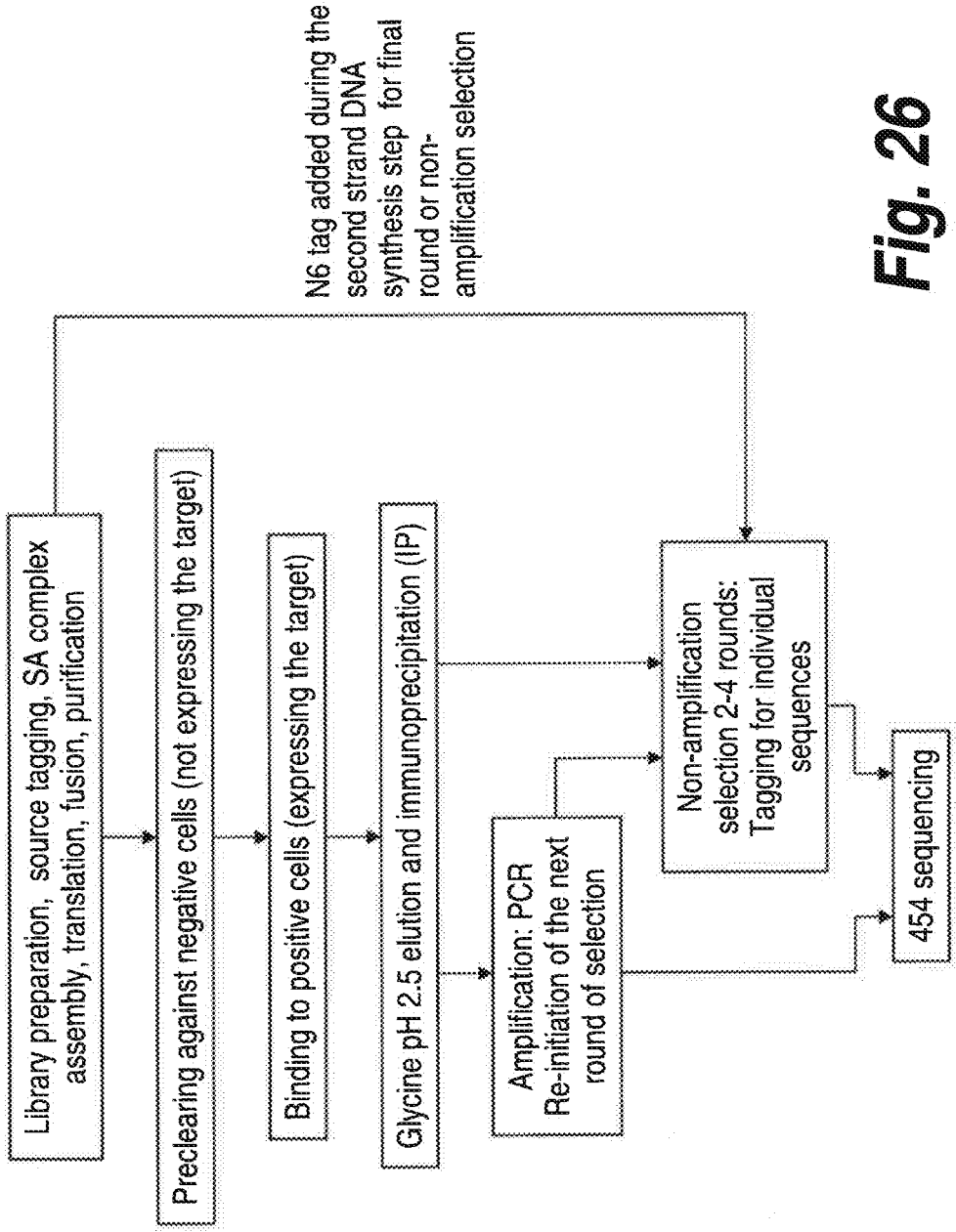
FIG. 26 illustrates one exemplary embodiment of selection method wherein the target molecule used in affinity selection is expressed on a cell surface. In such an embodiment the display complex is selected against cells not expressing the complex (e.g., in order to remove complexes which bind the cells but do not bind the target of interest) and then selected against cells which express the target of interest (i.e., to identify specific builders).
Figure 27:
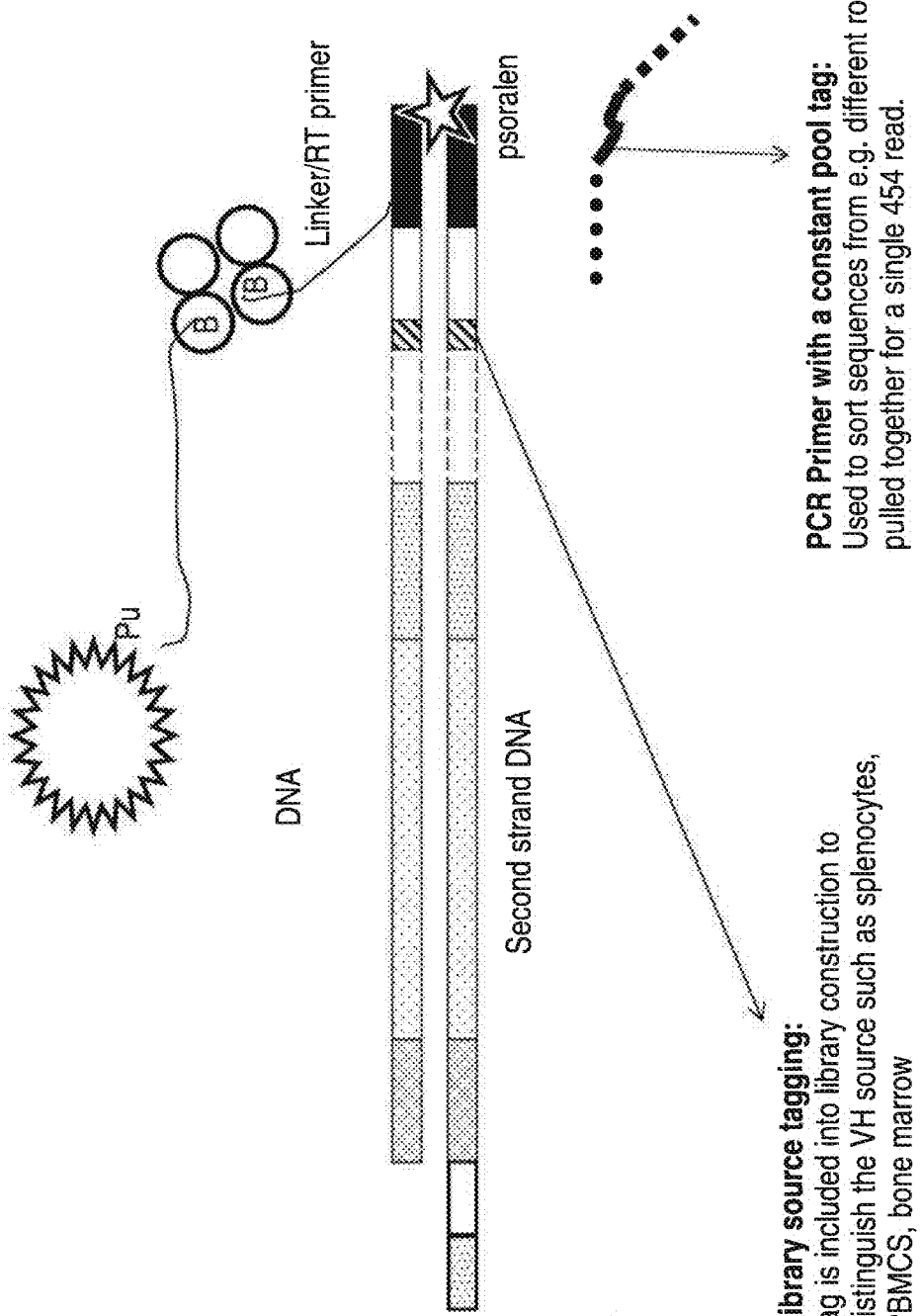
FIG. 27 illustrates a DNA X-display complex (i.e., a DNA-protein fusion) wherein source tags have been incorporated into the nucleic acid (e.g., to identify the source of the encoding DNA) and a constant source encoding used to tag nucleic acids from different rounds of selections (useful, e.g., when pooling nucleic acid from different selection rounds for one sequencing run).
Figure 28:
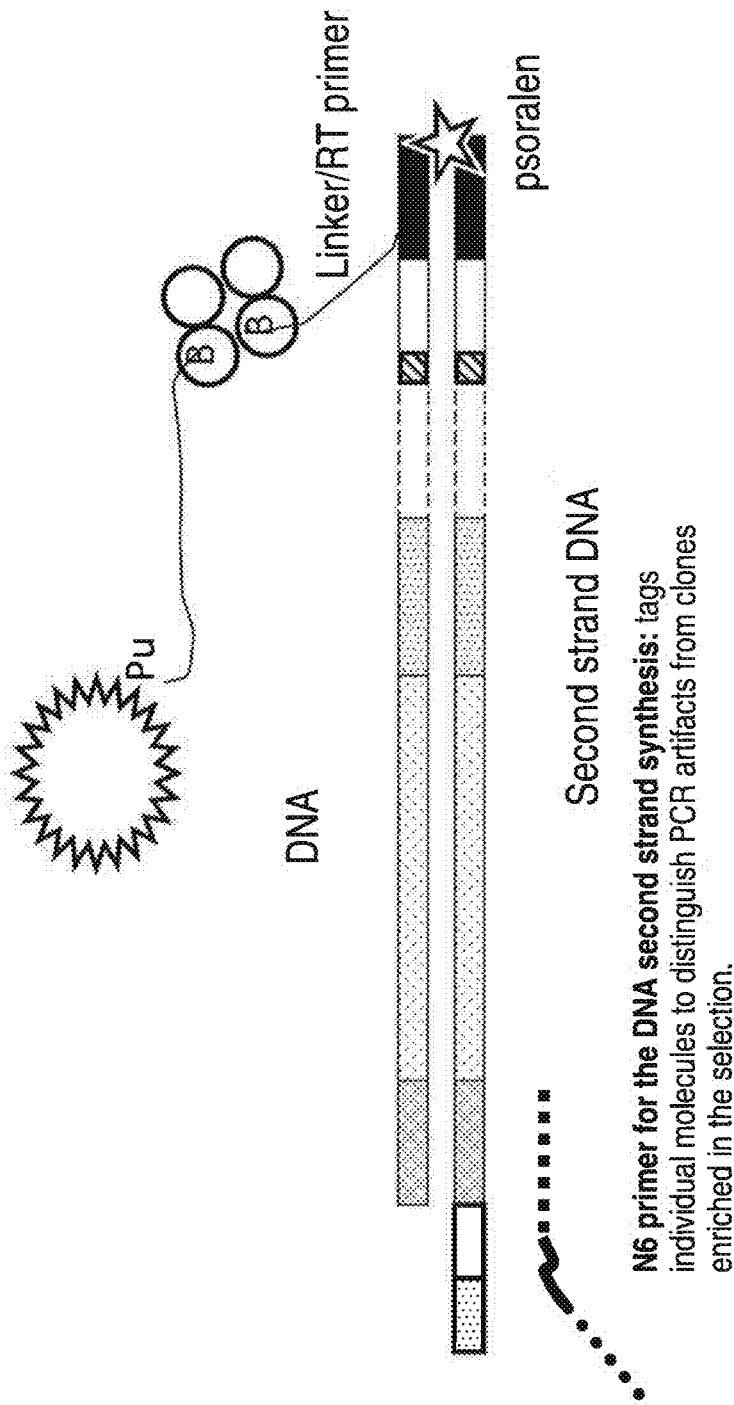
FIG. 28 illustrates a DNA X-display complex (i.e., a DNA-protein fusion) and the addition of an N6 primer.
Figure 29:
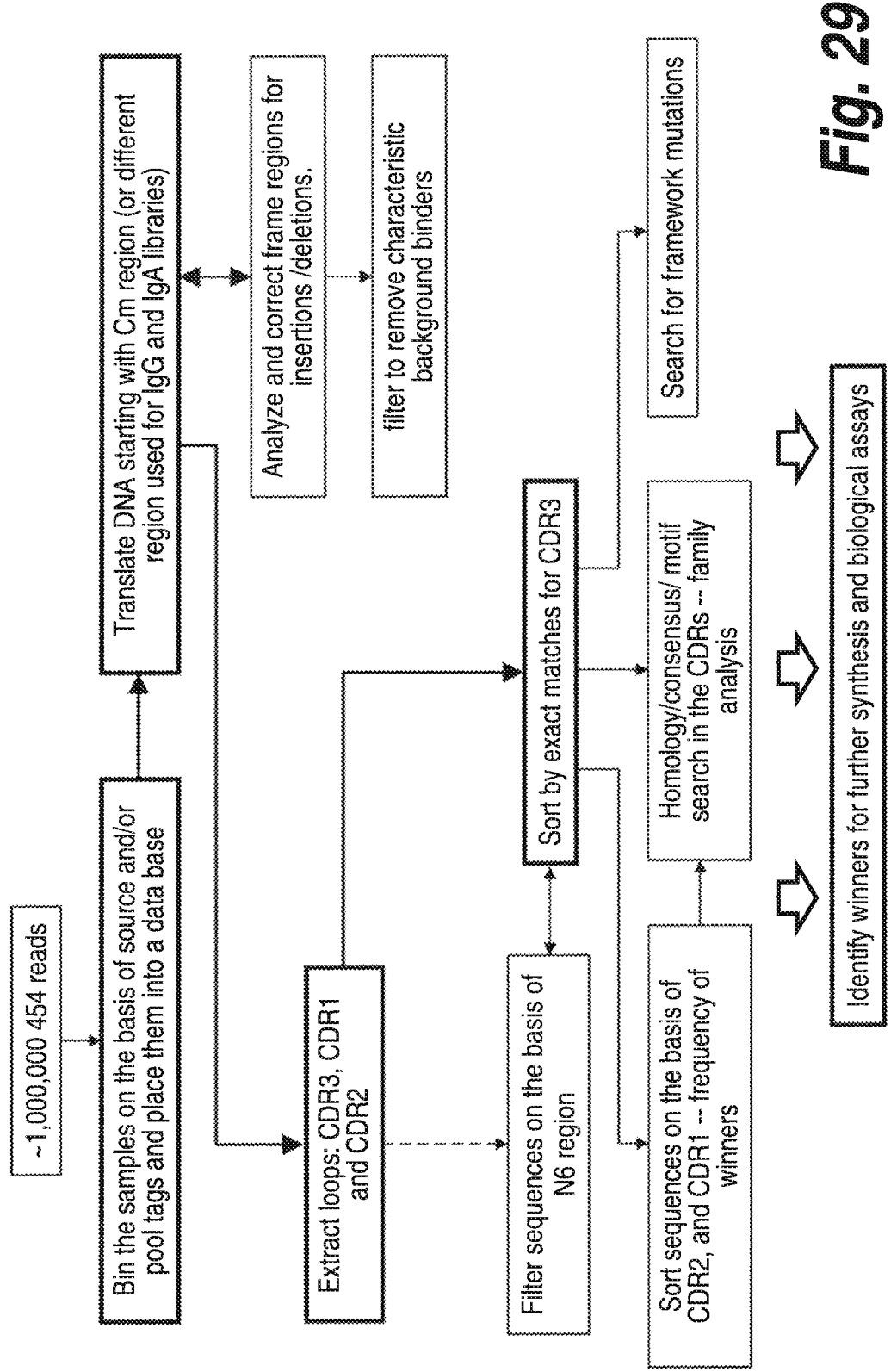
FIG. 29 depicts a flow chart showing one embodiment of a sequence analysis scheme.

It will be understood by one of skill in the art that the methods of the present invention may be employed in an iterative fashion. For example, the nucleic acid or protein selected by one of the methods described herein may serve as the basis for the generation of a new library from which the process may begin again. An example of such a scheme is illustrated in FIG. 22, wherein the products of one round of selection are used to regenerate a new library.

The X-display methodology described herein may be carried out under conditions such that intramolecular disulfide bonds are present in the peptides during selections. In other embodiments, the formation of disulfide bonds may be prevented, if desired. A starting library may be obtained by, e.g., direct DNA synthesis, through in-vitro or in-vivo mutagenesis, or any available starting library known in the art may be used. For example, the libraries and methods of making said libraries described in the references cited herein, and in the following references, which are all hereby incorporated in their entirety, may be used in accordance with the present invention: U.S. Pat. Nos. 5,922,545, 7,074, 557.

In preferred embodiments, the library is a VH or VL library. Table 2 provides a non-limiting set of example primers which may be used to amplify VH domains.

TABLE 2

Exemplary primers for VH domain X-display library generation.
R = A/G, Y = C/T, K = G/T, M = A/C, S = G/C, W = A/

| Target region | Primer details | Primer Sequence | SEQ ID No: |
|---|---|---|---|
| C 1 | IgM, cDNA synthesis, 21 mer | ACAGGAGACGAGGGGGAAAAG | 1. |
| C 1 | IgG, cDNA synthesis, 20 mer | GCCAGGGGGAAGACCGATGG | 2. |
| C 1 | IgA, cDNA synthesis, 22 mer | GAGGCTCAGCGGGAAGACCTTG | 3. |
| C 1 | Vk, cDNA synthesis, 21 mer | CAACTGCTCATCAGATGGCGG | 4. |
| C 1 | Vl, cDNA synthesis, 21 mer | CAGTGTGGCCTTGTTGGCTTG | 5. |
| C 2 | PCR 3' IgM, 21 mer | GGTTGGGGCGGATGCACTCCC | 6. |
| C 2 | PCR 3' IgG, 21 mer | CGATGGGCCCTTGGTGGARGC | 7. |
| C 2 | PCR 3' IgA, 21 mer | CTTGGGGCTGGTCGGGGATGC | 8. |
| C 2 | PCR 3' Vk, 21 mer | AGATGGTGCAGCCACAGTTCG | 9. |

TABLE 2-continued

Exemplary primers for VH domain X-display library generation.
R = A/G, Y = C/T, K = G/T, M = A/C, S = G/C, W = A/

| Target region | Primer details | Primer Sequence | SEQ ID No: |
|---|---|---|---|
| J 1-3C 2 | PCR 3' Vl, 42 mer | AGATGGTGCAGCCACAGTTCGTAGGACGGTSASCTTGGTCCC | 10. |
| J 7C 2 | PCR 3' Vl, 42 mer | AGATGGTGCAGCCACAGTTCGGAGGACGGTCAGCTGGGTGCC | 11. |
| VH1a | PCR5' VH1, 46 mer | CAATTACTATTTACAATTACAATGCAGGTKCAGCTGGTGCAGTCTG | 12. |
| VH1b | PCR5' VH1, 46 mer | CAATTACTATTTACAATTACAATGCAGGTCCAGCTTGTGCAGTCTG | 13. |
| VH1c | PCR5' VH1, 46 mer | CAATTACTATTTACAATTACAATGSAGGTCCAGCTGGTACAGTCTG | 14. |
| VH1d | PCR5' VH1, 46 mer | CAATTACTATTTACAATTACAATGCARATGCAGCTGGTGCAGTCTG | 15. |
| VH2 | PCR5' VH2, 46 mer | CAATTACTATTTACAATTACAATGCAGRTCACCTTGAAGGAGTCTG | 16. |
| VH3a | PCR5' VH3, 46 mer | CAATTACTATTTACAATTACAATGGARGTGCAGCTGGTGGAGTCTG | 17. |
| VH3b | PCR5' VH3, 46 mer | CAATTACTATTTACAATTACAATGCAGGTGCAGCTGGTGGAGTCTG | 18. |
| VH3c | PCR5' VH3, 46 mer | CAATTACTATTTACAATTACAATGGAGGTGCAGCTGTTGGAGTCTG | 19. |
| VH4a | PCR5' VH4, 42 mer | CAATTACTATTTACAATTACAATGCAGSTGCAGCTGCAGGAG | 20. |
| VH4b | PCR5' VH4, 45mer | CAATTACTATTTACAATTACAATGCAGGTGCAGCTACAGCAGTGG | 21. |
| VH5 | PCR5' VH5, 46mer | CAATTACTATTTACAATTACAATGGARGTGCAGCTGGTGCAGTCTG | 22. |
| VH6 | PCR5' VH6, 46mer | CAATTACTATTTACAATTACAATGCAGGTACAGCTGCAGCAGTCAG | 23. |
| VH7 | PCR5' VH7, 46mer | CAATTACTATTTACAATTACAATGCAGGTGCAGCTGGTGCAATCTG | 24. |
| linkVk1a | PCR5' VK1, 48 mer | GGCGGAGGTGGCTCTGGCGGTGGCGGATCGRACATCCAGATGACCCAG | 25. |
| linkVk1b | PCR5' VK1, 48 mer | GGCGGAGGTGGCTCTGGCGGTGGCGGATCGGMCATCCAGTTGACCCAG | 26. |
| linkVk1c | PCR5' VK1, 48 mer | GGCGGAGGTGGCTCTGGCGGTGGCGGATCGGCCATCCRGATGACCCAG | 27. |
| linkVk1d | PCR5' VK1, 48 mer | GGCGGAGGTGGCTCTGGCGGTGGCGGATCGGTCATCTGGATGACCCAG | 28. |
| linkVk2a | PCR5' VK2, 48 mer | GGCGGAGGTGGCTCTGGCGGTGGCGGATCGGATATTGTGATGACCCAG | 29. |
| linkVk2b | PCR5' VK2, 48 mer | GGCGGAGGTGGCTCTGGCGGTGGCGGATCGGATRTTGTGATGACTCAG | 30. |
| linkVk3a | PCR5' VK3, 48 mer | GGCGGAGGTGGCTCTGGCGGTGGCGGATCGGAAATTGTGTTGACRCAG | 31. |
| linkVk3a | PCR5' VK3, 48 mer | GGCGGAGGTGGCTCTGGCGGTGGCGGATCGGAAATAGTGATGACGCAG | 32. |
| linkVk3a | PCR5' VK3, 48 mer | GGCGGAGGTGGCTCTGGCGGTGGCGGATCGGAAATTGTAATGACACAG | 33. |
| linkVk4 | PCR5' VK4, 48 mer | GGCGGAGGTGGCTCTGGCGGTGGCGGATCGGACATCGTGATGACCCAG | 34. |

TABLE 2-continued

Exemplary primers for VH domain X-display library generation.
R = A/G, Y = C/T, K = G/T, M = A/C, S = G/C, W = A/

| Target region | Primer details | Primer Sequence | SEQ ID No: |
|---|---|---|---|
| linkVk5 | PCR5' VK5, 48 mer | GGCGGAGGTGGCTCTGGCGGTGGCGGATCG GAAACGACACTCACGCAG | 35. |
| linkVk6a | PCR5' VK6, 48 mer | GGCGGAGGTGGCTCTGGCGGTGGCGGATCG GAAATTGTGCTGACTCAG | 36. |
| linkVk6b | PCR5' VK6, 48 mer | GGCGGAGGTGGCTCTGGCGGTGGCGGATCG GATGTTGTGATGACACAG | 37. |
| linkVL1a | PCR5' VL1, 48 mer | GGCGGAGGTGGCTCTGGCGGTGGCGGATCG CAGTCTGTGCTGACKCAG | 38. |
| linkVL1b | PCR5' VL1, 48 mer | GGCGGAGGTGGCTCTGGCGGTGGCGGATCG CAGTCTGTGYTGACGCAG | 39. |
| linkVL2 | PCR5' VL2, 48 mer | GGCGGAGGTGGCTCTGGCGGTGGCGGATCG CAGTCTGCCCTGACTCAG | 40. |
| linkVL3a | PCR5' VL3, 48 mer | GGCGGAGGTGGCTCTGGCGGTGGCGGATCG TCCTATGWGCTGACTCAG | 41. |
| linkVL3b | PCR5' VL3, 48 mer | GGCGGAGGTGGCTCTGGCGGTGGCGGATCG TCCTATGAGCTGACACAG | 42. |
| linkVL3c | PCR5' VL3, 48 mer | GGCGGAGGTGGCTCTGGCGGTGGCGGATCG TCTTCTGAGCTGACTCAG | 43. |
| linkVL3d | PCR5' VL3, 48 mer | GGCGGAGGTGGCTCTGGCGGTGGCGGATCG TCCTATGAGCTGATGCAG | 44. |
| linkVL4 | PCR5' VL4, 48 mer | GGCGGAGGTGGCTCTGGCGGTGGCGGATCG CAGCYTGTGCTGACTCAA | 45. |
| linkVL5 | PCR5' VL5, 48 mer | GGCGGAGGTGGCTCTGGCGGTGGCGGATCG CAGSCTGTGCTGACTCAG | 46. |
| linkVL6 | PCR5' VL6, 48 mer | GGCGGAGGTGGCTCTGGCGGTGGCGGATCG AATTTTATGCTGACTCAG | 47. |
| linkVL7 | PCR5' VL7, 48 mer | GGCGGAGGTGGCTCTGGCGGTGGCGGATCG CAGRCTGTGGTGACTCAG | 48. |
| linkVL8 | PCR5' VL8, 48 mer | GGCGGAGGTGGCTCTGGCGGTGGCGGATCG CAGACTGTGGTGACCCAG | 49. |
| linkVL4/9 | PCR5' VL4/9, 48 mer | GGCGGAGGTGGCTCTGGCGGTGGCGGATCG CWGCCTGTGCTGACTCAG | 50. |
| linkVL10 | PCR5' VL10, 48 mer | GGCGGAGGTGGCTCTGGCGGTGGCGGATCG CAGGCAGGGCTGACTCAG | 51. |

In preferred embodiments the nucleic acid constructs of the library contain the T7 promoter. The nucleic acids in the library may be manipulated by any means known in the art to add appropriate promoters, enhancers, spacers, or tags which are useful for the production, selection, or purification of the nucleic acid, its translation product, or the X-display complex. For example, in some embodiments the sequences in the library may include a TMV enhancer, sequences encoding a FLAG tag, an SA display sequence, or a polyadenylation sequence or signal. In some embodiments the nucleic acid library sequences may further include a unique source tag to identify the source of the RNA or DNA sequence. In some embodiments the nucleic acid library sequences may include a pool tag. A pool tag may be used to identify those sequence selected during a particular round of selection. This will allow, e.g., sequences from multiple selection rounds to be pooled and sequenced in a single run without losing track of which selection round they originated from.

The double stranded DNA library is then transcribed in-vitro and associated, as described herein, to a peptide acceptor. In one preferred embodiment, an NA linker or an NA linker attached to a high affinity ligand (e.g., a biotinylated NA linker) is then annealed (e.g., DDB-1). In some embodiments, the NA linker is photocrosslinked to the mRNA. In particular embodiments a ligand acceptor, e.g., streptavidin, is then loaded. In further embodiments a second high affinity ligand which is attached to a peptide acceptor is bound to the streptavidin. In some embodiments the second high affinity ligand/peptide acceptor is a biotin-puromycin linker, e.g., BPP.

in vitro translation may then be carried out wherein the peptide acceptor reacts with the nascent translation product.

The result, after purification, is a library of peptide-nucleic acid X-display complexes. Such X-display complexes may then undergo reverse transcription after, in preferred embodiments, being purified. The X-display complexes may be purified by any method known in the art, e.g., by affinity chromatography, column chromatography, density gradient centrifugation, affinity tag capture, etc. In a preferred embodiment an oligo-dT cellulose purification is employed wherein the X-display complex has been designed to include an mRNA with a poly-A tail. In such embodiments oligo-dT is covalently bound to the cellulose in the column or purification device. The oligo-dT participates in complementary base pairing with the poly-A tail of the mRNA in the X-display complex, thereby impeding its progress in through the purification device. The X-display complex may later be eluted with water or buffer.

Reverse transcription generates a cDNA/RNA hybrid, which, in preferred embodiments is noncovalently linked to the transcribed peptide through association with the NA linker, the high affinity ligand, the ligand acceptor, the peptide acceptor (possibly linked to a second high affinity ligand), or some operable combination thereof.

The resulting, purified X-display complex may then be treated with RNAse to degrade the remaining mRNA, followed by second strand DNA synthesis to generate a complete cDNA. Note that, in a preferred embodiment, the nucleic acids in the NA linker may serve as a primer for reverse transcription. Accordingly, the cDNA remains attached to the high affinity ligand and part of the X-display complex.

The X-display complex may be further purified if, as is contemplated, the X-display complex is engineered to contain a tag. Any tag known in the art may be used to purify the X-display complex. For example, it is possible to use a FLAG tag, myc tac, Histidine tag (His tag), or HA tag, among others. In preferred embodiments a sequence encoding a FLAG tag is engineered into the original DNA sequence such that the final transcribed protein contains the FLAG tag.

The resulting X-display complex is then selected for by using any selection method known in the art. In preferred embodiments affinity selection is used. For example, the desired binding target or antigen may be immobilized on a solid support for use in an affinity column. Examples of methods useful in affinity chromatography are described in U.S. Pat. Nos. 4,431,546, 4,431,544, 4,385,991, 4,213,860, 4,175,182, 3,983,001, 5,043,062, which are all incorporated herein by reference in their entirety. Binding activity can be evaluated by standard immunoassay and/or affinity chromatography. Screening of X-display complexes for catalytic function, e.g., proteolytic function can be accomplished using a standard hemoglobin plaque assay as described, for example, in U.S. Pat. No. 5,798,208. Determining the ability of candidate peptides (e.g., antibodies, single chain antibodies, etc.) to bind therapeutic targets can be assayed in vitro using, e.g., a Biacore instrument, which measures binding rates of an antibody to a given target or antigen.

In preferred embodiments, the selected X-display complexes may be identified by sequencing of the DNA component. Any sequencing technology known in the art may be employed, e.g., 454 Sequencing, Sanger sequencing, sequencing by synthesis, or the methods described in U.S. Pat. Nos. 5,547,835, 5,171,534, 5,622,824, 5,674,743, 4,811,218, 5,846,727, 5,075,216, 5,405,746, 5,858,671, 5,374,527, 5,409,811, 5,707,804, 5,821,058, 6,087,095, 5,876,934, 6,258,533, 5,149,625 which are all incorporated herein by reference in their entirety.

In some embodiments the selection may be performed multiple times to identify higher affinity binders, and may further be implemented with competitive binders or more stringent washing conditions. One of skill in the art will appreciate that variants of the procedure described herein may be employed.

Figure 14:
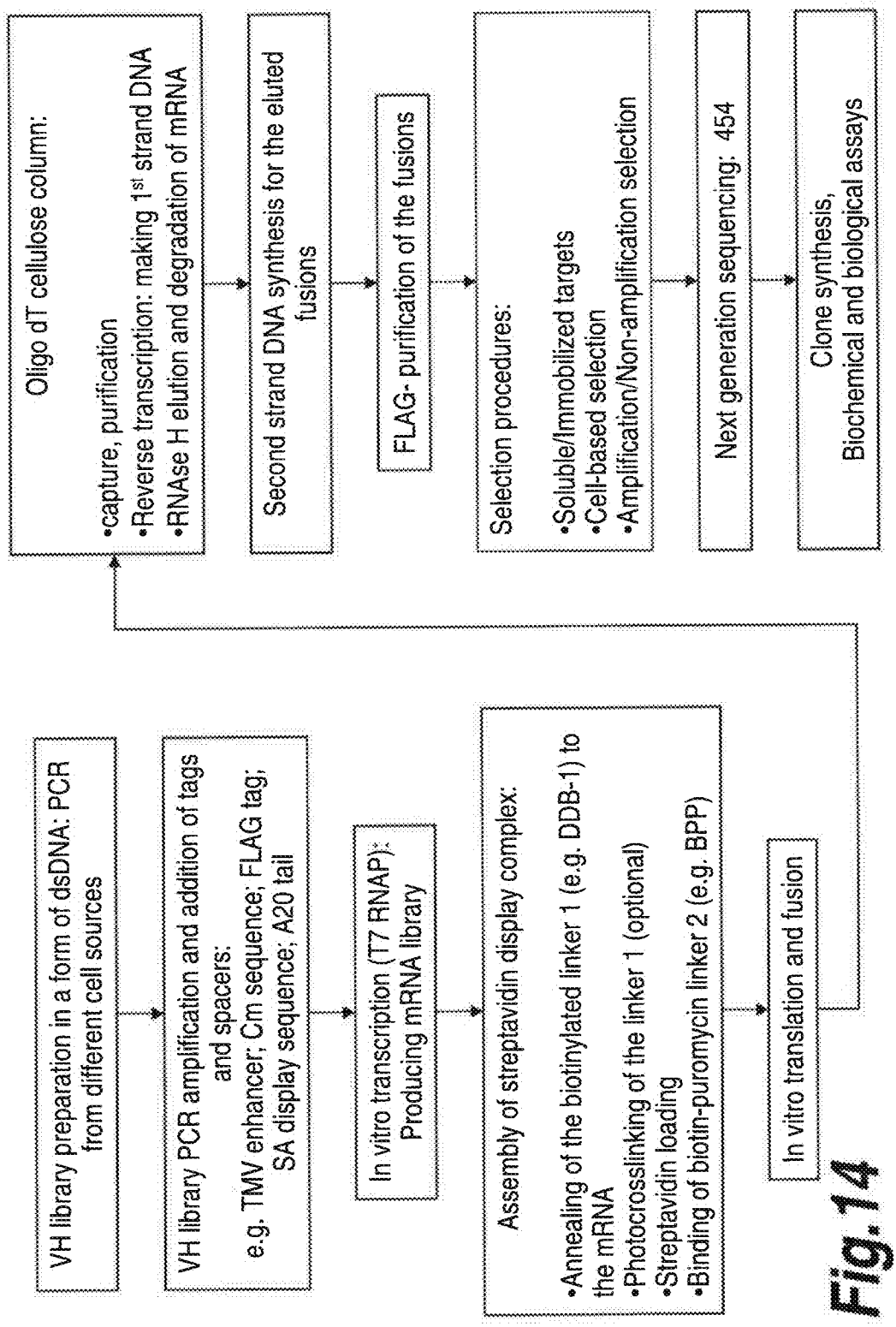
FIG. 14 illustrates an exemplary scheme for preparing a VH library, assembling the display complex, selecting, and purifying the display complex.

In a preferred embodiment, the methods of the present invention are carried out as depicted in FIG. 14.

Figure 13:
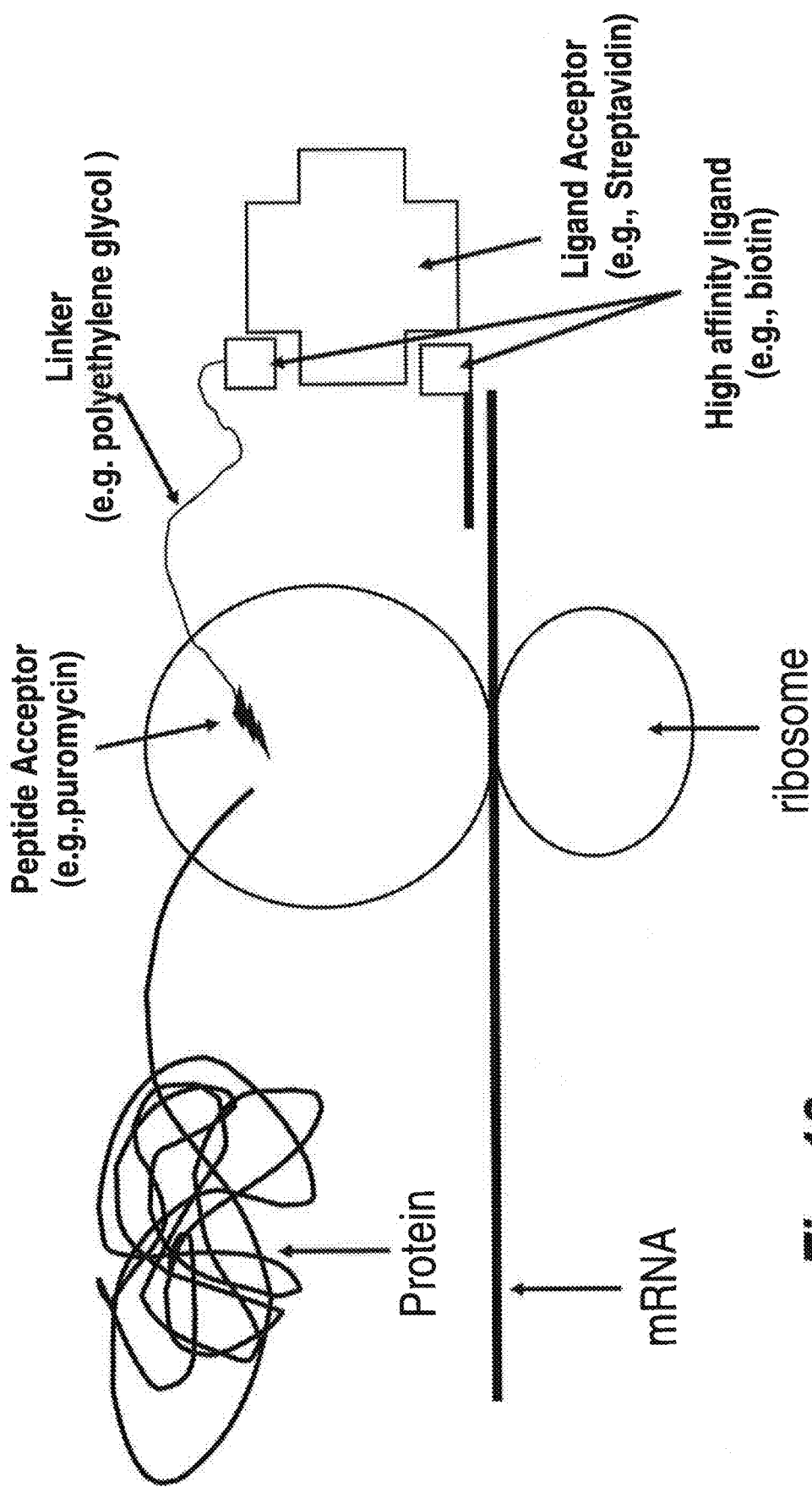
FIG. 13 illustrates the design of a preferred X-display complex.
Figure 16A:
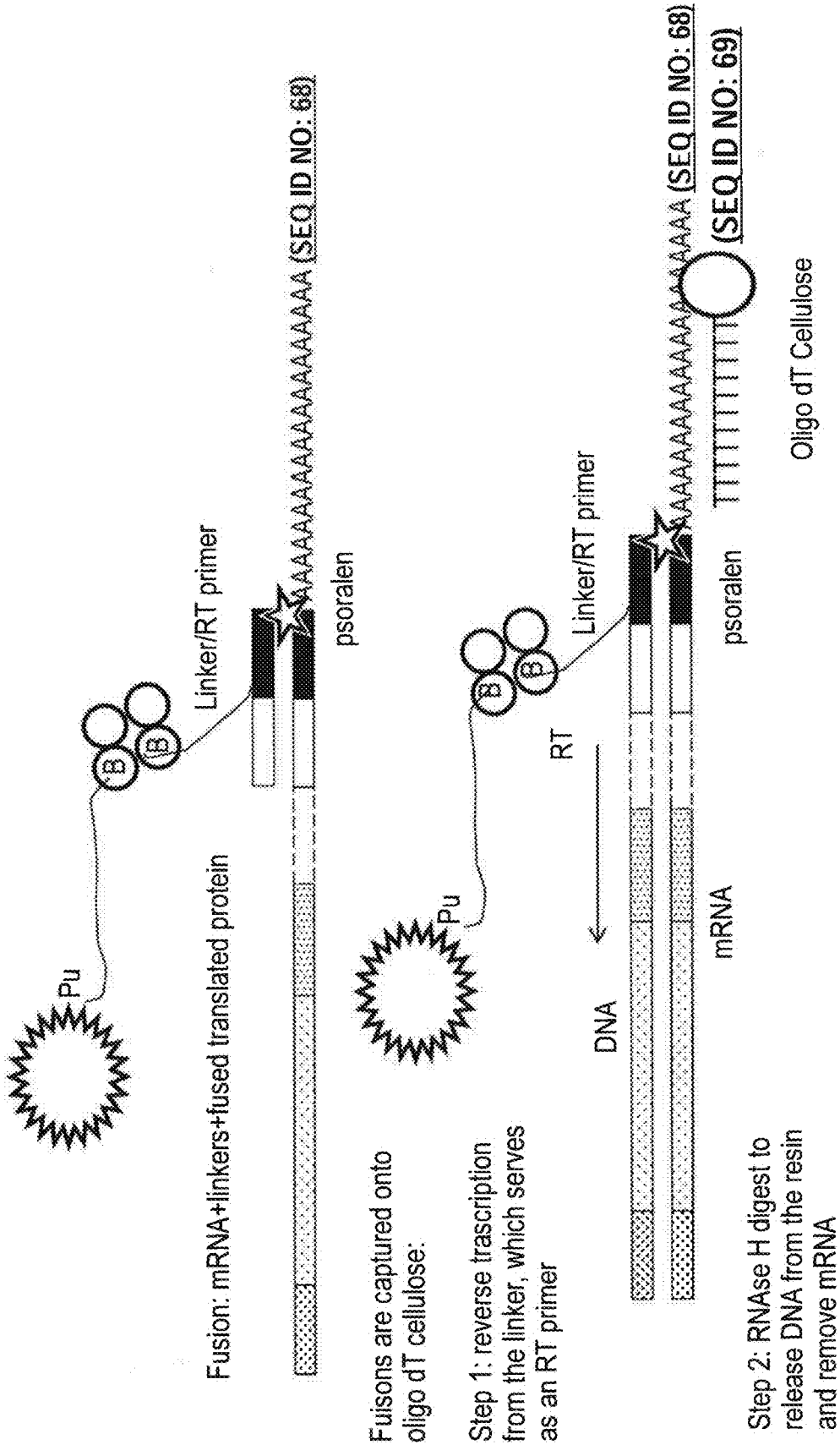
FIGS. 16A-16B illustrate the steps of a preferred embodiment of the display methodology.
Figure 16B:
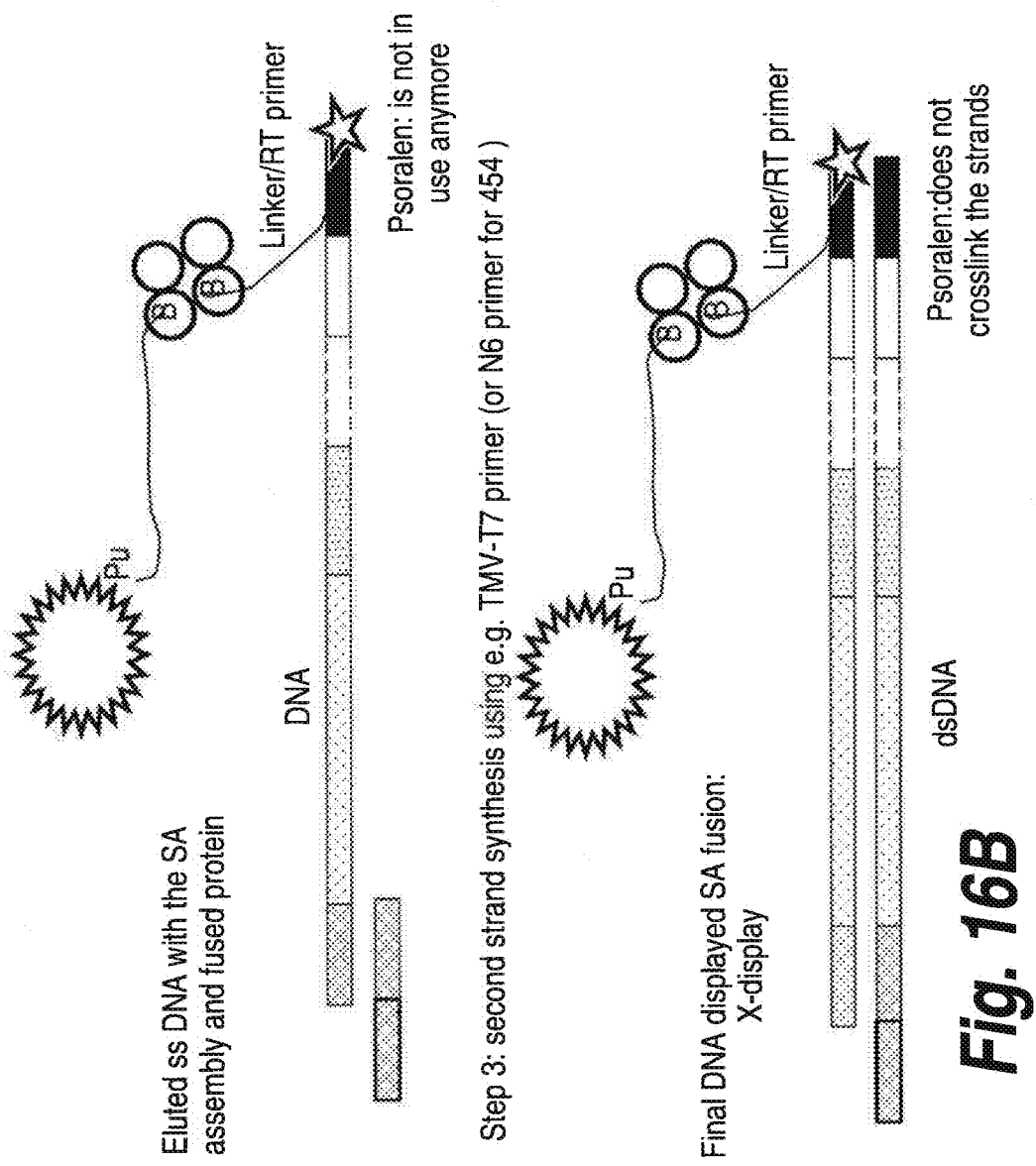
Figure 18:
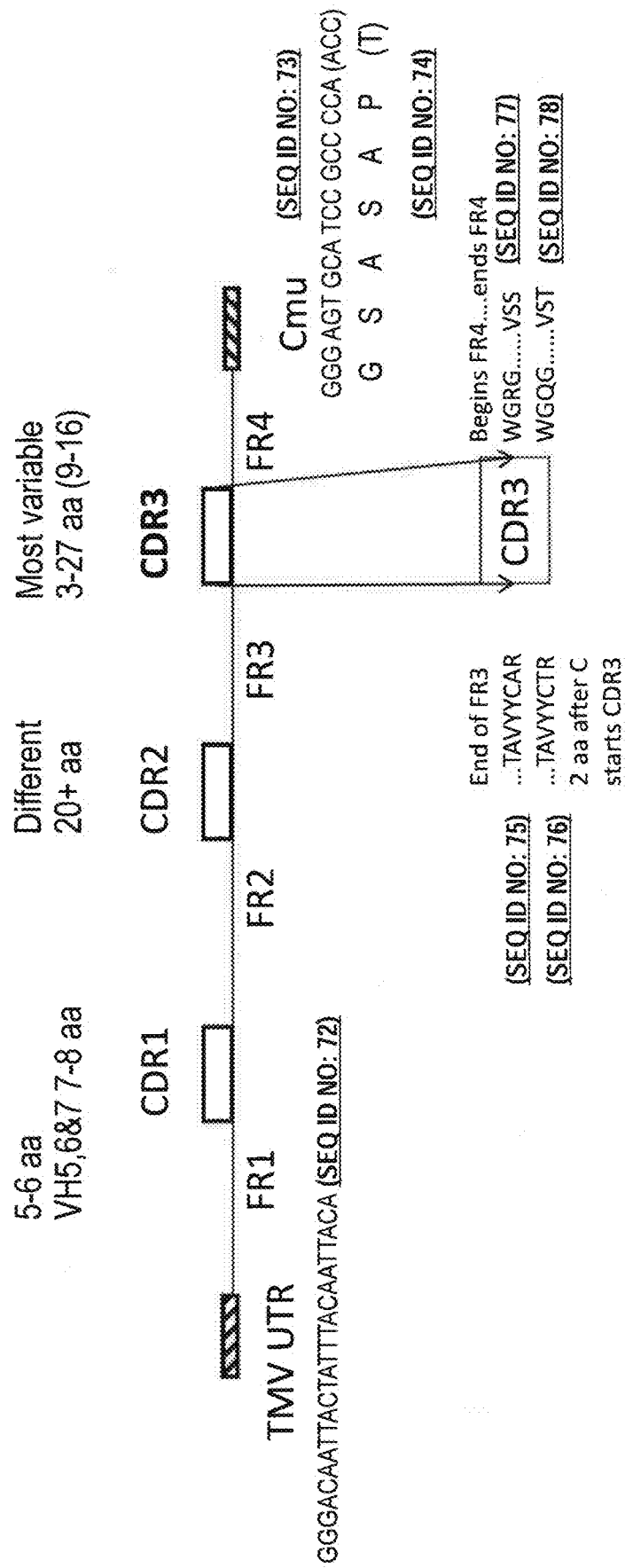
FIG. 18 (SEQ ID NOS: 72-78) depicts an exemplary segment of a VH library member.
Figure 19:
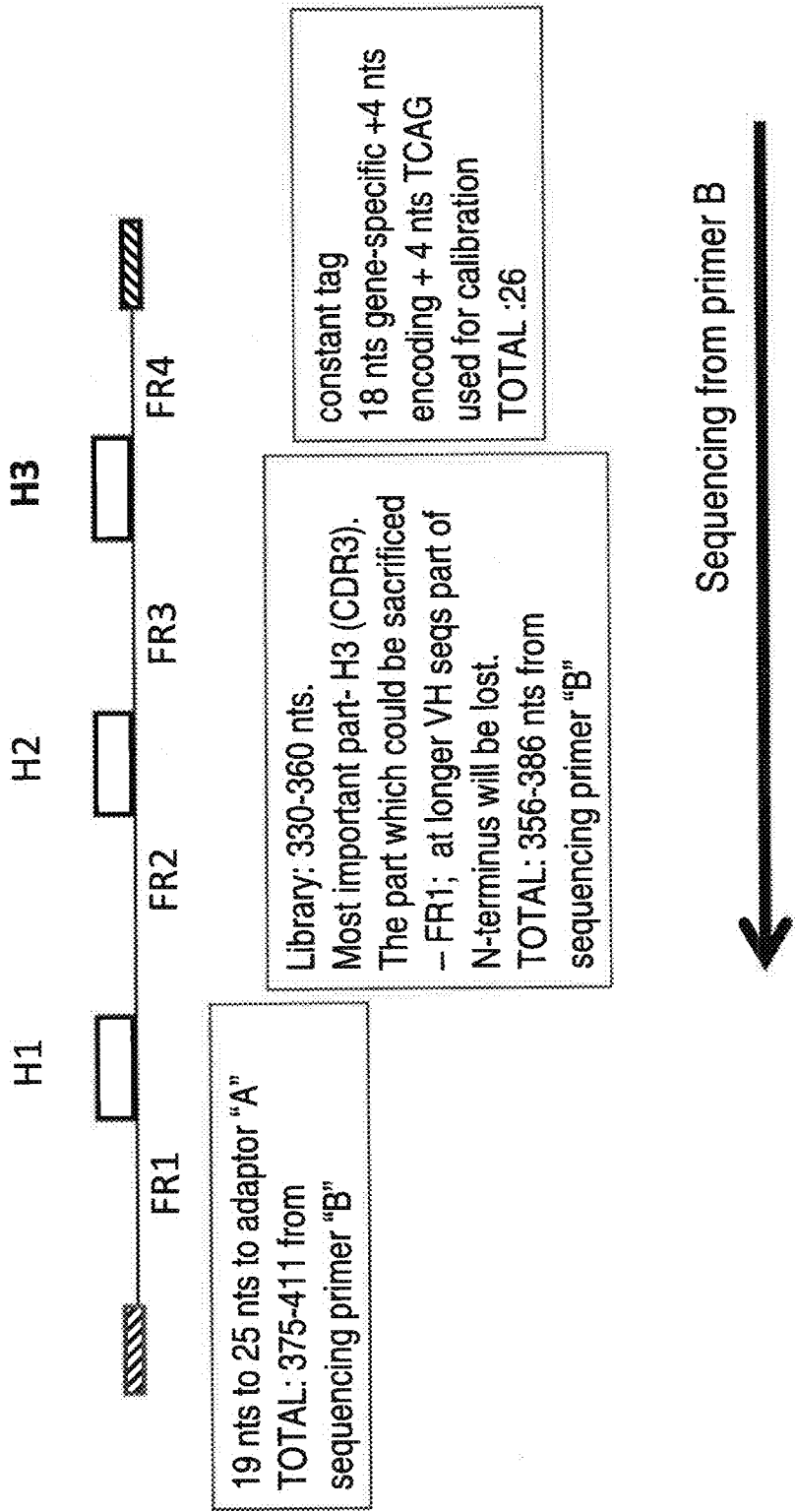
FIG. 19 depicts an exemplary segment of a display library member and further displays end sequences from the primers (see FIG. 17).
Figure 20:
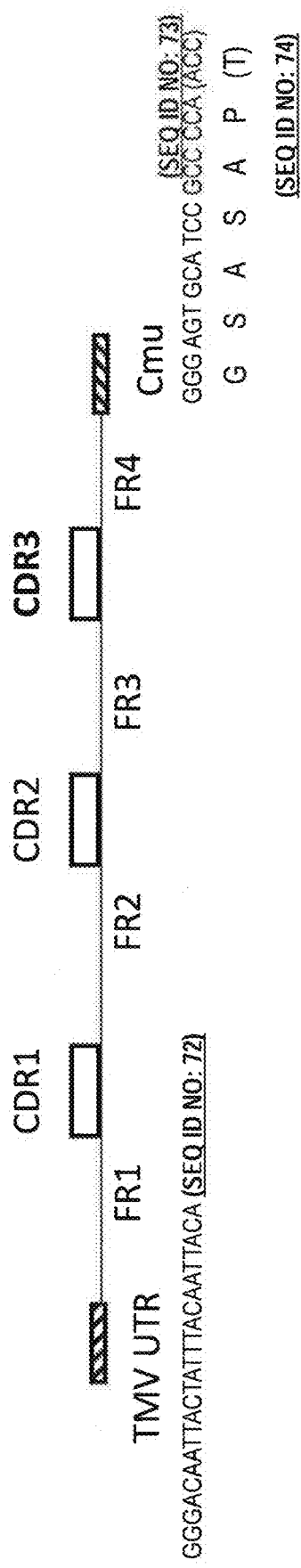
FIG. 20 (SEQ ID NOS: 72-74 and 79-81) depicts an exemplary segment of a display library member and further provides the exemplary sequence the TMV UTR and C-mu regions from the primers.
Figure 21:
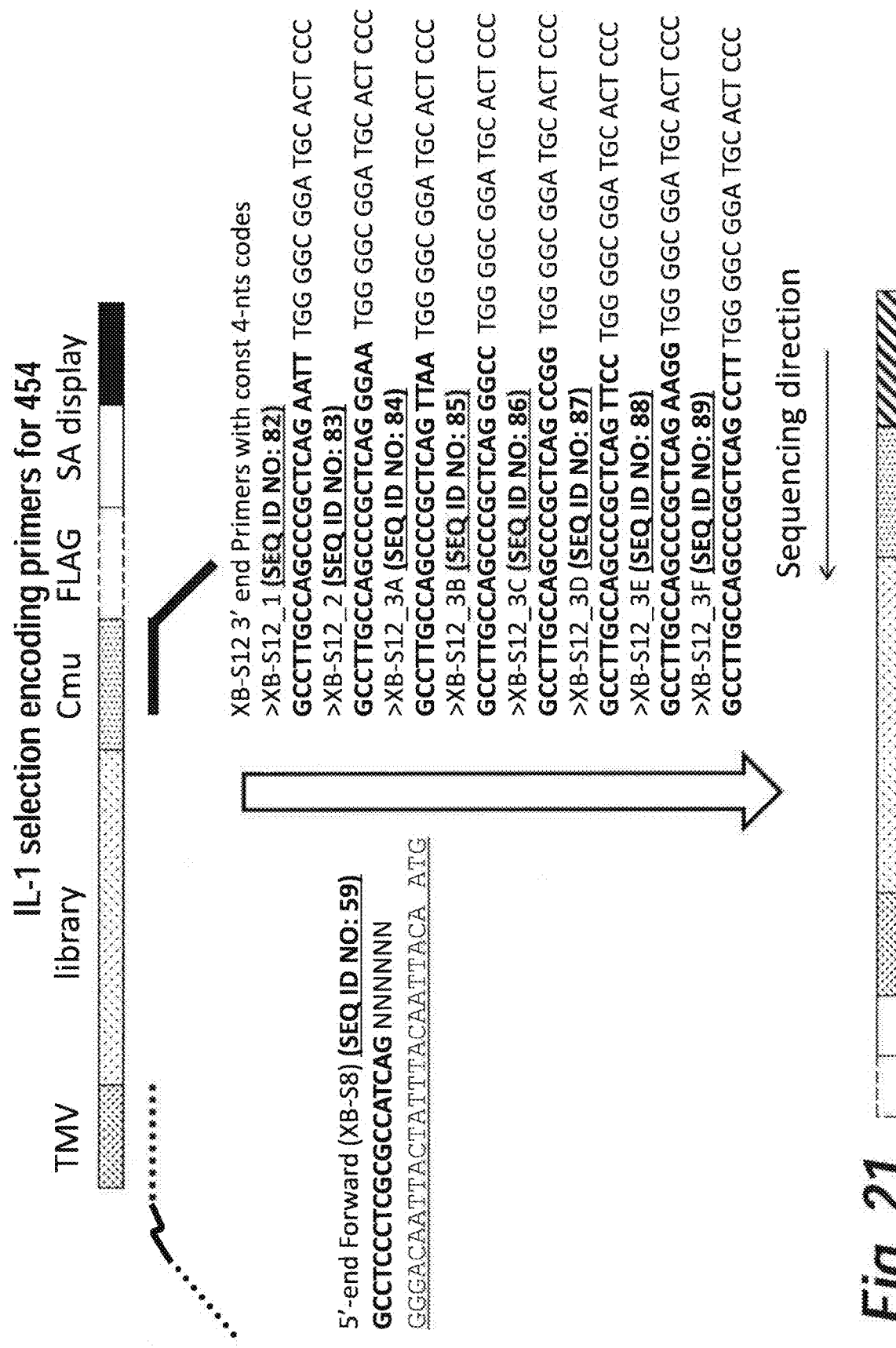
FIG. 21 (SEQ ID NOS: 59, 82-89) depicts a possible arrangement of primers for amplifying a clone selected for sequencing.

In other preferred embodiments the X-display complex is designed as depicted in FIG. 13 or FIG. 16.

Pharmaceutical Compositions Containing the Peptides or Mimetics Thereof of the Invention In another aspect, the present invention provides a composition, e.g., a pharmaceutical composition, containing one or a combination of the peptides (e.g., two or more different peptides) generated by the methods of the invention, formulated together with a pharmaceutically acceptable carrier. Pharmaceutical compositions of the invention also can be administered in combination therapy, i.e., combined with other agents. For example, the combination therapy can include a peptide or mimetic thereof of the invention combined with other appropriate pharmaceutical agents useful for treating a particular disease or indication.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the peptide or mimetic thereof of the invention may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

In a particular embodiment the a peptides or mimetic thereof selected by methods of the invention may be dissolved in water with sodium chloride to achieve physiological isotonic salt conditions.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The peptides can also be in micro-encapsulated form, if appropriate, with one or more excipients.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

A composition formulated as a solution may be made suitable for administration by dropper into the eye, e.g., by preparing the solution to contain the appropriate amount of salts.

Liposomes containing a peptide or mimetic thereof selected by methods of the present invention can be prepared in accordance with any of the well known methods such as described by Epstein et al. (Proc. Natl. Acad. Sci. USA 82: 3688-3692 (1985)), Hwang et al. (Proc. Natl. Acad. Sci. USA 77: 4030-4034 (1980)), EP 52,322, EP 36,676; EP 88,046; EP 143,949; EP 142,641; Japanese Pat. Appl. 83-118008, and EP 102,324, as well as U.S. Pat. Nos. 4,485,045 and 4,544,545, the contents of which are hereby incorporated by reference in their entirety. Liposomes may be small (about 200-800 Angstroms) unilamellar type in which the lipid content is greater than about 10 mol. percent cholesterol, preferably in a range of 10 to 40 mol. percent cholesterol, the selected proportion being adjusted for optimal peptide therapy. However, as will be understood by those of skill in the art upon reading this disclosure, phospholipid vesicles other than liposomes can also be used.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the peptide or mimetic thereof of the invention, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for a moiety of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively, the peptide or mimetic thereof selected by the methods of the invention can be administered as a sustained release formulation, in which case less frequent administration is required. Dosage and frequency vary depending on the half-life of the administered substance in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients and small molecules in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a peptide or mimetic thereof selected by the methods of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 10% or 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for binding moieties of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a peptide or mimetic thereof of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

The present invention is further illustrated in the following examples, which should not be construed as limiting.

EXEMPLIFICATION

Throughout the examples, the following materials and methods were used unless otherwise stated.
Materials and Methods In general, the practice of the present invention employs, unless otherwise; indicated, conventional techniques of chemistry, molecular biology, recombinant DNA technology, PCR technology, immunology (especially, e.g. antibody technology), expression systems (e.g., cell-free expression, phage display, ribosome display, and Profusion), and any necessary cell culture that are within the skill of the art and are explained in the literature. See, e.g. Sambrook, Fritsch and Maniatis, Molecular Cloning: Cold Spring Harbor Laboratory Press (1989); DNA Cloning, Vols. 1 and 2, (D. N. Glover, Ed. 1985); Oligonucleotide Synthesis (M. J. Gait, Ed. 1984); PCR Handbook Current Protocols in Nucleic Acid Chemistry, Beaucage, Ed. John Wiley & Sons (1999) (Editor); Oxford Handbook of Nucleic Acid Structure, Neidle, Ed., Oxford Univ Press (1999); PCR Protocols: A Guide to Methods and Applications, Innis et al., Academic Press (1990); PCR Essential Techniques: Essential Techniques, Burke, Ed., John Wiley & Son Ltd (1996); Ike PCR Technique: RT-PCR, Siebert, Ed., Eaton Pub. Co. (1998); Antibody Engineering Protocols (Methods in Molecular Bioogy), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); Current Protocols in Molecular Biology, eds. Ausubel et al., John Wiley & Sons (1992); Large-Scale Mammalian Cell; Culture Technology, Lubiniecki, A., Ed., Marcel Dekker, Pub., (1990).

The compositions and methods of the invention can, in some embodiments, be used in conjunction with those of any other art recognized in vitro display system, for example, those described in U.S. Pat. Nos. 7,195,880; 6,951,725; 7,078,197; 7,022,479, 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; 6,194,550; 6,207,446; 6,214,553; and 6,348,315, which are hereby incorporated by reference.

EXAMPLES

The present disclosure is further illustrated by the following examples, which should not be construed as further limiting.

Example 1

Design and Construction of Naïve Antibody Libraries

Sources of Cells mRNA was obtained from whole bone marrow (10 donors), spleenocytes (13 donors) and peripheral mononuclear cells (601 donors) of total 624 different healthy individuals, to ensure the diversity of the library. The calculated diversity of VH library is $10^9$-$10^{19}$ and VL library is $10^6$-$10^7$.

Library Construction

RT-PCR was used for VH and VL library construction.

First strand cDNA was synthesized using specific primers from the H chain constant regions of IgM, IgG and IgA (C 1, C 1 and C 1), and L chain constant regions of kappa and lambda (C 1 and C).

For variable H chain library construction, multiple sense primers (degenerate primers) were designed from the FR1 regions of VH1-7 family members with an upstream UTR sequence (VH1-7UTR). The anti-sense primers for VH were designed from the constant regions nested to the primers for cDNA synthesis (C 2, C 2 and C 2). For variable light chain library construction, multiple sense primers were designed from the V and V FR1 regions of each family with an upstream 12 amino acids of the linker sequence to allow for single chain Fv shuffling. The anti-sense primers for and gene amplification were designed from the constant regions nested to C 1 (C 2) or J with the same C 2 downstream (J C 2). The assembled scFv of all IgM and IgG families will have the same C 2 sequences at the downstream end if needed.

For VH library construction, PCR was performed with C 2, C 2, C 2 and VH1-7 UTR as individual pairs for all three sources of B cells and gel purified. After purification, individual families amplified from 3 sources were pooled and generated 7 (VH1-7) IgM libraries, 7 (VH1-7) IgG libraries and 7 IgA libraries (VH1-7). For VL library construction, PCR was performed with C 2 and V or J C 2 mix and V for 3 sources of B cells. After gel purification, V and V libraries from different sources were pooled to generate V and V libraries.

Library Modification

IgM, IgG, IgA VH libraries and VL libraries were also modified to carry the in vitro transcription, translation signal sequences at 5' end and tag sequences at 3' end. These VH libraries are ready to be made into streptavidin display libraries.

Oligo Sequences for Library Construction

The oligonucleotides primers set forth in Table 2 were used to generate VH and VL X-display libraries.

Example 2

Production and Use of Streptavidin Display Libraries

This example describes the production and use of the streptavidin display libraries of the invention Materials and Methods In general, the practice of the present invention may employ, unless otherwise indicated, conventional techniques of chemistry, molecular biology, recombinant DNA technology, immunology (especially, e.g., antibody technology), and standard techniques of polypeptide preparation. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Buffers

10× chemical ligation buffer: 250 mM Tris pH7 and 1M NaCl

1× oligo dT binding buffer: 100 mM Tris pH8, 1M NaCl, and 0.05% Triton X-100

2× oligo dT binding buffer: 200 mM Tris pH8, 2M NaCl, and 0.1% Triton X-100

1× flag binding buffer: 50 mM HEPES, 150 mM NaCl, and 0.025% Triton X-100 or

1×PBS and 0.025% Triton X-100

5× flag binding buffer: 250 mM HEPES, 750 mM NaCl, and 0.125% Triton X-100 or 5× PBS and 0.125% Triton X-100

Source of Used Reagents

Megascript T7: Ambion (Austin, Tex.) PH 1334

Retic lysate IVT: Ambion (Austin, Tex.) PH1200

UC Master mix-met: Ambion (Austin, Tex.) PH 1223G

Superscript II RNaseH-RT: Invitrogen (Carlsbad, Calif.) #18064-014

NAP-25 column: Amersham Pharmacia Biotech (Sunnyvale, Calif.) #17-0852-01

Oligo dT cellulose Type 7: Amersham Pharmacia Biotech (Sunnyvale, Calif.) #27-5543-03

Anti-flag M2 agarose affinity gel: Sigma (St. Louis, Mo.) #A2220

Flag peptide: Sigma (St. Louis, Mo.) #F3290 dNTP: Amersham Pharmacia Biotech (Sunnyvale, Calif.) #27-2035-01

Herculase Hotstart DNA polymerase: Stratagene (La Jolla, Calif.) 600312-51

Mini spin column: Biorad (Hercules, Calif.) #732-6204
Ultrapure BSA: Ambion (Foster City, Calif.) #2616
Sheared salmon sperm DNA: Ambion (Foster City, Calif.) #9680
Linkers: PBI, DDB, BPP: Trilink BioTechnologies, Inc. (San Diego, Calif.)
H$_2$O: OmniPur (Gibbstown, N.J.) #9610
2M KCl: Usb (Cleveland, Ohio) #75896
1M MgCl2: Usb (Cleveland, Ohio) #78641
0.5M EDTA: Usb (Cleveland, Ohio) #15694
1M Tris pH8: Usb (Cleveland, Ohio) #22638
1M Tris pH7: Usb (Cleveland, Ohio) #22637
5M NaCl: Usb (Cleveland, Ohio) #75888
1M HEPES: Usb (Cleveland, Ohio) #16924
Qiaquick gel extraction kit: Qiagen (Valencia, Calif.) #28706
6% TBE-Urea gels: Invitrogen (Carlsbad, Calif.) EC6865BOX
4-16% NativePAGE Gel: Invitrogen (Carlsbad, Calif.)
Special Reagents Preparation
Oligo dT Cellulose (Final Concentration: 100 mg/ml)

2.5 g of oligo dT cellulose were mixed with 25 ml of 0.1N NaOH in a 50 ml tube. After spinning of the mixture at 1500 rpm for 3 minutes, the resulting supernatant was discarded. The resulting pellet containing the oligo dT cellulose was washed with 25 ml of 1× oligo dT binding buffer and then precipitated again by spinning at 1500 rpm for 3 minutes. The resulting supernatant was again separated from the pellet and discarded. This wash step was repeated for 3 more times. After the last time of washing, the pH of the resulting supernatant was measured. The pH should be the same as wash buffer (~pH 8.5). Then the pellet containing the oligo dT cellulose was separated from the supernatant and re-suspended in 25 ml of 1× oligo dT binding buffer before storing at 4 C.

M2 Agarose Preparation 25 ml of M2 agarose slurry was transferred into a 50 ml of tube. After spinning for 5 minutes at 1000 RPM in a Beckman centrifuge, the supernatant was separated and discarded. The resulting pellet containing M2 agarose was re-suspended with one column volume of Glycine 10 mM pH 3.5 and spilled for 5 minutes at 1000 RPM. The resulting supernatant was again discarded. The agarose pellet was then re-suspended with one column volume of 1× flag binding buffer. The mixture was spilled for 5 minutes at 1000 RPM and the resulting supernatant was discarded. This wash step was repeated for 3 times and then the pellet was re-suspended with one column volume of 1× binding buffer (with 1 mg/ml of BSA and 100 µg/ml of sssDNA). The mixture was tumbled for 1 hour or overnight at 4° C. before being separated in aliquots in 2 ml fractions and stored at 4° C.

Amplification of the VH Library

An exemplary method for amplifying the VH library is given below:

```
Primers:
5' Primer: S7 (T7TMVUTR)
                                            (SEQ ID No: 52)
5'-TAATACGACTCACTATAGGGACAATTACTATTTACAATTACA-3'

5' Primer: S7a (T7TMVUTR AUG)
                                            (SEQ ID No: 53)
5'-TAATACGACTCACTATAGGGACAATTACTATTTACAATTACAAT
G-3'

3' Primer: XB-S5-1 (Cµ2flagA20 +
SA display added sequence)
                                            (SEQ ID No: 54)
5'- TTTTTTTTTTTTTTTTTTTTAAAT AGC GGA TGC TAA GGA

CGA CTTGTCGTCGTCGTCCTTGTAGTC GGTTGGGGCGGATGC

ACTCCC-3'

Reverse Frame 1 (translation of the coding
strand complementary to the primer):
                                    (SEQ ID Nos: 55 and 92)
1 G S A S A P T D Y K D D D D K S S L A S A I (STOP) K K K K K K
```

Reaction Set Up:

| 10X Herculase Buffer (Strategene) | 50 µl |
| 10 mM dNTP | 10 µl |
| S7 (5 µM) | 20 µl |
| S5-1 (5 µM) | 20 µl |
| VH library (1-6 families) | 40 ng |
| H2O | X µl |
| Herculase (Strategene) | 10 µl |
| | 500 µl (50 µl/reaction) |

Temperature Cycling Program:

| 95 C./3 minutes | 1 cycle |
| 95 C./30 seconds | |
| 50 C./30 seconds | 20 cycles |
| 72 C./1 minutes | |
| 72 C./10 minutes | 1 cycle |

Tm of 50 C is approximate and depends on a choice of PCR primers.

Library Purification:

Amplified VH library DNAs were separated on 2% agarose gel. The 400 bp band was cut out under UV light for DNA extraction from the gel slice using Qiaquick Gel Extraction Kit (Qiagen #28706, Valencia, Calif.) and reconstitution in 300 µl H$_2$O. 5 µL of purified DNA was applied for electrophoresis on a 2% E-gel. The recovery rate was expected to be ~80%.

Transcription

Reaction Set-Up (MEGAscript Kit™, Ambion PH 1334, Foster City, Calif.)

For first round of library production, a full scale of RNA transcription (500 µl) is recommended. The reaction volume can be scaled down at later rounds.

| PCR product (5-10 µg) | 200 µL |
| 10X reaction buffer | 50 µL |
| ATP (75 mM) | 50 µL |
| CTP (75 mM) | 50 µL |
| GTP (75 mM) | 50 µL |
| UTP (75 mM) | 50 µL |
| T7 polymerase | 50 µL |
| Total: | 500 µL |

Incubation

The reaction mixture as above was incubated at 37° C. for 1-2 hrs or, preferably, up to overnight.

Purification

An exemplary purification method is fractionation on a NAP-25 column, which is given below. NAP 10 and NAP 5 columns can be used for purification of small scale production, in which cases the fraction volume should be changed accordingly.

For a purification process using a NAP-25 column, 25 µL Dnase I can be added to every 500 µl transcription reaction. The mixture will be incubated at 37° C. for 15 minutes before phenol extraction, when 500 µL phenol-chloroform-isoamylalcohol is added to the mixture. The mixture can be then vortexed for 30 seconds. After microfuging the mixture for 5 minutes, the aqueous phase can be then recovered. Before loading of this aqueous phase, a NAP-25 column can be pre-washed by letting 10 mL dH$_2$O drip through the column. Then the extracted transcription mix can be loaded with to washed column and run into the column. 800 µL dH$_2$O can then be added to column and the run-through can be collected. This elution process can be repeated for five times (E1-E5) and the RNA concentration in collected sample can be measured by A$_{260}$ on a spectrophotometer. 2 µL of sample can be applied for electrophoresis on a 2% E-gel to QC. The fraction containing most RNA can be used for ligation (E3 contains little amount, E4 is the peak fraction, E5 contains the mixture of RNA and free NTPs).

To calculate the concentration of RNA, 5 µl of each elution can be mixed with 995 µl of H$_2$O before measuring the OD of the mixture.

$$\text{nmol of } RNA = \frac{OD \times 40 \times 800 \; \mu l \times 1000}{330 \times 400 \times 5 \; \mu l}$$

An alternative RNA purification procedure (LiCl precipitation) is exemplified below:

500 µL 10 M LiCl can be added to every 500 µl transcription reaction before freezing the mixture at −20° C. for 30 minutes to 1 hour. The mixture can then be applied for centrifugation at maximum speed for 20 minutes. The resulting supernatant will be discarded, while the pellet can be resuspended in 50 µl of 3M NaOAc and 50 µL of dH2O. A standard EtOH precipitation can be performed. The resulting pellet can be dissolved in 100 µL of dH2O and the RNA concentration can then be measured using Qubit.

Photocrosslinking

Two types of Psoralen linkers are used: a 2'O-Me RNA linker PBI and a DNA linker DDB-1 that contain a biotin moiety to be used for streptavidin assembly.

XB-PBI (SA/DNA display linker OMe RNA/DNA):
(SEQ ID NO: 63)
5'-(Psoralen C6) u agc gga (Biotin-dT)gc uaa ggA CGA-3'

XB-DDB-1 (DNA display linker):
(SEQ ID NO: 64)
5'-(Psoralen C6) (C7-NH2-EZ biotin) T AGC GGA TGC TAA GGA CGA-3'

Psoralen C6
u,a,g,c=2-MeO-RNA
A,C,G=standard deoxy amidites
C7-NH2-amino spacer 7
EZ-biotin, Pierce EZ-link TFP-spacer-biotin
Reverse Frame 1 (translation of the linker region as appears in a coding strand): S S LAS A (SEQ ID NO: 65)
**Linker is light-sensitive and needs to be protected from light with aluminum foil etc.)

In the reaction set-up, the ratio of Linker/RNA can be from 1.5:1 (maximum) to 1.1:1 (sufficient).

In Round 1 reaction, a large scale production is suggested (1-2 nmol of RNA) to cover enough diversity. In later rounds, RNA input may be reduced to 100-600 pmol.

| RNA | 1 nmol |
| linker (1 mM) | 1.1 µL |
| 10 X chemical ligation buffer | 10 µL |
| adding dH$_2$O to | 100 µL (10 pmol RNA/µL final) |

(The final concentration of RNA in ligation reaction works from 3-15 pmol/ul. Ligation reaction volume can be varied.)

For annealing in a PCR thermocycler, the sample can be incubated at 85° C. for 30 seconds and to 4° C. at the rate of 0.3° C./second.

For irradiating, 1 µL of 100 mM DTT can be added to the annealed ligation mix. The mix can be transferred to a thin wall 0.5 ml eppendorf tube or kept in the same PCR tube. The irradiating process can be done with a handheld multiwavelength UV Lamp (Uvp.com (Upland, Calif.) #UVGL-25) on 'long wave' (365 nm) for 6 minutes at room temperature. About 50-90% RNA will be expected to be ligated with the requirement of purification.

For QC of ligated RNA, a sample can be applied for electrophoresis on a 6% TBU gel to check the ligation efficiency. Specifically, the 6% TBU gel can be pre-run under 300V for 15 minutes, followed by removing the comb and flushing the wells thoroughly. Then for each well about 10-15 pmol of free or ligated RNA can be mixed with 2× loading buffer (from transcription kit) and heated together at 90° C. for 3 minutes, followed by chilling on ice. Both pre-heated free and ligated RNA can then be loaded in wells of pre-heated gel for electrophoresis at 300V until the blue dye reaches the bottom.

Figure 30:
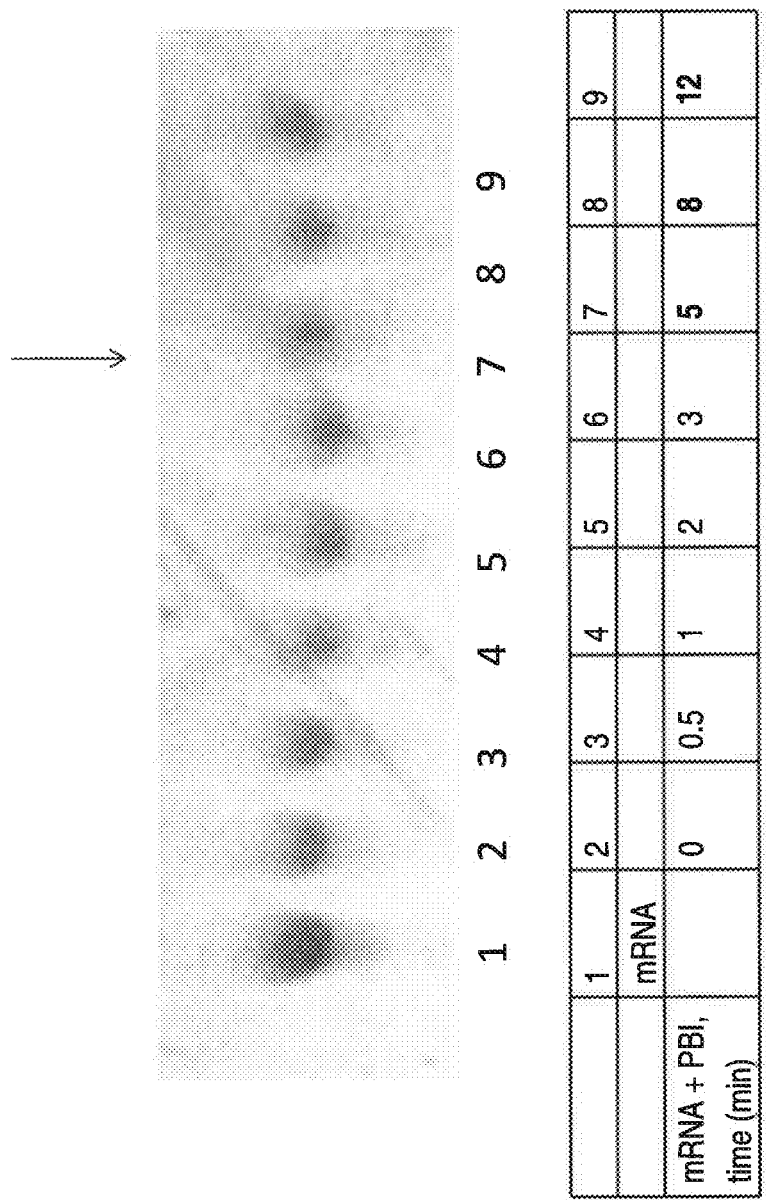
FIG. 30 illustrates an exemplary result of mRNA transcription, purification and crosslinking process.

An exemplary experiment was carried out as in FIG. 30. Specifically, KDR mRNA was in vitro transcribed and purified from the reaction by LiCl precipitation. One equivalent of PBI linker was annealed to mRNA sample by heating to 85° C. followed by slow cooling to 4° C. in 1× X-link buffer. DTT was added to final concentration of 1 mM. The samples were incubated at 365 nm wavelength for different amounts of time and then resolved on a 6% TBU denaturing gel. The image is UV shadowing of the gel. As shown in FIG. 30, the crosslinking is observed after 5 min irradiation (Lane 7). Further a 6 min irradiation was used for photocrosslinking.

Loading of Streptavidin

Streptavidin is a remarkably stable tetrameric protein which binds its ligand biotin at an exceptionally high affinity, Kd of $10^{-15}$ M.

A. With PBI Linkers

Due to high Tm of 0-Me RNA portion of PBI linker to RNA, it is recommended to dilute the original 100 mM NaCl buffer (as in 1× X-link buffer) to 10-20 mM salt, which is 5-10× dilution with water. ½ to ¼ equivalent of streptavidine (Prozyme, San Leandro, Calif.) solution can be added in either PBS or 1× X-link buffer, e.g., 1-2 µM final concentration of streptavidine for 4 µM X-linked RNA. Then 1 µL of RNAsine can be added and the mixture can be incubated at 48° C. in a heat block for 1 hour.

B. With DDB Linkers

Since a DDB linker is an all-DNA molecule, no dilution of the 1× X-link buffer (100 mM NaCl) is required. The DDB linker can accommodate better SA loading, and it is possible to use only 1.5-2× excess of the crosslinked mRNA to streptavidine. ½ or 1:1.5 equivalent of streptavidine (Prozyme, San Leandro, Calif.) solution can be added in either PBS or 1× X-link buffer, e.g., 2-2.5 µM final concentration of streptavidine for 4 µM X-linked RNA. Then 1 µL of RNAsine can be added and the mixture can be incubated at 48° C. in a heat block for 1 hour.

In each case (A or B) at least over 50% and up to 80% streptavidine can be expected to be loaded.

Loading of Puromycin Linker BPP

BPP: 5' Biotin-BB Cy3-(spacer 18)4-CC Pu
BPP-8: 5' Biotin-BB Cy3-(spacer 18)8-CC Pu
Cy3 dye
4 or 8 units of Spacer 18
Pu=Puromycin-CPG A BPP linker contains puromycin, a peptide acceptor molecule at the 3' end (the peptide acceptor enters the A site of the ribosome and covalently couple to the COOH terminus of the nascent polypeptide chain). The linker has biotin at 5' end which binds to streptavidine molecule loaded on each X-linked mRNA molecule. This peptide acceptor will ultimately enable the non-covalent tight association of the mRNA (genotype) to the protein encoded by this mRNA (phenotype). Each version of a BPP linker (with a shorter 4× spacer-18 or with a longer 8× spacer-18) contains a fluorescent Cy-3 dye moiety (Ex. 550, Em. 570 nm) for visualization. Other fluorescent dyes can be used instead of Cy-3, such as Fluoresceins, BODIPY, Cy-5, rhodamines etc.

Specifically, 1 equivalent of a corresponding BPP linker (relative to the amount of streptavidine) can be added to a loaded streptavidine-mRNA assembly. The mixture can be incubated for 15 minutes at room temperature. Almost 100% of BPP linker to streptavidine can be expected for binding.

Figure 31:
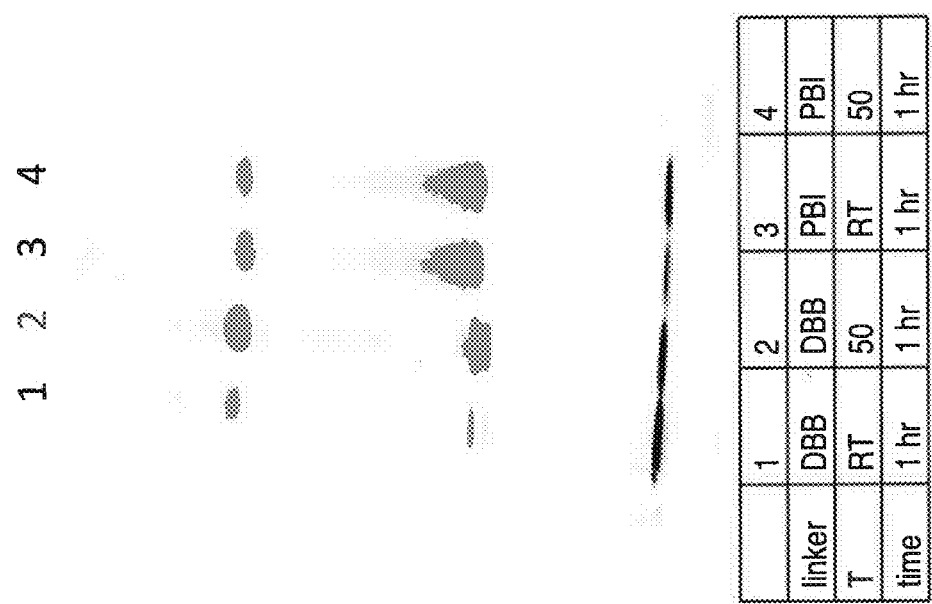
FIG. 31 illustrates an exemplary result of mRNA transcription, purification and streptavidine loading process.

An exemplary experiment was carried out as in FIG. 31. Specifically, KDR mRNA was in vitro transcribed and purified from the reaction by LiCl precipitation. One equivalent of either PBI or DDB linker was annealed to mRNA sample by heating to 85° C. followed by slow cooling to 4° C. in 1× X-link buffer, containing 100 mM NaCl. Sample of PBI-x-linked mRNA was then diluted 5× to final NaCl concentration of 20 mM. Sample of DDB-x-linked mRNA was used undiluted. For streptavidine loading, about ½ equivalent of streptavidin was added to each sample, followed by 1 hour incubation at either room temperature or at 50 C. Then BPP-Cy3 linker was added to each sample in amount, equivalent to streptavidine. After 15 min incubation at room temperature the resulting assemblies were resolved on a 4-16% NativePage.

Optional Step: Purification of the SA Assembly on Oligo dT Column

Since mRNA contains a tail of 20 As, it can be purified on an oligo dT column at this step. This purification is not absolutely necessary, but may somewhat improve the fusion yield at the next step.

Assembly Purification

Equal volume of 2× oligo dT binding buffer (200 mM Tris, pH 8, 2 M NaCl, 20 mM EDTA, 0.1% Triton) can be added to the prepared mRNA-SA assembly. Then oligo-dT cellulose can be added into the mixture (100 mg treated/washed oligo dT cellulose (1 mL of slurry) is sufficient to capture up to 1 nmol RNA input) before rocking at 4° C. for 30-60 minutes. The mixture can be spilled in a bench top centrifuge at 1500 rpm for 3 minutes at 4° C. The resulting supernatant will be discarded. The resulting pellet can be resuspended in 700 µL of oligo dT wash buffer (100 mM Tris pH 8, 1 M NaCl, No EDTA, 0.05% Triton x-100), loaded onto a drip/spin column (BioRad #732-6204, Hercules, Calif.) and then spilled in a microfuge at 1000 rpm for 10 seconds. The column can be washed with 700 µL oligo dT wash buffer and spilled at 1000 rpm for 10 more seconds. The wash step can be repeated for 8 times (during each wash, the centrifuging rpm and time may be increased if it is getting hard to spin through the wash buffer, but do not exceed 1500 rpm). 5 µL of the last wash can be collected for counting. Then the mRNA-SA assembly can be eluted with dH$_2$O. 60 µL dH$_2$O can be used for E1, followed by spinning at 1500 rpm for 10 seconds (5 µL used for counting). For E2, 500 µL dH$_2$O can be added to the column. After incubation for 5 min at room temp, E2 can be collected after spinning at 4000 rpm for 20 seconds (5 µL used for counting). For E3, 300 µL dH$_2$O can be added to and incubated with the column for 5 minutes at room temp. E3 can then be collected after spinning at 4000 rpm for 20 seconds (5 µL used for counting). In this Example, E2 contains 80% of the mRNA-SA assembly.

Translation

The translation volume can be varied based on the amount of RNA input. An exemplary condition is given below:

Translation Set-Up (300 µL)
RNA-SA assembly 120 pmol+H$_2$O 82 µl (or to 300 µL)
Amino acid master mix (-met) 15 µl

| | |
|---|---|
| 10 mM Methionine | 3 µl |
| Lysate | 200 µl |
| Total volume | 300 µl |

The mixture can be incubated at 30° C. in water bath or an incubator (in water block) for 45 minutes to 1 hour.

Fusion Formation

100 µL 2 M KCl (500 mM final) can be mixed with 20 µL 1M MgCl$_2$ (50 mM final) and incubated at room temperature for 1 hour. The resulting mixture can be optionally frozen and stored at −20° C. for up to several days. Also, freezing somewhat improves fusion yield.

Then 50 µL 0.5M EDTA can be added to this mixture to disassemble the ribosomes and produce ribosome-free fusions (10 µL saved for QC).

As an exemplary translation scale for selection, 1.2 nmol RNA (10×300 µL) for Round 1, 600 pmol RNA (5×300 µL) for Round 2 and 120-600 pmol RNA (1-5×300 µL) for Round 3 and on.

Fusion Purification by Oligo dT Cellulose: PBI Linker

Oligo dT purification allows purification of RNA fusion molecules (plus RNA) and removes free protein molecules generated by in vitro translation. This procedure and the following Reverse Transcription step should be used when PBI linker assembly is translated. In case of DDB-linker assembly a different procedure is recommended.

Fusion Purification

Equal volume of 2× oligo dT binding buffer (200 mM Tris, pH 8, 2 M NaCl, 20 mM EDTA, 0.1% Triton) can be added to translation/fusion mix. The oligo-dT cellulose (100 mg treated/washed oligo dT cellulose (1 mL of slurry) is sufficient to capture translation/fusion up to 1 nmol RNA input) can then be added to the mixture before rocking at 4° C. for 30-60 minutes. After spinning in a bench top centrifuge at 1500 rpm for 3 minutes at 4° C., the resulting supernatant will be discarded. The resulting pellet can be resuspended in 700 µL oligo dT wash buffer (100 mM Tris pH 8, 1 M NaCl, No EDTA, 0.05% Triton x-100) and loaded onto a drip/spin column (BioRad #732-6204, Hercules, Calif.), followed by spinning in a microfuge at 1000 rpm for 10 seconds. The resulting pellet can be resuspended in 700

μL oligo dT wash buffer before spinning at 1000 rpm for 10 seconds to reprecipitate the pellet. This wash step can be repeated for 8 times (during each wash, the centrifuging rpm and time may be increased if it is getting hard to spin through the wash buffer, but do not exceed 1500 rpm). 5 μL of the last wash can be collected for counting. After washing, dH$_2$O can be used for elution. For example, 60 μL dH$_2$O can be used for E1, followed by spinning at 1500 rpm for 10 seconds (5 μL used for counting). For E2, 500 μL dH$_2$O can be added to the column. After incubation for 5 min at room temp, E2 can be collected after spinning at 4000 rpm for 20 seconds (5 μL used for counting). For E3, 300 μL dH$_2$O can be added to and incubated with the column for 5 minutes at room temp. E3 can then be collected after spinning at 4000 rpm for 20 seconds (5 μL used for counting). In this Example, E2 contains 80% of the mRNA-SA assembly.

Estimation of Fusion Production:

The elution of fusions from the oligo dT cellulose can be further analyzed by methods known in the art, e.g., gel-electrophoresis, fluorescence densitometry, or radiolabel counting, etc.

Reverse Transcription: PBI Linker

RNA-cDNA hybrid is made to stabilize and reduce the secondary structure of the RNA and to serve as a template for PCR after selection. In the case of PBI linker, reverse transcription is preferred from an external primer (S6), but at a lower efficiency can be done from PBI linker itself, since four 3' nucleotides of the linker are DNA. This can potentially convert the assembly into DNA-displayed fusions, though we use a different all-DNA linker, DDB, for that purpose.

External RT Primer:

XB-S6-1:
(SEQ ID No: 56)
5'-TTAAAT AGC GGA TGC TAA GGA CGA
CTTGTCGTCGTCGTCCTTGTAGTC GGTTGGGGCGGATGCACTCCC-3'

Reverse Frame 1:
(SEQ ID No: 57)
G S A S A P T D Y K D D D D K S S L A S A I (STOP)

Reaction Set-Up:
(Invitrogen Reverse Transcription Kit)

The oligo-dT elutions can be spilled at 10000 rpm for 30 seconds to remove residual cellulose.

| | |
|---|---|
| E2 + E3 supernatant from spin: (10-20 μL E2 collected for electrophoresis on gel) | 800 μl (<1000 pmol total) |
| RT primer (S6-1) 1 mM | 1 μl (1000 pmol) |
| 5 x first strand buffer | 220 μl |
| 0.1M DTT | 11 μl (final 1 mM) |
| 25 mM dNTPs | 22 μl (0.5 mM final each) |
| Superscript II | 25 μl |
| H$_2$O | 21 μl |
| Total | 1100 μl |

Incubate at 37° C. for 45-60 min (remove 10 μL to run on gel).

QC: cDNA synthesis can be monitored by gel electrophoresis using NativePage and detected by fluorescence of the Cy-3 dye.

Fusion Purification by Oligo dT Cellulose, Coupled with the Reverse Transcription and RNAseH Digest: DDB Linker By performing Oligo dT purification and reverse transcription on the column in the mRNA-SA assembly with DDB linker we generate a DNA-displayed fusions. DDB in this case serves as an RT primer. The same procedure could be applied to PBI linker, which is also designed to serve as an internal RT primer, but demonstrated a lower efficiency compared to DDB.

DNA-displayed fusions demonstrate a great stability to nuclease digest and are used for cell-based and in vivo selections.

Fusion Immobilization on the Oligo dT Cellulose

The equal volume of 2x oligo dT binding buffer (200 mM Tris, pH 8, 2 M NaCl, 20 mM EDTA, 0.1% Triton) can be added to translation/fusion mix. The oligo-dT cellulose (100 mg treated/washed oligo dT cellulose (1 mL of slurry) is sufficient to capture translation/fusion up to 1 nmol RNA input) can then be further added before rocking at 4° C. for 30-60 minutes. After spinning in a bench top centrifuge at 1500 rpm for 3 minutes at 4° C., the resulting supernatant will be discarded. The resulting pellet can be resuspended in 700 μL oligo dT wash buffer (100 mM Tris pH 8, 1 M NaCl, No EDTA, 0.05% Triton x-100) and loaded onto a drip/spin column (BioRad #732-6204, Hercules, Calif.), followed by spinning in a microfuge at 1000 rpm for 10 seconds. The column is washed with 700 μL oligo dT wash buffer, followed by spinning at 1000 rpm for 10 seconds. The resulting pellet can be washed repeatedly for 8 times (during each wash, the centrifuging rpm and time may be increased if it is getting hard to spin through the wash buffer, but do not exceed 1500 rpm). 5 μL of the last wash will be collected for counting.

Reverse Transcription on the Oligo dT Cellulose

The oligo dT resin with immobilized fusions can be equilibrated in 1x first strand buffer (prepare separately). The buffer contains 75 mM KCl and 3 mM MgCl$_2$, which prevents elution of the fusions from the resin.

A mix can be prepared for the reverse transcription as following and then incubated at 37-39° C. for 60-75 minutes.

| | |
|---|---|
| Water | 695 μl |
| 5 x first strand buffer | 200 μl |
| 0.1M DTT | 10 μl (1 mM final) |
| 25 mM dNTPs | 40 μl (1 mM final each) |
| Superscript II | 50 μl |
| RNasin | 5 μl |
| Total | 1000 μl |

(In this example there is no external RT primer added. There is increased amount of dNTPs and SSII reverse transcriptase.)

At this step the strand of cDNA is built which is covalently bound to the biotin moiety and in turn tightly non-covalently attached to the streptavidine-BPP-fusion sandwich, thus forming a precursor to DNA-displayed fusions.

RNAse H Digest of the RNA Strand and Elution from the Oligo dT Cellulose

Following the reverse transcription step, to the same column a corresponding amount of RNAse H can be added (10 μL of RNAse H (2 U/μL, Invitrogen, Carlsbad, Calif.)) for a 1000 μL reaction described above). Incubate for an additional 1 hour at 37° C.

The single-stranded DNA-fusions can be eluted by spinning down the oligo dT column at 2000 rpm for 1 minute and then washed with 500 μL of 1x first strand buffer. In this Example around 80-95% of the material can be eluted from the column.

Figure 32:
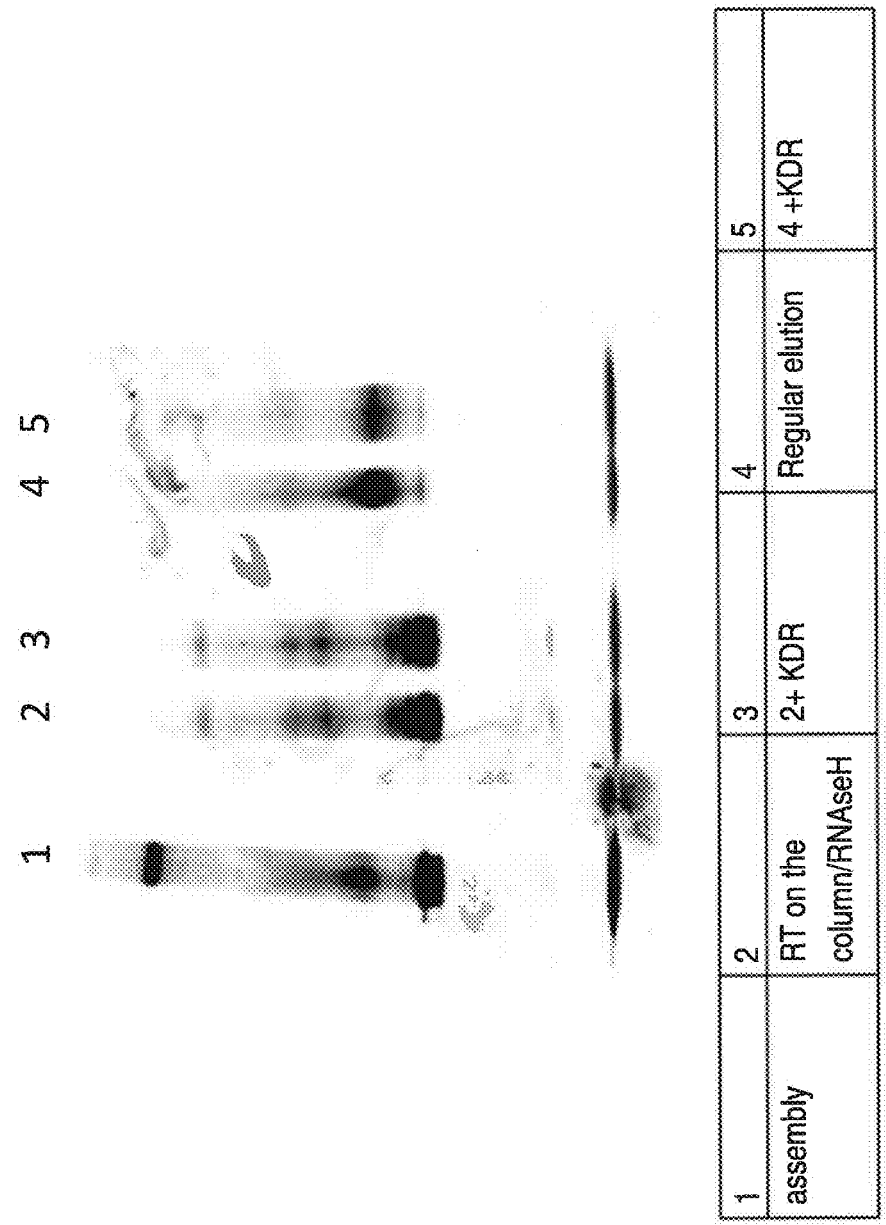
FIG. 32 illustrates an exemplary result after RNaseH treatment and elution process.
Figure 33:
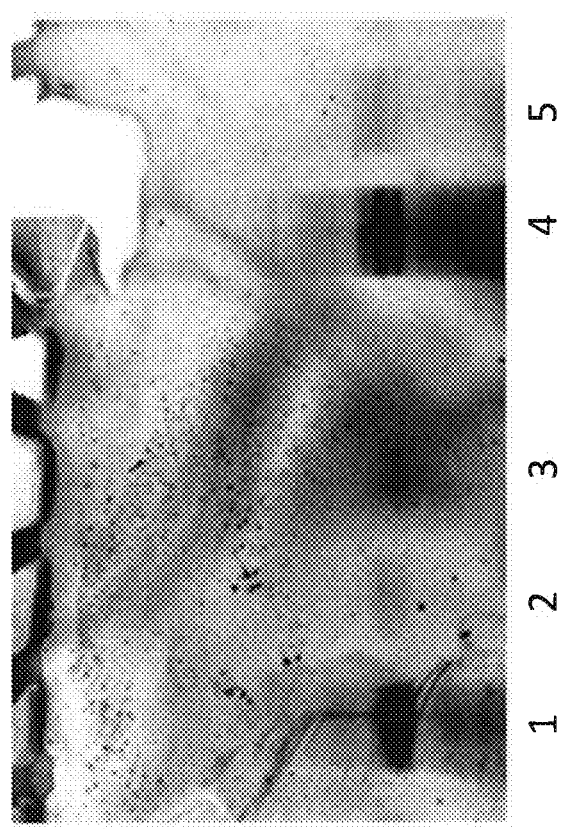
FIG. 33 illustrates an exemplary result after RNaseH treatment and elution process.

Exemplary experiments were carried out as in FIGS. 32 and 33. As shown in FIG. 32, DNA display assembly (mRNA-xlinked with DDB linker) was translated in RRL for 1 hour at 30° C. at mRNA concentration of 200 nM. The product was loaded on oligo-dT column (Lane 2-3). The column was washed several times with 1× oligo-dT buffer and then two times with 1× RT buffer, followed by dNTPs addition and SSII RT for 1 hour at 37° C. RNaseH treatment was further carried out for another 1 hour at 37° C. The column was eluted by spinning down (spin filter). In Lanes 4 and 5, mRNA assemblies with PBI linker were translated similarly to the above, following by treatment with oligo dT resin and elution with 5 mM Tris pH 7.0.

In FIG. 33, DNA display assembly (mRNA-xlinked with DDB linker, lanes 1, 2, and 3, or BPP linker, Lanes 4 and 5 (BPP-8 linker)) was translated in RRL for 1 hour at 30° C. at mRNA concentration of 200 nM. The product was loaded on oligo-dT column. The column was washed several times with 1× oligo-dT buffer and then 2× with 1× RT buffer, followed by dNTPs addition and SSII RT for 1 hour at 37° C. RNaseH treatment was further carried out for another 1 hour at 37° C. The column was eluted by spinning down (spin filter). The fusions then were purified on an anti Flag M2 agarose (Lanes 2, 3 and 5).

$2^{nd}$ Strand Synthesis and Completion of the DNA-Display Fusion Assembly.

```
XB_S7 (T7TMVUTR2 42-mer; 5' PCR primer
for both VH IgM, IgG libraries):
                                    (SEQ ID No: 52)
5'-TAATACGACTCACTATAGGGACAATTACTATTTACAATTACA-3'

XB_S7a (T7TMV primer 45 mer with additional
ATG, improves Tm by 3 C):
                                    (SEQ ID No: 58)
5'-TAATACGACTCACTATAGGGACAATTACTATTTACAATTACAAT
G-3'
```

To the elution from the previous step, extra dNTPs and SSII RT can be added, together with 1-1.5 equivalent of the TMV-T7 primer S7 or S7a.

An exemplary reaction includes mixing additional reagents per 1500 μL reaction, as described above:

| | |
|---|---|
| S7 or S7a | 1-1.5 equvalent |
| SSII RT | 10 μL |
| dNTP | 10 μL |

The mixture can be incubated for an additional 1 hour at 37-39° C. After the synthesis of the $2^{nd}$ strand the DNA displayed fusion assembly is complete and following additional purification on an anti FLAG antibody resin, the fusions can be used for cell-based or in vivo selections.

Figure 34:
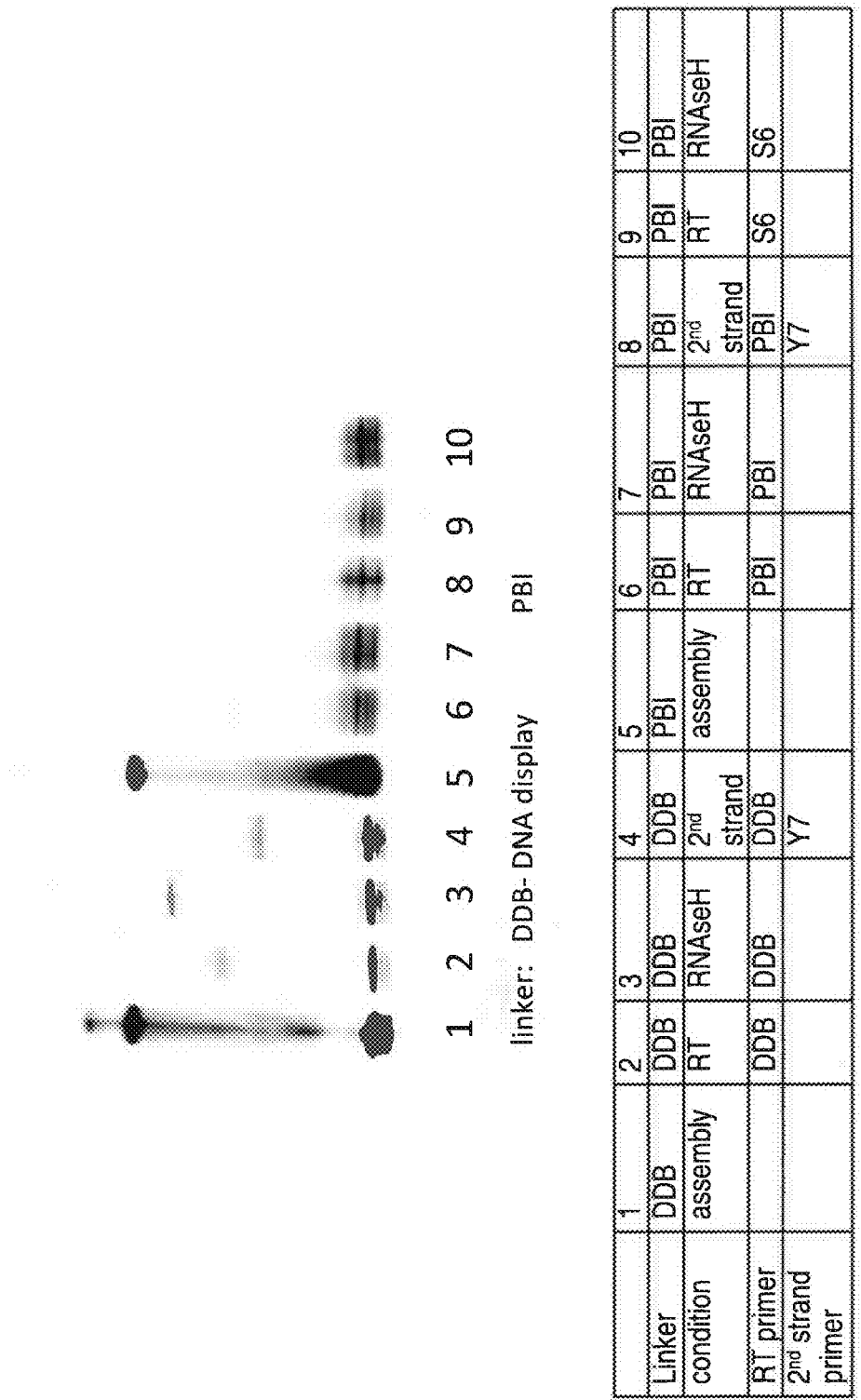
FIG. 34 illustrates an exemplary result after RT-PCR and $2^{nd}$ strand synthesis process.

An exemplary experiment is shown as in FIG. 34. The mRNA assembly was carried out as following: 4 μM RNA and 4 μM linker (DDB or PBI) were annealed 85 to 4° C. in 1× X-link buffer; then DTT was added to 1 mM and UV 365 for 6 min. Then SA was loaded as 1:2 ratio (final mRNA at 2 μM and SA at 1 μM) in 0.67× X-link buffer at 48° C. for 1 hour. Puromycin Cy3 linker (BPP-4×C18 spacer) was added at 1 μM to the assembly for 10 minutes at RT (room temperature). No oligo dT purification was performed. The following RT reaction was carried out as following: standard RT using superscript II (SSII) at 42° C. using 3 conditions: DDB as RT primer, PBI as RT primer and S6 (external primer) in PBI assembly only. Each of the RT reactions were treated by RNAse H (2 U) for 1 hour at 37° C. Further, the second strand was synthesized by adding Y7 primer (T7-TMV) 1:1 and extra SSII RT enzyme and extra dNTPs for 1 hour at 42° C. (conditions taken from Kurtz, Chembiochem 2001).

FLAG-Tag Purification

Flag purification recovers only full length protein molecules and removes any free RNA and truncated protein molecules generated by in vitro translation.

Binding and Wash:

500 μL M2 agarose (10 mM Gly pH 3.5 pre-stripped and pre-blocked in 1× binding buffer) suspension can be transferred to a 2 ml tube. After spinning in a microfuge at 1500 rpm for 1 minute, the resulting supernatant will be discarded. The agarose can be further washed twice with 1 mL flag binding buffer. The washed M2-agarose can then be mixed together with prepared chemically modified library (5 μl used for counting) and ¼ library volume of 5× flag binding buffer and rocked at 4° C. for 1 hour to overnight. After spinning in a microfuge at 1500 rpm for 1 minute, the resulting supernatant will be transferred to a fresh tube, while the resulting M2 agarose pellet will be resuspend in 0.7 mL flag binding buffer and loaded onto a drip spin column. The loaded column can be spinned in a microfuge at 1000 rpm for 10 seconds and further washed 6 times with 0.7 ml flag binding buffer, followed by spinning at 1000 rpm for 10 seconds. Then the column can be washed twice with 0.7 ml 1× binding buffer, followed by spinning at 1000 rpm for 10 seconds. (5 μL of last wash can be collected for counting).

Elution:

500 μL of 100 μg/mL FLAG peptide in 1× binding buffer can be added to the column. After incubating for 5 minutes, the column can be spinning at 3000 rpm before collecting the elution. The elution process can be repeated with 300 μl flag peptide (5 μL of each elution can be collected for counting).

Estimation of Recovery:

Routinely the recovery rate can be around 10-30%. The recovery can be measured by fluorescence or other methods known in the art.

PCR

Depending on the purpose, Taq polymerase or high fidelity polymerase can be used for amplification. Small scale PCR is recommended to check out the PCR cycles to prevent PCR artifacts usually caused by over amplification.

Reaction Set-Up:

| | |
|---|---|
| 10X Herculase Buffer (Strategene) | 2.5 μl |
| 10 mM dNTP | 0.5 μl |
| T7 TMV UTR (5 μM) | 1 μl |
| Cμ2flagA20 (5 μM) | 1 μl |
| Template | 2.5 μl |
| H₂O | 17 μl |
| Herculase (Stratagene) | 0.5 μl |
| | 25 μl |

Note: The fractions collected in previous steps, e.g., flow-through, last wash, Elution 1, and Elution 2, can be used as template for PCR. Specifically, 2.5-5 μL of template can be used in this PCR reaction, especially for early selection rounds (round 1-3, for example). However, it may be helpful to use less. An exemplary PCR condition is listed below:

| | |
|---|---|
| 95° C. for 3 minutes | 1 cycle |
| 95° C. for 30 seconds | |
| 50° C. for 30 seconds | X cycles (X = 15, 20, or 25 depending on the signal) |
| 72° C. for 1 minute | |
| 72° C. for 5 minutes | 1 cycle |

Note on Tm: Tm is calculated to the primer. In this Example, primers can have Tms higher than 50° C. or 52 to 65° C.

After the PCR reaction, 5 µL of reaction mixture can be used for electrophoresis on a 2% E-gel. A major band having a size of ~400 bp can be expected on the gel. If the quality of small-scale PCR is acceptable, the rest of elution can be used as template for large-scale PCR under the similar conditions.

DNA Purification:

Sometimes it may be necessary to purify the PCR product. After electrophoresis, the gel slice on 2% agarose gel containing the PCR product (the 400 bp band) can be cut out under UV light. DNA can then be extracted from the gel slice using Qiaquick Gel Extraction Kit (Qiagen #28706, Valencia, Calif.). 5 µL of purified DNA can be used for electrophoresis on a 2% E-gel. Usually ~80% recovery can be expected.

Tagging for 454 Sequencing: DNA Display

For the tagging of individual molecules at non-amplification selection step the following 2$^{nd}$ strand primer is used:

(SEQ ID No: 59)
GCCTCCCTCGCGCCATCAGNNNNNNGGGACAATTACTATTTACAATTACA
ATG

This primer contains TMV sequence, a 454 adaptor sequence and N6 random tag. The corresponding PCR primer for the 3' end (contains a second 454 adaptor, Tm of gene-specific part is 50.4 C)

(SEQ ID No: 60)
GCCTTGCCAGCCCGCTCAGTAGCGGATGCTAAGCACGA

Amplicon preparation is performed using adaptor primers only:

Forward: Tm 64.7° C.
(SEQ ID No: 61)
GCCTCCCTCGCGCCATCAG

Reverse: Tm 65.7° C.
(SEQ ID No: 62)
GCCTTGCCAGCCCGCTCAG

Tm of both are around 65° C., thus RACE type of PCR is possible for a 3' primer.

EQUIVALENTS

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations, web pages, figures and/or appendices, regardless of the format of such literature and similar materials, are expressly incorporated by reference in their entirety. In the event that one or more of the incorporated literature and similar materials differs from or contradicts this application, including defined terms, term usage, described techniques, or the like, this application controls. Such equivalents are intended to be encompassed by the following claims.

We claim:

1. A method of producing a library of nucleic acid-polypeptide (X-display) complexes, comprising the steps of:
   (a) providing a library of mRNA sequences comprising a sequence element complementary to a first nucleic acid linker;
   (b) providing a first nucleic acid linker operably linked to a first high affinity ligand such that the first nucleic acid linker binds to the mRNA through complementary nucleic acid base pairing;
   (c) providing a second high affinity ligand operably linked to a peptide acceptor;
   (d) providing a ligand acceptor with at least two binding sites such that the ligand acceptor binds to the first high affinity ligand and the second high affinity ligand; and
   (e) allowing translation of the mRNA to occur such that the peptide acceptor binds to the translated protein, thereby forming a nucleic acid-polypeptide complex linking the mRNA to the protein.

2. The method of claim 1, further comprising allowing reverse transcription of the mRNA using the first nucleic acid linker in the nucleic acid-polypeptide complex as a primer such that a DNA/RNA hybrid is formed.

3. The method of claim 2, further comprising degrading the mRNA and synthesizing a complementary DNA strand thereby forming a DNA/DNA hybrid in the nucleic acid-polypeptide complex.

4. The method of claim 1 wherein the mRNA further comprises a tobacco mosaic virus (TMV) enhancer.

5. The method of claim 1 wherein the mRNA further comprises a Cμ sequence.

6. The method of claim 1 wherein the mRNA further comprises a FLAG tag.

7. The method of claim 1 wherein the mRNA further comprises a streptavidin (SA) display sequence.

8. The method of claim 1 wherein the mRNA further comprises an A20 tail.

* * * * *

SEQUENCE LISTING

```
<160> NUMBER OF SEQ ID NOS: 92

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
acaggagacg aggggggaaaa g                                              21

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
gccaggggga agaccgatgg                                                 20

<210> SEQ ID NO 3
<211> LENGTH: 22
```

```
<212> TYPE: DNA
<213> ORGANISM: Artificial Sequence
<220> FEATURE:
<223> OTHER INFORMATION: Synthetic

<400> SEQUENCE: 3
gaggctcagc gggaagacct tg                                              22

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
caactgctca tcagatggcg g                                               21

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
cagtgtggcc ttgttggctt g                                               21

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
ggttggggcg gatgcactcc c                                               21

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
cgatgggccc ttggtggarg c                                               21

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
cttggggctg gtcggggatg c                                               21

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
```
agatggtgca gccacagttc g                                         21

<210> SEQ ID NO 10
<211> LENGTH: 42
<212> TYPE: DNA
<213> ORGANISM: Artificial Sequence
<220> FEATURE:
<223> OTHER INFORMATION: Synthetic

<400> SEQUENCE: 10
agatggtgca gccacagttc gtaggacggt sascttggtc cc                  42

<210> SEQ ID NO 11
<211> LENGTH: 42
<212> TYPE: DNA
<213> ORGANISM: Artificial Sequence
<220> FEATURE:
<223> OTHER INFORMATION: Synthetic

<400> SEQUENCE: 11
agatggtgca gccacagttc ggaggacggt cagctgggtg cc                  42

<210> SEQ ID NO 12
<211> LENGTH: 46
<212> TYPE: DNA
<213> ORGANISM: Artificial Sequence
<220> FEATURE:
<223> OTHER INFORMATION: Synthetic

<400> SEQUENCE: 12
caattactat ttacaattac aatgcaggtk cagctggtgc agtctg              46

<210> SEQ ID NO 13
<211> LENGTH: 46
<212> TYPE: DNA
<213> ORGANISM: Artificial Sequence
<220> FEATURE:
<223> OTHER INFORMATION: Synthetic

<400> SEQUENCE: 13
caattactat ttacaattac aatgcaggtc cagcttgtgc agtctg              46

<210> SEQ ID NO 14
<211> LENGTH: 46
<212> TYPE: DNA
<213> ORGANISM: Artificial Sequence
<220> FEATURE:
<223> OTHER INFORMATION: Synthetic

<400> SEQUENCE: 14
caattactat ttacaattac aatgsaggtc cagctggtac agtctg              46

<210> SEQ ID NO 15
<211> LENGTH: 46
<212> TYPE: DNA
<213> ORGANISM: Artificial Sequence
<220> FEATURE:
<223> OTHER INFORMATION: Synthetic

<400> SEQUENCE: 15
caattactat ttacaattac aatgcaratg cagctggtgc agtctg              46

<210> SEQ ID NO 16
<211> LENGTH: 46
<212> TYPE: DNA
<213> ORGANISM: Artificial Sequence
<220> FEATURE:
<223> OTHER INFORMATION: Synthetic

<400> SEQUENCE: 16
caattactat ttacaattac aatgcagrtc accttgaagg agtctg        46

<210> SEQ ID NO 17
<211> LENGTH: 46
<212> TYPE: DNA
<213> ORGANISM: Artificial Sequence
<220> FEATURE:
<223> OTHER INFORMATION: Synthetic

<400> SEQUENCE: 17
caattactat ttacaattac aatggargtg cagctggtgg agtctg        46

<210> SEQ ID NO 18
<211> LENGTH: 46
<212> TYPE: DNA
<213> ORGANISM: Artificial Sequence
<220> FEATURE:
<223> OTHER INFORMATION: Synthetic

<400> SEQUENCE: 18
caattactat ttacaattac aatgcaggtg cagctggtgg agtctg        46

<210> SEQ ID NO 19
<211> LENGTH: 46
<212> TYPE: DNA
<213> ORGANISM: Artificial Sequence
<220> FEATURE:
<223> OTHER INFORMATION: Synthetic

<400> SEQUENCE: 19
caattactat ttacaattac aatggaggtg cagctgttgg agtctg        46

<210> SEQ ID NO 20
<211> LENGTH: 42
<212> TYPE: DNA
<213> ORGANISM: Artificial Sequence
<220> FEATURE:
<223> OTHER INFORMATION: Synthetic

<400> SEQUENCE: 20
caattactat ttacaattac aatgcagstg cagctgcagg ag        42

<210> SEQ ID NO 21
<211> LENGTH: 45
<212> TYPE: DNA
<213> ORGANISM: Artificial Sequence
<220> FEATURE:
<223> OTHER INFORMATION: Synthetic

<400> SEQUENCE: 21
caattactat ttacaattac aatgcaggtg cagctacagc agtgg        45

<210> SEQ ID NO 22
<211> LENGTH: 46
<212> TYPE: DNA
<213> ORGANISM: Artificial Sequence
<220> FEATURE:
<223> OTHER INFORMATION: Synthetic

<400> SEQUENCE: 22
caattactat ttacaattac aatggargtg cagctggtgc agtctg        46

<210> SEQ ID NO 23
<211> LENGTH: 46
<212> TYPE: DNA
<213> ORGANISM: Artificial Sequence
<220> FEATURE:
<223> OTHER INFORMATION: Synthetic

<400> SEQUENCE: 23
caattactat ttacaattac aatgcaggta cagctgcagc agtcag                46

<210> SEQ ID NO 24
<211> LENGTH: 46
<212> TYPE: DNA
<213> ORGANISM: Artificial Sequence
<220> FEATURE:
<223> OTHER INFORMATION: Synthetic

<400> SEQUENCE: 24
caattactat ttacaattac aatgcaggtg cagctggtgc aatctg                46

<210> SEQ ID NO 25
<211> LENGTH: 48
<212> TYPE: DNA
<213> ORGANISM: Artificial Sequence
<220> FEATURE:
<223> OTHER INFORMATION: Synthetic

<400> SEQUENCE: 25
ggcggaggtg gctctggcgg tggcggatcg racatccaga tgacccag              48

<210> SEQ ID NO 26
<211> LENGTH: 48
<212> TYPE: DNA
<213> ORGANISM: Artificial Sequence
<220> FEATURE:
<223> OTHER INFORMATION: Synthetic

<400> SEQUENCE: 26
ggcggaggtg gctctggcgg tggcggatcg gmcatccagt tgacccag              48

<210> SEQ ID NO 27
<211> LENGTH: 48
<212> TYPE: DNA
<213> ORGANISM: Artificial Sequence
<220> FEATURE:
<223> OTHER INFORMATION: Synthetic

<400> SEQUENCE: 27
ggcggaggtg gctctggcgg tggcggatcg gccatccrga tgacccag              48

<210> SEQ ID NO 28
<211> LENGTH: 48
<212> TYPE: DNA
<213> ORGANISM: Artificial Sequence
<220> FEATURE:
<223> OTHER INFORMATION: Synthetic

<400> SEQUENCE: 28
ggcggaggtg gctctggcgg tggcggatcg gtcatctgga tgacccag              48

<210> SEQ ID NO 29
<211> LENGTH: 48
<212> TYPE: DNA
<213> ORGANISM: Artificial Sequence
<220> FEATURE:
<223> OTHER INFORMATION: Synthetic

```
<400> SEQUENCE: 29
ggcggaggtg gctctggcgg tggcggatcg gatattgtga tgacccag          48

<210> SEQ ID NO 30
<211> LENGTH: 48
<212> TYPE: DNA
<213> ORGANISM: Artificial Sequence
<220> FEATURE:
<223> OTHER INFORMATION: Synthetic

<400> SEQUENCE: 30
ggcggaggtg gctctggcgg tggcggatcg gatrttgtga tgactcag          48

<210> SEQ ID NO 31
<211> LENGTH: 48
<212> TYPE: DNA
<213> ORGANISM: Artificial Sequence
<220> FEATURE:
<223> OTHER INFORMATION: Synthetic

<400> SEQUENCE: 31
ggcggaggtg gctctggcgg tggcggatcg gaaattgtgt tgacrcag          48

<210> SEQ ID NO 32
<211> LENGTH: 48
<212> TYPE: DNA
<213> ORGANISM: Artificial Sequence
<220> FEATURE:
<223> OTHER INFORMATION: Synthetic

<400> SEQUENCE: 32
ggcggaggtg gctctggcgg tggcggatcg gaaatagtga tgacgcag          48

<210> SEQ ID NO 33
<211> LENGTH: 48
<212> TYPE: DNA
<213> ORGANISM: Artificial Sequence
<220> FEATURE:
<223> OTHER INFORMATION: Synthetic

<400> SEQUENCE: 33
ggcggaggtg gctctggcgg tggcggatcg gaaattgtaa tgacacag          48

<210> SEQ ID NO 34
<211> LENGTH: 48
<212> TYPE: DNA
<213> ORGANISM: Artificial Sequence
<220> FEATURE:
<223> OTHER INFORMATION: Synthetic

<400> SEQUENCE: 34
ggcggaggtg gctctggcgg tggcggatcg gacatcgtga tgacccag          48

<210> SEQ ID NO 35
<211> LENGTH: 48
<212> TYPE: DNA
<213> ORGANISM: Artificial Sequence
<220> FEATURE:
<223> OTHER INFORMATION: Synthetic

<400> SEQUENCE: 35
ggcggaggtg gctctggcgg tggcggatcg gaaacgacac tcacgcag          48

<210> SEQ ID NO 36
```

<211> LENGTH: 48
<212> TYPE: DNA
<213> ORGANISM: Artificial Sequence
<220> FEATURE:
<223> OTHER INFORMATION: Synthetic

<400> SEQUENCE: 36
ggcggaggtg gctctggcgg tggcggatcg gaaattgtgc tgactcag           48

<210> SEQ ID NO 37
<211> LENGTH: 48
<212> TYPE: DNA
<213> ORGANISM: Artificial Sequence
<220> FEATURE:
<223> OTHER INFORMATION: Synthetic

<400> SEQUENCE: 37
ggcggaggtg gctctggcgg tggcggatcg gatgttgtga tgacacag           48

<210> SEQ ID NO 38
<211> LENGTH: 48
<212> TYPE: DNA
<213> ORGANISM: Artificial Sequence
<220> FEATURE:
<223> OTHER INFORMATION: Synthetic

<400> SEQUENCE: 38
ggcggaggtg gctctggcgg tggcggatcg cagtctgtgc tgackcag           48

<210> SEQ ID NO 39
<211> LENGTH: 48
<212> TYPE: DNA
<213> ORGANISM: Artificial Sequence
<220> FEATURE:
<223> OTHER INFORMATION: Synthetic

<400> SEQUENCE: 39
ggcggaggtg gctctggcgg tggcggatcg cagtctgtgy tgacgcag           48

<210> SEQ ID NO 40
<211> LENGTH: 48
<212> TYPE: DNA
<213> ORGANISM: Artificial Sequence
<220> FEATURE:
<223> OTHER INFORMATION: Synthetic

<400> SEQUENCE: 40
ggcggaggtg gctctggcgg tggcggatcg cagtctgccc tgactcag           48

<210> SEQ ID NO 41
<211> LENGTH: 48
<212> TYPE: DNA
<213> ORGANISM: Artificial Sequence
<220> FEATURE:
<223> OTHER INFORMATION: Synthetic

<400> SEQUENCE: 41
ggcggaggtg gctctggcgg tggcggatcg tcctatgwgc tgactcag           48

<210> SEQ ID NO 42
<211> LENGTH: 48
<212> TYPE: DNA
<213> ORGANISM: Artificial Sequence
<220> FEATURE:
<223> OTHER INFORMATION: Synthetic

<400> SEQUENCE: 42
ggcggaggtg gctctggcgg tggcggatcg tcctatgagc tgacacag        48

<210> SEQ ID NO 43
<211> LENGTH: 48
<212> TYPE: DNA
<213> ORGANISM: Artificial Sequence
<220> FEATURE:
<223> OTHER INFORMATION: Synthetic

<400> SEQUENCE: 43
ggcggaggtg gctctggcgg tggcggatcg tcttctgagc tgactcag        48

<210> SEQ ID NO 44
<211> LENGTH: 48
<212> TYPE: DNA
<213> ORGANISM: Artificial Sequence
<220> FEATURE:
<223> OTHER INFORMATION: Synthetic

<400> SEQUENCE: 44
ggcggaggtg gctctggcgg tggcggatcg tcctatgagc tgatgcag        48

<210> SEQ ID NO 45
<211> LENGTH: 48
<212> TYPE: DNA
<213> ORGANISM: Artificial Sequence
<220> FEATURE:
<223> OTHER INFORMATION: Synthetic

<400> SEQUENCE: 45
ggcggaggtg gctctggcgg tggcggatcg cagcytgtgc tgactcaa        48

<210> SEQ ID NO 46
<211> LENGTH: 48
<212> TYPE: DNA
<213> ORGANISM: Artificial Sequence
<220> FEATURE:
<223> OTHER INFORMATION: Synthetic

<400> SEQUENCE: 46
ggcggaggtg gctctggcgg tggcggatcg cagsctgtgc tgactcag        48

<210> SEQ ID NO 47
<211> LENGTH: 48
<212> TYPE: DNA
<213> ORGANISM: Artificial Sequence
<220> FEATURE:
<223> OTHER INFORMATION: Synthetic

<400> SEQUENCE: 47
ggcggaggtg gctctggcgg tggcggatcg aattttatgc tgactcag        48

<210> SEQ ID NO 48
<211> LENGTH: 48
<212> TYPE: DNA
<213> ORGANISM: Artificial Sequence
<220> FEATURE:
<223> OTHER INFORMATION: Synthetic

<400> SEQUENCE: 48
ggcggaggtg gctctggcgg tggcggatcg cagrctgtgg tgactcag        48

<210> SEQ ID NO 49
<211> LENGTH: 48
<212> TYPE: DNA

```
<213> ORGANISM: Artificial Sequence
<220> FEATURE:
<223> OTHER INFORMATION: Synthetic

<400> SEQUENCE: 49
ggcggaggtg gctctggcgg tggcggatcg cagactgtgg tgacccag          48

<210> SEQ ID NO 50
<211> LENGTH: 48
<212> TYPE: DNA
<213> ORGANISM: Artificial Sequence
<220> FEATURE:
<223> OTHER INFORMATION: Synthetic

<400> SEQUENCE: 50
ggcggaggtg gctctggcgg tggcggatcg cwgcctgtgc tgactcag           48

<210> SEQ ID NO 51
<211> LENGTH: 48
<212> TYPE: DNA
<213> ORGANISM: Artificial Sequence
<220> FEATURE:
<223> OTHER INFORMATION: Synthetic

<400> SEQUENCE: 51
ggcggaggtg gctctggcgg tggcggatcg caggcagggc tgactcag           48

<210> SEQ ID NO 52
<211> LENGTH: 42
<212> TYPE: DNA
<213> ORGANISM: Artificial Sequence
<220> FEATURE:
<223> OTHER INFORMATION: Synthetic

<400> SEQUENCE: 52
taatacgact cactataggg acaattacta tttacaatta ca                 42

<210> SEQ ID NO 53
<211> LENGTH: 45
<212> TYPE: DNA
<213> ORGANISM: Artificial Sequence
<220> FEATURE:
<223> OTHER INFORMATION: Synthetic

<400> SEQUENCE: 53
taatacgact cactataggg acaattacta tttacaatta caatg              45

<210> SEQ ID NO 54
<211> LENGTH: 87
<212> TYPE: DNA
<213> ORGANISM: Artificial Sequence
<220> FEATURE:
<223> OTHER INFORMATION: Synthetic

<400> SEQUENCE: 54
tttttttttt tttttttttt aaatagcgga tgctaaggac gacttgtcgt cgtcgtcctt    60
gtagtcggtt ggggcggatg cactccc                                       87

<210> SEQ ID NO 55
<211> LENGTH: 22
<212> TYPE: PRT
<213> ORGANISM: Artificial Sequence
<220> FEATURE:
<223> OTHER INFORMATION: Synthetic

<400> SEQUENCE: 55
```

Gly Ser Ala Ser Ala Pro Thr Asp Tyr Lys Asp Asp Asp Lys Ser
1               5                   10                  15

Ser Leu Ala Ser Ala Ile
            20

<210> SEQ ID NO 56
<211> LENGTH: 69
<212> TYPE: DNA
<213> ORGANISM: Artificial Sequence
<220> FEATURE:
<223> OTHER INFORMATION: Synthetic

<400> SEQUENCE: 56
ttaaatagcg gatgctaagg acgacttgtc gtcgtcgtcc ttgtagtcgg ttggggcgga    60
tgcactccc                                                           69

<210> SEQ ID NO 57
<211> LENGTH: 22
<212> TYPE: PRT
<213> ORGANISM: Artificial Sequence
<220> FEATURE:
<223> OTHER INFORMATION: Synthetic

<400> SEQUENCE: 57

Gly Ser Ala Ser Ala Pro Thr Asp Tyr Lys Asp Asp Asp Lys Ser
1               5                   10                  15

Ser Leu Ala Ser Ala Ile
            20

<210> SEQ ID NO 58
<211> LENGTH: 45
<212> TYPE: DNA
<213> ORGANISM: Artificial Sequence
<220> FEATURE:
<223> OTHER INFORMATION: Synthetic

<400> SEQUENCE: 58
taatacgact cactataggg acaattacta tttacaatta caatg                   45

<210> SEQ ID NO 59
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(25)
<223> OTHER INFORMATION: n is a, c, g, or t

<400> SEQUENCE: 59
gcctccctcg cgccatcagn nnnngggac aattactatt tacaattaca atg           53

<210> SEQ ID NO 60
<211> LENGTH: 38
<212> TYPE: DNA
<213> ORGANISM: Artificial Sequence
<220> FEATURE:
<223> OTHER INFORMATION: Synthetic

<400> SEQUENCE: 60
gccttgccag cccgctcagt agcggatgct aagcacga                           38

<210> SEQ ID NO 61

<210> SEQ ID NO 61
<211> LENGTH: 19
<212> TYPE: DNA
<213> ORGANISM: Artificial Sequence
<220> FEATURE:
<223> OTHER INFORMATION: Synthetic

<400> SEQUENCE: 61
gcctccctcg cgccatcag                                            19

<210> SEQ ID NO 62
<211> LENGTH: 19
<212> TYPE: DNA
<213> ORGANISM: Artificial Sequence
<220> FEATURE:
<223> OTHER INFORMATION: Synthetic

<400> SEQUENCE: 62
gccttgccag cccgctcag                                            19

<210> SEQ ID NO 63
<211> LENGTH: 18
<212> TYPE: RNA
<213> ORGANISM: Artificial Sequence
<220> FEATURE:
<223> OTHER INFORMATION: Synthetic

<400> SEQUENCE: 63
uagcggagcu aaggacga                                             18

<210> SEQ ID NO 64
<211> LENGTH: 19
<212> TYPE: DNA
<213> ORGANISM: Artificial Sequence
<220> FEATURE:
<223> OTHER INFORMATION: Synthetic

<400> SEQUENCE: 64
tagcggatgc taaggacga                                            19

<210> SEQ ID NO 65
<211> LENGTH: 6
<212> TYPE: PRT
<213> ORGANISM: Artificial Sequence
<220> FEATURE:
<223> OTHER INFORMATION: Synthetic

<400> SEQUENCE: 65

Ser Ser Leu Ala Ser Ala
1               5

<210> SEQ ID NO 66
<211> LENGTH: 476
<212> TYPE: DNA
<213> ORGANISM: Artificial Sequence
<220> FEATURE:
<223> OTHER INFORMATION: Synthetic

<400> SEQUENCE: 66
taatacgact cactataggg acaattacta tttacaatta caagtctggg gctgaggtga      60
agaagcctgg ggcctcagtg aaagtttcct gcaaggcttc tggatacacc ttcagtaata    120
atgctataca ttgggtgcgc caggcccccg gacaaaggct tgaatggatg ggatggatca    180
acggtggcaa tggaaacaca gataattcac agaaattcca gggcagagtc accattacta    240
gggacacatc cgcgagcaca gcctacatgg agctgagcag cctgatatct gaagacacgg    300
ctgtatatta ctgtgcgcat agacagtata gcagctcgcc cagcccttt gacctctggg    360 gccagggaac cctggtcacc gtctcctcag ggagtgcatc cgccccaacc gactacaagg    420
acgacgacga caagtcgtcc ttagcatccg ctatttaaaa aaaaaaaaaa aaaaaa        476

<210> SEQ ID NO 67
<211> LENGTH: 67
<212> TYPE: DNA
<213> ORGANISM: Artificial Sequence
<220> FEATURE:
<223> OTHER INFORMATION: Synthetic

<400> SEQUENCE: 67
aaatagcgga tgctaaggac gacttgtcgt cgtcgtcctt gtagtcggtt ggggcggatg    60
cactccc                                                              67

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
aaaaaaaaaa aaaaaaaaaa                                                20

<210> SEQ ID NO 69
<211> LENGTH: 13
<212> TYPE: DNA
<213> ORGANISM: Artificial Sequence
<220> FEATURE:
<223> OTHER INFORMATION: Synthetic

<400> SEQUENCE: 69
tttttttttt ttt                                                       13

<210> SEQ ID NO 70
<211> LENGTH: 15
<212> TYPE: DNA
<213> ORGANISM: Artificial Sequence
<220> FEATURE:
<223> OTHER INFORMATION: Synthetic

<400> SEQUENCE: 70
gcctccctcg cgcca                                                     15

<210> SEQ ID NO 71
<211> LENGTH: 15
<212> TYPE: DNA
<213> ORGANISM: Artificial Sequence
<220> FEATURE:
<223> OTHER INFORMATION: Synthetic

<400> SEQUENCE: 71
gccttgccag cccgc                                                     15

<210> SEQ ID NO 72
<211> LENGTH: 25
<212> TYPE: DNA
<213> ORGANISM: Artificial Sequence
<220> FEATURE:
<223> OTHER INFORMATION: Synthetic

<400> SEQUENCE: 72
gggacaatta ctatttacaa ttaca                                          25

<210> SEQ ID NO 73
<211> LENGTH: 21
<212> TYPE: DNA
<213> ORGANISM: Artificial Sequence
<220> FEATURE:
<223> OTHER INFORMATION: Synthetic

<400> SEQUENCE: 73
gggagtgcat ccgccccaac c                                    21

<210> SEQ ID NO 74
<211> LENGTH: 7
<212> TYPE: PRT
<213> ORGANISM: Artificial Sequence
<220> FEATURE:
<223> OTHER INFORMATION: Synthetic

<400> SEQUENCE: 74

Gly Ser Ala Ser Ala Pro Thr
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic

<400> SEQUENCE: 75

Thr Ala Val Tyr Tyr Cys Ala Arg
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Thr Ala Val Tyr Tyr Cys Thr Arg
1               5

<210> SEQ ID NO 77
<211> LENGTH: 4
<212> TYPE: PRT
<213> ORGANISM: Artificial Sequence
<220> FEATURE:
<223> OTHER INFORMATION: Synthetic

<400> SEQUENCE: 77

Trp Gly Arg Gly
1

<210> SEQ ID NO 78
<211> LENGTH: 4
<212> TYPE: PRT
<213> ORGANISM: Artificial Sequence
<220> FEATURE:
<223> OTHER INFORMATION: Synthetic

<400> SEQUENCE: 78

Trp Gly Gln Gly
1

```
<210> SEQ ID NO 79
<211> LENGTH: 25
<212> TYPE: DNA
<213> ORGANISM: Artificial Sequence
<220> FEATURE:
<223> OTHER INFORMATION: Synthetic

<400> SEQUENCE: 79
tgtaattgta aatagtaatt gtccc                                    25

<210> SEQ ID NO 80
<211> LENGTH: 18
<212> TYPE: DNA
<213> ORGANISM: Artificial Sequence
<220> FEATURE:
<223> OTHER INFORMATION: Synthetic

<400> SEQUENCE: 80
tggggcggat gcactccc                                            18

<210> SEQ ID NO 81
<211> LENGTH: 18
<212> TYPE: DNA
<213> ORGANISM: Artificial Sequence
<220> FEATURE:
<223> OTHER INFORMATION: Synthetic

<400> SEQUENCE: 81
gggagtgcat ccgcccca                                            18

<210> SEQ ID NO 82
<211> LENGTH: 41
<212> TYPE: DNA
<213> ORGANISM: Artificial Sequence
<220> FEATURE:
<223> OTHER INFORMATION: Synthetic

<400> SEQUENCE: 82
gccttgccag cccgctcaga atttggggcg gatgcactcc c                  41

<210> SEQ ID NO 83
<211> LENGTH: 41
<212> TYPE: DNA
<213> ORGANISM: Artificial Sequence
<220> FEATURE:
<223> OTHER INFORMATION: Synthetic

<400> SEQUENCE: 83
gccttgccag cccgctcagg gaatggggcg gatgcactcc c                  41

<210> SEQ ID NO 84
<211> LENGTH: 41
<212> TYPE: DNA
<213> ORGANISM: Artificial Sequence
<220> FEATURE:
<223> OTHER INFORMATION: Synthetic

<400> SEQUENCE: 84
gccttgccag cccgctcagt taatggggcg gatgcactcc c                  41

<210> SEQ ID NO 85
<211> LENGTH: 41
<212> TYPE: DNA
<213> ORGANISM: Artificial Sequence
<220> FEATURE:
<223> OTHER INFORMATION: Synthetic
```

<400> SEQUENCE: 85
gccttgccag cccgctcagg gcctggggcg gatgcactcc c         41

<210> SEQ ID NO 86
<211> LENGTH: 41
<212> TYPE: DNA
<213> ORGANISM: Artificial Sequence
<220> FEATURE:
<223> OTHER INFORMATION: Synthetic

<400> SEQUENCE: 86
gccttgccag cccgctcagc cggtggggcg gatgcactcc c         41

<210> SEQ ID NO 87
<211> LENGTH: 41
<212> TYPE: DNA
<213> ORGANISM: Artificial Sequence
<220> FEATURE:
<223> OTHER INFORMATION: Synthetic

<400> SEQUENCE: 87
gccttgccag cccgctcagt tcctggggcg gatgcactcc c         41

<210> SEQ ID NO 88
<211> LENGTH: 41
<212> TYPE: DNA
<213> ORGANISM: Artificial Sequence
<220> FEATURE:
<223> OTHER INFORMATION: Synthetic

<400> SEQUENCE: 88
gccttgccag cccgctcaga aggtggggcg gatgcactcc c         41

<210> SEQ ID NO 89
<211> LENGTH: 41
<212> TYPE: DNA
<213> ORGANISM: Artificial Sequence
<220> FEATURE:
<223> OTHER INFORMATION: Synthetic

<400> SEQUENCE: 89
gccttgccag cccgctcagc ctttggggcg gatgcactcc c         41

<210> SEQ ID NO 90
<211> LENGTH: 21
<212> TYPE: DNA
<213> ORGANISM: Artificial Sequence
<220> FEATURE:
<223> OTHER INFORMATION: Synthetic

<400> SEQUENCE: 90
tttttttttt tttttttttt t         21

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
tttttttttt tttttttt         18

<210> SEQ ID NO 92
<211> LENGTH: 6

```
<212> TYPE: PRT
<213> ORGANISM: Artificial Sequence
<220> FEATURE:
<223> OTHER INFORMATION: Synthetic

<400> SEQUENCE: 92

Lys Lys Lys Lys Lys Lys
1               5
```